United States Patent
Miyashita et al.

(10) Patent No.: US 9,601,704 B2
(45) Date of Patent: Mar. 21, 2017

(54) ORGANIC LIGHT-EMITTING DEVICE AND DISPLAY APPARATUS

(71) Applicant: CANON KABUSHIKI KAISHA, Tokyo (JP)

(72) Inventors: Hirokazu Miyashita, Tokyo (JP); Kengo Kishino, Tokyo (JP); Jun Kamatani, Tokyo (JP); Shigemoto Abe, Yokohama (JP); Naoki Yamada, Inagi (JP); Tetsuya Kosuge, Yokohama (JP); Takayuki Horiuchi, Tokyo (JP); Yosuke Nishide, Kawasaki (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/764,204

(22) PCT Filed: Feb. 4, 2014

(86) PCT No.: PCT/JP2014/052983
§ 371 (c)(1),
(2) Date: Jul. 29, 2015

(87) PCT Pub. No.: WO2014/123239
PCT Pub. Date: Aug. 14, 2014

(65) Prior Publication Data
US 2015/0364703 A1 Dec. 17, 2015

(30) Foreign Application Priority Data
Feb. 6, 2013 (JP) .................................. 2013-021048

(51) Int. Cl.
G09G 3/30 (2006.01)
H01L 51/00 (2006.01)
(Continued)

(52) U.S. Cl.
CPC ........ H01L 51/0085 (2013.01); C07D 215/24 (2013.01); C07D 221/10 (2013.01);
(Continued)

(58) Field of Classification Search
CPC ............. H01L 51/0072; H01L 51/0085; H01L 51/0077; H01L 51/5028; H01L 51/0092;
(Continued)

(56) References Cited

U.S. PATENT DOCUMENTS 6,824,894 B2    11/2004   Takiguchi et al.
7,078,115 B2    7/2006    Takiguchi et al.
(Continued)

FOREIGN PATENT DOCUMENTS

EP    2103665 A1    9/2009
JP    9-328678 A    12/1997
(Continued)

OTHER PUBLICATIONS

Pending U.S. Appl. No. 14/758,683, filed Jun. 30, 2015 (not yet published).
(Continued)

*Primary Examiner* — Jennifer Nguyen
(74) *Attorney, Agent, or Firm* — Fitzpatrick, Cella, Harper & Scinto

(57) ABSTRACT

Provided is a long-lifetime organic light-emitting element having a good device lifetime characteristic. The organic light-emitting device includes: a pair of electrodes; and an organic compound layer placed between the pair of electrodes, in which the organic compound layer includes an iridium complex having a specific structure and a different kind of metal complex.

12 Claims, 3 Drawing Sheets

(51) Int. Cl.
| | |
|---|---|
| *C07D 263/56* | (2006.01) |
| *C07D 215/24* | (2006.01) |
| *C07D 221/10* | (2006.01) |
| *C07D 221/18* | (2006.01) |
| *C07D 233/64* | (2006.01) |
| *C07D 235/18* | (2006.01) |
| *C07D 277/66* | (2006.01) |
| *C09K 11/06* | (2006.01) |
| *G09G 3/32* | (2016.01) |
| *H01L 27/32* | (2006.01) |
| *C09B 57/00* | (2006.01) |
| *C09B 57/10* | (2006.01) |
| *H01L 51/50* | (2006.01) |

(52) U.S. Cl.
CPC ......... *C07D 221/18* (2013.01); *C07D 233/64* (2013.01); *C07D 235/18* (2013.01); *C07D 263/56* (2013.01); *C07D 277/66* (2013.01); *C09B 57/00* (2013.01); *C09B 57/10* (2013.01); *C09K 11/06* (2013.01); *G09G 3/3216* (2013.01); *H01L 27/3234* (2013.01); *H01L 27/3248* (2013.01); *H01L 51/0077* (2013.01); *H01L 51/0092* (2013.01); *C09K 2211/1007* (2013.01); *C09K 2211/1029* (2013.01); *C09K 2211/185* (2013.01); *G09G 2320/043* (2013.01); *G09G 2320/045* (2013.01); *H01L 51/5016* (2013.01); *H01L 51/5028* (2013.01)

(58) Field of Classification Search
CPC ............ H01L 27/3248; H01L 51/0073; H01L 51/0056; H01L 51/5092; H01L 27/3234; G09G 3/3208; G09G 3/3216; H05B 33/0896; G03G 15/04054
USPC ........................................ 345/76–82; 257/40
See application file for complete search history.

(56) References Cited

U.S. PATENT DOCUMENTS

| | | | | |
|---|---|---|---|---|
| 7,232,618 | B2 | 6/2007 | Yamada et al. | |
| 7,976,958 | B2 | 7/2011 | Takiguchi et al. | |
| 8,330,153 | B2 | 12/2012 | Ooishi et al. | |
| 8,557,401 | B2 * | 10/2013 | Kosuge | C07C 15/38 313/504 |
| 8,889,858 | B2 * | 11/2014 | Inoue | 544/225 |
| 2007/0231601 | A1 | 10/2007 | Nakasu et al. | |
| 2008/0210930 | A1 | 9/2008 | Kamatani et al. | |
| 2009/0066226 | A1 * | 3/2009 | Sugita | C07D 405/14 313/504 |
| 2009/0159130 | A1 | 6/2009 | Eum et al. | |
| 2009/0165860 | A1 | 7/2009 | Kim et al. | |
| 2010/0219407 | A1 * | 9/2010 | Kamatani | C07C 17/14 257/40 |

FOREIGN PATENT DOCUMENTS

| | | |
|---|---|---|
| JP | 3760508 B2 | 3/2006 |
| JP | 2006-93197 A | 4/2006 |
| JP | 2009-114137 A | 5/2009 |
| JP | 2009-152568 A | 7/2009 |
| JP | 2009-218571 A | 9/2009 |

OTHER PUBLICATIONS

Pending U.S. Appl. No. 14/648,494, filed May 29, 2015 (not yet published).
Pending U.S. Appl. No. 14/648,095, filed May 28, 2015 (not yet published).
Pending U.S. Appl. No. 14/761,049, filed Jul. 15, 2015 (not yet published).
Pending U.S. Appl. No. 14/760,093, filed Jul. 9, 2015 (not yet published).
Pending U.S. Appl. No. 14/649,048, filed Jun. 2, 2015 (not yet published).
Pending U.S. Appl. No. 14/764,376, filed Jul. 29, 2015 (not yet published).
Anhui Wu et al., "Regiospecific Oxidation of Polycyclic Aromatic Phenols to Quinones by Hypervalent Iodine Reagents," 66 Tetrahedron 2111-2118 (2010).
Sergey Lamansky et al., "Highly Phosphorescent Bis-Cyclometalated Iridium Complexes: Synthesis, Photophysical Characterization, and Use in Organic Light Emitting Diodes," 123 J. Am. Chem. Soc. 4304-4312 (2001).
Richard H. Wiley et al., "Substituted 4,7-Phenanthrolines and Benzo[f]quinolines as Scintillation Solutes," 23(2) J. Org. Chem. 268-271 (1958).
Kevin R. Roesch et al., "Synthesis of Isoquinolines and Pyridines by the Palladium-Catalyzed Iminoannulation of Internal Alkynes," 66(24) J. Org. Chem. 8042-8051 (2001).
F. Eloy et al., "Sur une Methode Nouvelle de Synthese des Aza-2 Phenanthrenes (Benzo[f]isoquinoleines)," 6 Chimica Therapeutica 48-49 (1971) (document in French with English summary).
Stephen P. Fletcher et al., "Oxidation of p-Aminophenols and Formal Radical Cyclization onto Benzene Rings: Formation of Benzo-Fused Nitrogen Heterocycles," 7(1) Organic Letters 23-26 (2005).
European search report issued in corresponding application No. 14748523.9 dated Oct. 14, 2016—5 pages.

* cited by examiner

ORGANIC LIGHT-EMITTING DEVICE AND DISPLAY APPARATUS

TECHNICAL FIELD

The present invention relates to an organic light-emitting device and a display apparatus including the device.

BACKGROUND ART

An organic light-emitting device (organic electroluminescence device or organic EL device) is an electronic device including a pair of electrodes and an organic compound layer placed between the pair of electrodes. An electron and a hole are injected from the pair of electrodes, and then the electron and the hole recombine in the organic compound layer to produce an exciton of a luminous organic compound. The organic light-emitting device emits light upon return of the exciton to its ground state.

Recent development of the organic light-emitting devices is significant and the developed devices have, for example, the following features. The light-emitting devices can be driven at low voltages, emit light beams having various wavelengths, have high-speed responsiveness, and can be reduced in thickness and weight.

By the way, creation of a compound suitable for the organic light-emitting device has been vigorously performed heretofore. This is because creation of a compound having an excellent device lifetime characteristic is important for providing a high-performance organic light-emitting device.

For example, an iridium complex having a red light-emitting arylnaphtho[2,1-f]isoquinoline as a ligand is known as a phosphorous light-emitting material having a high emission quantum yield. In Patent Literature 1, as the iridium complex having an arylnaphtho[2,1-f]isoquinoline ligand, there is a disclosure of Compound E2 shown below.

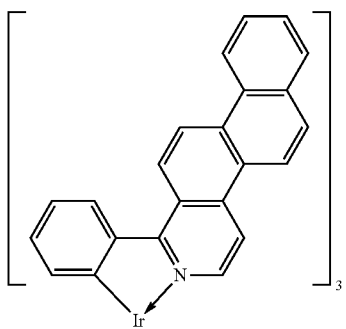

E2

In addition, another example of the metal complex to be used as a constituent material for the organic light-emitting device is such a metal complex as disclosed in Patent Literature 2. Meanwhile, a metal complex disclosed in Patent Literature 3 or Patent Literature 4 is available as a metal complex to be incorporated as a host into an emission layer together with the iridium complex.

CITATION LIST

Patent Literature

PTL 1: Japanese Patent Application Laid-Open No. 2009-114137
PTL 2: Japanese Patent No. 3760508
PTL 3: Japanese Patent Application Laid-Open No. 2009-152568
PTL 4: Japanese Patent Application Laid-Open No. 2009-218571

Non Patent Literature

NPL 1: Tetrahedron, (2010), vol. 66, p. 2111-2118
NPL 2: J. Am. Chem. Soc., (2001), vol. 123, p. 4304-4312
NPL 3: J. Org. Chem. (2001), Vol. 66, 8042-8051
NPL 5: Org. Lett., Vol. 7, No. 1, pp. 23-26, 2005
NPL 6: Chimica Therapeutica (1971), Vol. 6(1), 48-49
NPL 7: J. Org. Chem. (1958), Vol. 23, 268-271

SUMMARY OF INVENTION

Solution to Problem

According to one embodiment of the present invention, there is provided an organic light-emitting device, including: a pair of electrodes; and an organic compound layer placed between the pair of electrodes, in which the organic compound layer includes an iridium complex represented by the following general formula [1] and a metal complex represented by the following general formula [5].

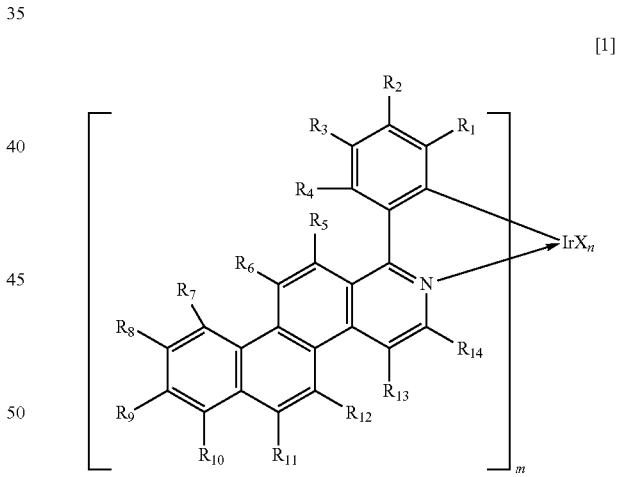

[1]

In the formula [1]: m represents an integer of 1 to 3, and n represents an integer of 0 to 2, provided that a relationship of m+n=3 is satisfied; $R_1$ to $R_{14}$ each represent a hydrogen atom, a halogen atom, an alkyl group, an alkoxy group, a substituted amino group, a substituted or unsubstituted aryl group, or a substituted or unsubstituted heterocyclic group, and may be identical to or different from one another, provided that when m represents 3 or when X is free of an alkyl group, at least one of substituents represented by $R_1$ to $R_{14}$ includes an alkyl group; X represents a bidentate ligand; and a partial structure $IrX_n$ represents any one of partial structures represented by the following general formulae [2] to [4].

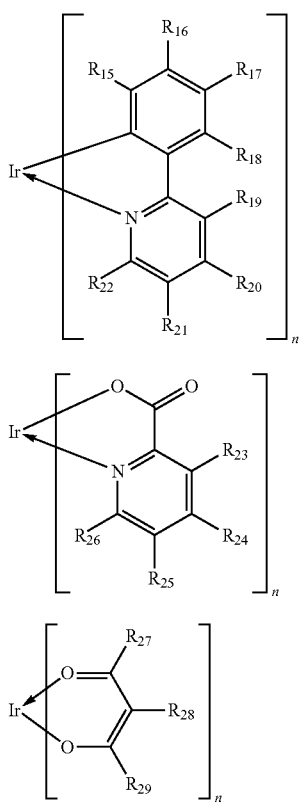

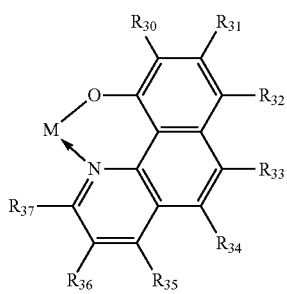

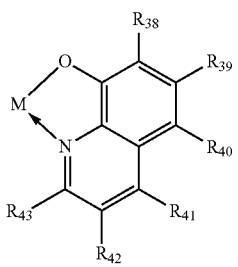

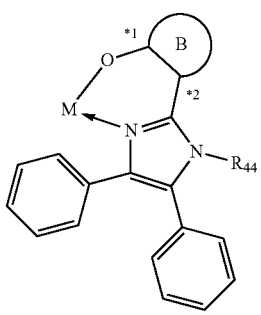

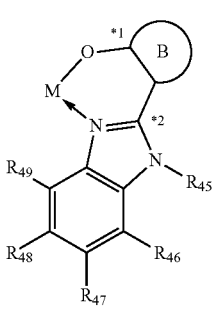

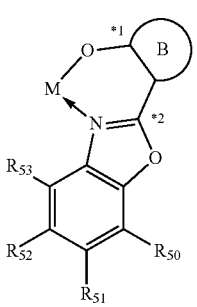

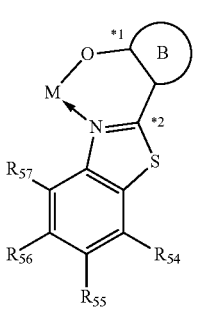

In the formulae [2] to [4], $R_{15}$ to $R_{29}$ each represent a hydrogen atom, an alkyl group, an alkoxy group, a substituted amino group, a substituted or unsubstituted aryl group, or a substituted or unsubstituted heterocyclic group, and may be identical to or different from one another, provided that when none of $R_1$ to $R_{14}$ represents an alkyl group, at least one of substituents represented by $R_{15}$ to $R_{29}$ includes an alkyl group, and when n represents 2, multiple substituents represented by any one of $R_{15}$ to $R_{29}$ may be identical to or different from each other;

$$ML_2 \quad [5]$$

in the formula [5]: M represents a divalent metal atom selected from beryllium, magnesium, and zinc; L represents a bidentate ligand; when M represents beryllium or magnesium, a partial structure ML includes any one of structures represented by the following general formulae [6] to [11]; and when M represents zinc, the partial structure ML includes any one of structures represented by the following general formulae [7] to [11].

In the formulae [6] to [11], $R_{30}$ to $R_{57}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group, and in the formulae [8] to [11], a ring B includes any one of cyclic structures represented by the following general formulae [12] to [14], *1 represents a bonding position with an oxygen atom, and *2 represents a bonding position with a carbon atom in a five-membered heterocyclic skeleton.

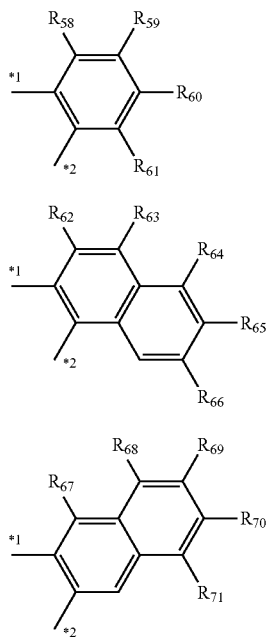

[12]

[13]

[14]

In the formulae [12] to [14], $R_{58}$ to $R_{71}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

Further features of the present invention will become apparent from the following description of exemplary embodiments with reference to the attached drawings.

DESCRIPTION OF EMBODIMENTS

Figure 1:
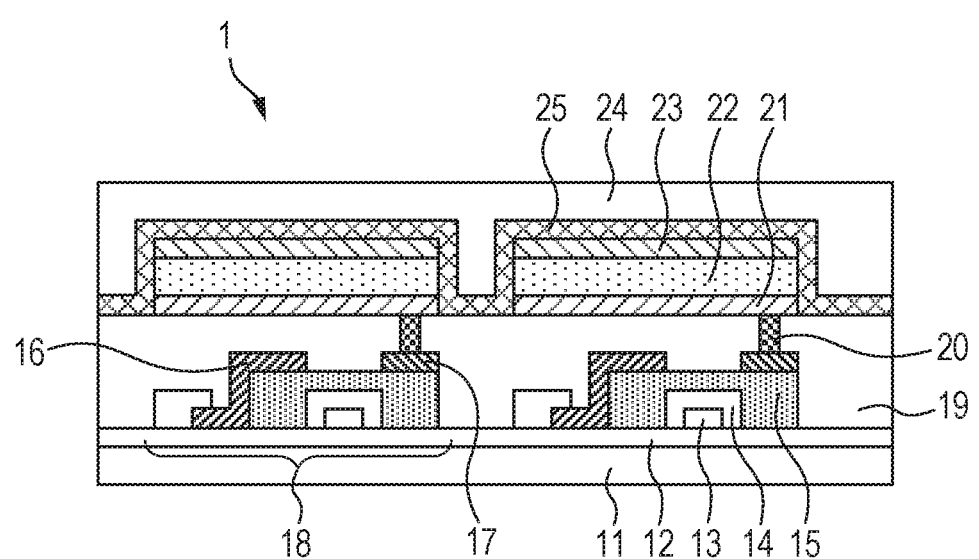
FIG. 1 is a schematic sectional view illustrating a display apparatus including an organic light-emitting device and a switching device connected to the organic light-emitting device.

In PTL 1, the iridium complex having an arylnaphtho[2,1-f]isoquinoline ligand such as Compound E2 has not been used as a guest to be incorporated into an emission layer. In addition, an investigation conducted by the inventors of the present invention has found that Compound E2 is not suitable for an organic light-emitting device because of its remarkably high crystallinity. In addition, in PTL 1, a material to be incorporated as a host into an emission layer is a nitrogen-containing aromatic compound such as CBP and there is no disclosure of an organic light-emitting device in which a host to be incorporated into the emission layer is a metal complex. In addition, the metal complex disclosed in PTL 2 has not been used as a host to be incorporated into the emission layer together with the phosphorescent light-emitting material. Further, the emission efficiency of an organic light-emitting device obtained by incorporating the metal complex disclosed in PTL 3 or PTL 4 as a host into its emission layer is also low.

Therefore, none of the organic light-emitting devices disclosed in PTLs 1 to 4 has been able to obtain high emission efficiency and a high lifetime characteristic.

The present invention has been accomplished to solve the problems, and an object of the present invention is to provide an organic light-emitting device having a good device lifetime characteristic.

Hereinafter, the present invention is described in detail.

(1) Organic Light-Emitting Device

An organic light-emitting device of the present invention is a light-emitting device including at least: an anode and a cathode as a pair of electrodes opposite to each other; and an organic compound layer placed between the pair of electrodes. In addition, the organic light-emitting device of the present invention includes, in the organic compound layer, an iridium complex represented by the following general formula [1] and a metal complex compound represented by the following general formula [5].

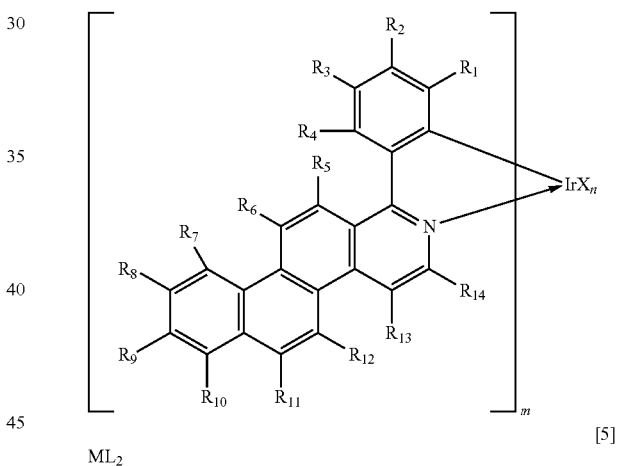

[1]

[5]

ML$_2$

It should be noted that details about the iridium complex represented by the general formula [1] and the metal complex compound represented by the general formula [5] are described later.

The device construction of the organic light-emitting device of the present invention is, for example, a multilayer-type device construction obtained by sequentially stacking, on a substrate, electrode layers and an organic compound layer described in each of the following constructions (1) to (6). It is to be noted that in each of the device constructions, the organic compound layer necessarily includes a emission layer including a light-emitting material.

(1) Anode/emission layer/cathode
(2) Anode/hole transport layer/emission layer/electron transport layer/cathode
(3) Anode/hole transport layer/emission layer/electron transport layer/electron-injecting layer/cathode
(4) Anode/hole-injecting layer/hole transport layer/emission layer/electron transport layer/cathode (5) Anode/hole-injecting layer/hole transport layer/emission layer/electron transport layer/electron-injecting layer/cathode (6) Anode/hole transport layer/electron blocking layer/emission layer/hole blocking layer/electron transport layer/cathode It is to be noted that those device construction examples are only very basic device constructions and the device construction of the organic light-emitting device of the present invention is not limited thereto.

For example, the following various layer constructions can each be adopted: an insulating layer, an adhesion layer, or an interference layer is formed at an interface between an electrode and the organic compound layer, the electron transport layer or the hole transport layer is constructed of two layers having different ionization potentials, or the emission layer is constructed of two layers including different light-emitting materials.

In the present invention, the aspect according to which light output from the emission layer is extracted (device form) may be the so-called bottom emission system in which the light is extracted from an electrode on a side closer to the substrate or may be the so-called top emission system in which the light is extracted from a side opposite to the substrate. In addition, a double-face extraction system in which the light is extracted from each of the side closer to the substrate and the side opposite to the substrate can be adopted.

Of the device constructions (1) to (6), the construction (6) is preferred because the construction includes both the electron blocking layer and the hole blocking layer. In other words, the construction (6) including the electron blocking layer and the hole blocking layer provides an organic light-emitting device that does not cause any carrier leakage and has high emission efficiency because both carriers, i.e., a hole and an electron can be trapped in the emission layer with reliability.

In the organic light-emitting device of the present invention, the iridium complex represented by the general formula [1] and the metal complex compound represented by the general formula [5] are preferably incorporated into the emission layer out of the organic compound layer. In this case, the emission layer includes at least the iridium complex represented by the general formula [1] and the metal complex compound represented by the general formula [5]. The applications of the compounds to be incorporated into the emission layer in this case vary depending on their content concentrations in the emission layer. Specifically, the compounds are classified into a main component and a sub-component depending on their content concentrations in the emission layer.

The compound serving as the main component is a compound having the largest weight ratio (content concentration) out of the group of compounds to be incorporated into the emission layer and is a compound also called a host. In addition, the host is a compound present as a matrix around the light-emitting material in the emission layer, and is a compound mainly responsible for the transport of a carrier to the light-emitting material and the donation of an excitation energy to the light-emitting material.

In addition, the compound serving as the sub-component is a compound except the main component and can be called a guest (dopant), a light emission assist material, or a charge-injecting material depending on a function of the compound. The guest as one kind of sub-component is a compound (light-emitting material) responsible for main light emission in the emission layer. The light emission assist material as one kind of sub-component is a compound that assists the light emission of the guest and is a compound having a smaller weight ratio (content concentration) in the emission layer than that of the host. The light emission assist material is also called a second host by virtue of its function.

The concentration of the guest with respect to the host is 0.01 wt % or more and 50 wt % or less, preferably 0.1 wt % or more and 20 wt % or less with reference to the total amount of the constituent materials for the emission layer. The concentration of the guest is particularly preferably 10 wt % or less from the viewpoint of preventing concentration quenching.

In the present invention, the guest may be uniformly incorporated into the entirety of the layer in which the host serves as a matrix, or may be incorporated so as to have a concentration gradient. In addition, the guest may be partially incorporated into a specific region in the emission layer to make the layer a layer having a region free of the guest and formed only of the host.

In the present invention, the following aspect is preferred: both the iridium complex represented by the general formula [1] and the metal complex compound represented by the general formula [5] are incorporated as the guest and the host, respectively, into the emission layer. In this case, in addition to the iridium complex represented by the general formula [1], another phosphorescent light-emitting material may be further incorporated into the emission layer for assisting the transfer of an exciton or a carrier.

In addition, a compound different from the metal complex compound represented by the general formula [5] may be further incorporated as the second host into the emission layer for assisting the transfer of the exciton or the carrier. In the present invention, the (light emission) assist material is preferably an iridium complex. It is to be noted that the iridium complex to be used as the (light emission) assist material is an iridium complex except the iridium complex represented by the general formula [1].

(2) Iridium Complex

Next, the iridium complex as one constituent material for the organic light-emitting device of the present invention is described. The iridium complex as one constituent material for the organic light-emitting device of the present invention is a compound represented by the following general formula [1].

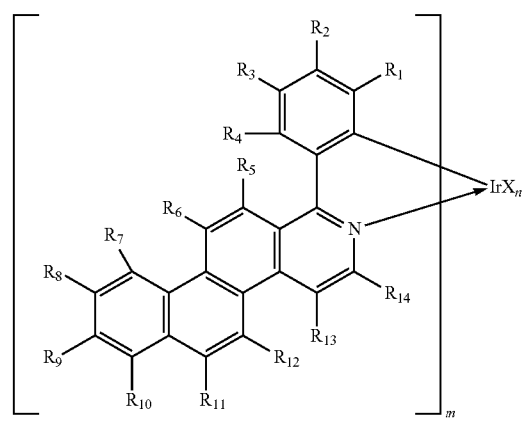

[1]

In the formula [1], m represents an integer of 1 to 3, and n represents an integer of 0 to 2, provided that a relationship of m+n=3 is satisfied.

In the formula [1], $R_1$ to $R_{14}$ each represent a hydrogen atom, a halogen atom, an alkyl group, an alkoxy group, a substituted amino group, a substituted or unsubstituted aryl group, or a substituted or unsubstituted heterocyclic group. It is to be noted that when m represents 3 or when X to be described later is free of an alkyl group, at least one of substituents represented by $R_1$ to $R_{14}$ is an alkyl group.

Examples of the halogen atom represented by any one of $R_1$ to $R_{14}$ include fluorine, chlorine, bromine, and iodine atoms.

The alkyl group represented by any one of $R_1$ to $R_{14}$ is preferably an alkyl group having 1 or more and 10 or less carbon atoms, more preferably an alkyl group having 1 or more and 6 or less carbon atoms. Specific examples of the alkyl group having 1 or more and 6 or less carbon atoms include a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group. Of those alkyl groups, a methyl group or a tert-butyl group is particularly preferred. It is to be noted that part or all of hydrogen atoms in the alkyl group represented by any one of $R_1$ to $R_{14}$ may be substituted with a fluorine atom as in a trifluoromethyl group or the like.

Specific examples of the alkoxy group represented by any one of $R_1$ to $R_{14}$ include, but, of course, not limited to, a methoxy group, an ethoxy group, an i-propoxy group, an n-butoxy group, and a tert-butoxy group. Of those alkoxy groups, a methoxy group or an ethoxy group is preferred.

Specific examples of the substituted amino group represented by any one of $R_1$ to $R_{14}$ include, but, of course, not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisoylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group. Of those substituted amino groups, an N,N-dimethylamino group or an N,N-diphenylamino group is preferred.

Specific examples of the aryl group represented by any one of $R_1$ to $R_{14}$ include, but, of course, not limited to, a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group. Of those aryl groups, a phenyl group, a naphthyl group, a fluorenyl group, or a biphenyl group is preferred, and a phenyl group is more preferred.

Specific examples of the heterocyclic group represented by any one of $R_1$ to $R_{14}$ include, but, of course, not limited to, a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group.

The aryl group and heterocyclic group represented by $R_1$ to $R_{14}$ may each further have a substituent. Specific examples thereof include: alkyl groups such as a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group; halogen atoms such as fluorine, chlorine, bromine, and iodine atoms; alkoxy groups such as a methoxy group, an ethoxy group, an i-propoxy group, an n-butoxy group, and a tert-butoxy group; substituted amino groups such as an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphtylamino group, an N,N-difluorenylamino group, an N-phenyl-N-tolylamino group, an N,N-ditolylamino group, an N-methyl-N-phenylamino group, an N,N-dianisoylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group; aryl groups such as a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group; and heterocyclic groups such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group. Of those substituents listed above, a methyl group, a tert-butyl group, an N,N-dimethylamino group, an N,N-diphenylamino group, a phenyl group, a naphthyl group, a fluorenyl group, or a biphenyl group is preferred. Here, when the aryl group and heterocyclic group represented by any one of $R_1$ to $R_{14}$ each further have an aryl group, a phenyl group is particularly preferred.

In the formula [1], X represents a bidentate ligand. In the present invention, a partial structure $IrX_n$ of the complex including X is specifically any one of the structures represented by the following general formulae [2] to [4].

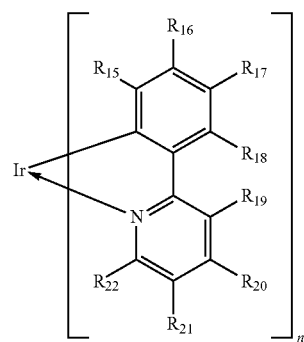

[2]

-continued

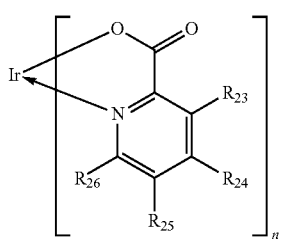

[3]

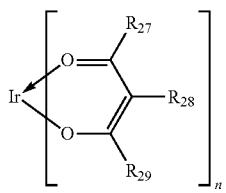

[4]

In the formulae [2] to [4], $R_{15}$ to $R_{29}$ each represent a hydrogen atom, a halogen atom, an alkyl group, an alkoxy group, a substituted amino group, a substituted or unsubstituted aryl group, or a substituted or unsubstituted heterocyclic group.

Specific examples of the halogen atom, alkyl group, alkoxy group, substituted amino group, aryl group, and heterocyclic group represented by $R_{15}$ to $R_{29}$ are the same as the specific examples of $R_1$ to $R_{14}$ in the general formula [1]. In addition, when the substituent represented by any one of $R_{15}$ to $R_{29}$ is an aryl group or a heterocyclic group, specific examples of the substituent that the substituent may further have are the same as the specific examples in $R_1$ to $R_{14}$ in the general formula [1]. It is to be noted that when none of $R_1$ to $R_{14}$ in the formula [1] represents an alkyl group, at least one of the substituents represented by any one of $R_{15}$ to $R_{29}$ is an alkyl group. In addition, when n represents 2, multiple substituents represented by any one of $R_{15}$ to $R_{29}$ may be identical to or different from each other.

The substituent represented in any one of the formulae [2] to [4], i.e., any one of $R_{15}$ to $R_{29}$ preferably represents a hydrogen atom, an alkyl group having 1 to 4 carbon atoms, or a phenyl group that may be substituted with an alkyl group having 1 to 4 carbon atoms.

In the iridium complex represented by the general formula [1], m preferably represents 2 and n preferably represents 1.

In addition, the iridium complex represented by the general formula [1] is preferably an iridium complex represented by the following general formula [15].

[15]

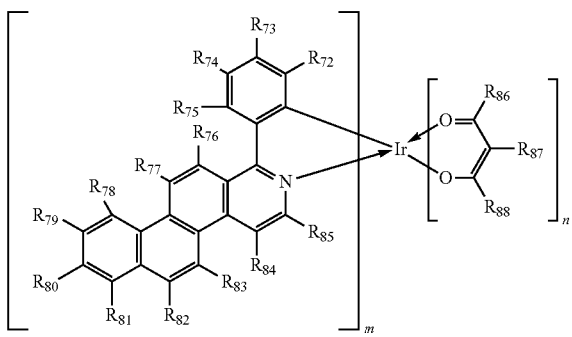

In the formula [15], $R_{72}$ to $R_{88}$ each represent a hydrogen atom, a halogen atom, an alkyl group, an alkoxy group, a substituted amino group, a substituted or unsubstituted aryl group, or a substituted or unsubstituted heterocyclic group. It is to be noted that at least one of $R_{72}$ to $R_{88}$ represents an alkyl group.

Specific examples of the halogen atom, alkyl group, alkoxy group, substituted amino group, aryl group, and heterocyclic group represented by $R_{72}$ to $R_{88}$ are the same as the specific examples of $R_1$ to $R_{14}$ in the general formula [1]. In addition, when the substituent represented by any one of $R_{72}$ to $R_{88}$ is an aryl group or a heterocyclic group, specific examples of the substituent that the aryl group and the heterocyclic group may each further have are the same as the specific examples of $R_1$ to $R_{14}$ in the general formula [1].

The substituents represented in the formula [15], i.e., $R_{72}$ to $R_{88}$ each preferably represent a hydrogen atom, an alkyl group having 1 to 4 carbon atoms, or a phenyl group that may be substituted with an alkyl group having 1 to 4 carbon atoms.

In the formula [15], m represents an integer of 1 to 3 and n represents an integer of 0 to 2, provided that a relationship of m+n=3 is satisfied.

In addition, the iridium complex represented by the general formula [1] is particularly preferably an iridium complex represented by the following general formula [16].

[16]

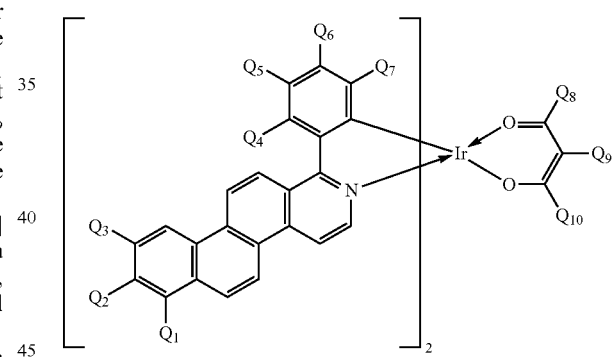

In the formula [16], $Q_1$ to $Q_{10}$ each represent a hydrogen atom, an alkyl group, an alkoxy group, a substituted amino group, or a substituted or unsubstituted phenyl group, provided that at least one of $Q_1$ to $Q_{10}$ represents an alkyl group.

Specific examples of the substituent that the alkyl group, alkoxy group, and phenyl group represented by $Q_1$ to $Q_{10}$ may each further have are the same as the specific examples in $R_1$ to $R_{14}$ in the general formula [1].

The substituents represented in the formula [16], i.e., $Q_1$ to $Q_{10}$ each preferably represent a hydrogen atom, an alkyl group having 1 to 4 carbon atoms, or a phenyl group that may be substituted with an alkyl group having 1 to 4 carbon atoms.

As described above, in the iridium complex represented by the general formula [1], at least one of the three ligands that the complex itself has is a ligand necessarily having at least one substituent such as an alkyl group in a basic skeleton shown below.

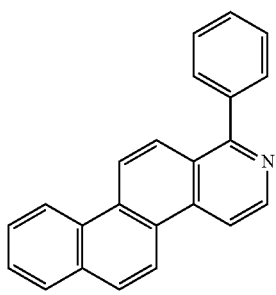

On the other hand, the iridium complex (Compound E2) disclosed in PTL 1 is a metal complex formed of a ligand that does not have any substituent such as an alkyl group in the basic skeleton.

In general, when a wide Π-conjugated plane free of steric hindrance is present in a compound, the amorphous property of the material reduces. In addition, Π-conjugated planes are stacked to raise its crystallinity. As a result, its solubility in a solvent reduces, or the material decomposes upon sublimation purification or vapor deposition, and hence its handleability deteriorates. In addition, when the material decomposes, a deteriorated product of the material or an impurity produced by the decomposition serves as a carrier trap in a device to break the carrier balance of the device, thereby deteriorating the durability of the device.

In addition, the Π-conjugated planes are stacked to form an excimer, and hence a low-energy state is established. Accordingly, when such material is incorporated into an emission layer constituting an organic light-emitting device especially as a guest, moieties associated with each other serve as a carrier trap to break the carrier balance of the device, thereby deteriorating the durability of the device. Alternatively, an energy level formed by the association becomes lower than the energy level of the guest to preclude energy transfer to the guest, which causes a reduction in emission efficiency of the device.

However, when one or more alkyl groups are present as steric hindrance groups in a compound like the iridium complex represented by the general formula [1], the association of the compound is suppressed to improve its solubility. In addition, its sublimability is improved and its handleability is also improved. Further, the use of the compound as a light-emitting material for a device can be expected to lengthen the lifetime of the device and to improve the efficiency thereof because the use can suppress excimer formation.

Here, a substituent for providing steric hindrance is, for example, an alkyl group that prevents light-emitting ligands from approaching each other such as a methyl group or a tert-butyl group. The introduction of such substituent can cause the device to emit light without reducing its emission efficiency even when the light-emitting material is doped at a concentration as high as 5 wt % or more with respect to the matrix.

In addition, when the iridium complex represented by the general formula [1] is used as a constituent material for an organic light-emitting device, the complex is preferably subjected to sublimation purification immediately before its use. This is because the sublimation purification exhibits a large purifying effect in an increase in purity of an organic compound. Such sublimation purification generally requires higher temperature as the molecular weight of the organic compound increases, and hence the thermal decomposition or the like of the compound is liable to occur owing to the high temperature at this time. Therefore, the molecular weight of the organic compound to be used as a constituent material for the organic light-emitting device is preferably 1,200 or less, more preferably 1,100 or less so that the sublimation purification can be performed without any excessive heating.

Accordingly, the iridium complex represented by the general formula [1] is more preferably an iridium complex formed of two ligands of an arylnaphtho[2,1-f]isoquinoline derivative and a bidentate ligand having a smaller molecular weight than that of the arylnaphtho[2,1-f]isoquinoline rather than a homoleptic iridium complex in which all three ligands are formed of the same arylnaphtho[2,1-f]isoquinoline derivative from the viewpoint of sublimability. Therefore, it is preferred that in the iridium complex represented by the general formula [1], m represent 2 and n represent 1.

(3) Metal Complex Compound Serving as Host

Next, the metal complex compound to be used as the host of the emission layer in the organic light-emitting device of the present invention is described. The metal complex compound serving as the host to be incorporated into the organic light-emitting device of the present invention is specifically a compound represented by the following general formula [5].

$$ML_2 \qquad [5]$$

In the formula [5], M represents a divalent metal atom selected from beryllium, magnesium, and zinc.

In the formula [5], L represents a bidentate ligand.

In the formula [5], when M represents beryllium or magnesium, the partial structure ML is any one of the structures represented by the following general formulae [6] to [11]. In addition, when M represents zinc, the partial structure ML is any one of the structures represented by the following general formulae [7] to [11].

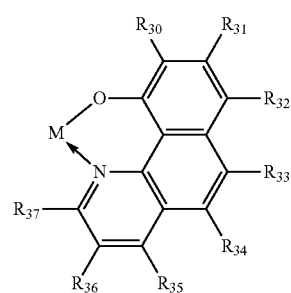

[6]

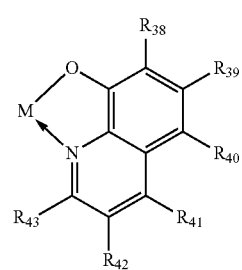

[7]

[8]

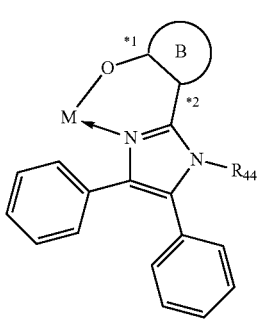

[9]

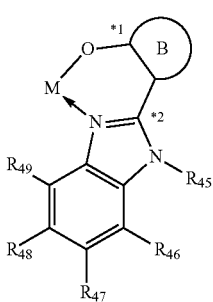

[10]

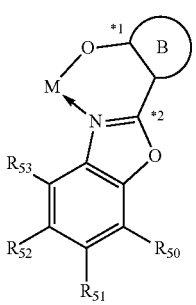

[11]

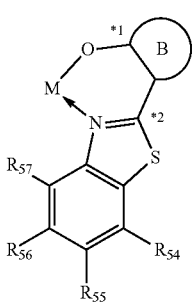

In the formulae [6] to [11], $R_{30}$ to $R_{57}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

Specific examples of the halogen atom represented by any one of $R_{30}$ to $R_{57}$ include fluorine, chlorine, bromine, and iodine atoms.

The alkyl group represented by any one of $R_{30}$ to $R_{57}$ is preferably an alkyl group having 1 or more and 6 or less carbon atoms. Specific examples of the alkyl group having 1 or more and 6 or less carbon atoms include a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group. Of those alkyl groups, a methyl group or a tert-butyl group is particularly preferred.

Specific examples of the alkoxy group represented by any one of $R_{30}$ to $R_{57}$ include, but, of course, not limited to, a methoxy group, an ethoxy group, an i-propoxy group, an n-butoxy group, a tert-butoxy group, a 2-ethyl-octyloxy group, and a benzyloxy group. Of those alkoxy groups, a methoxy group or an ethoxy group is preferred.

Examples of the substituted amino group represented by any one of $R_{30}$ to $R_{57}$ include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphtylamino group, an N,N-difluorenylamino group, an N-phenyl-N-tolylamino group, an N,N-ditolylamino group, an N-methyl-N-phenylamino group, an N,N-dianisoylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Specific examples of the aromatic hydrocarbon group represented by any one of $R_{30}$ to $R_{57}$ include, but, of course, not limited to, a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group. Of those aromatic hydrocarbon groups, a phenyl group, a naphthyl group, a fluorenyl group, or a biphenyl group is preferred, and a phenyl group is more preferred.

Specific examples of the heteroaromatic group represented by any one of $R_{30}$ to $R_{57}$ include, but, of course, not limited to, a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group.

Examples of the substituent that the alkyl group, the aromatic hydrocarbon group, and the heteroaromatic group may each further have include: alkyl groups such as a methyl group, an ethyl group, and a propyl group; aralkyl groups such as a benzyl group; aryl groups such as a phenyl group, a biphenyl group, and a tetrakis(9,9-dimethylfluorenyl) group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, and a propoxyl group; aryloxyl groups such as a phenoxyl group; halogen atoms such as fluorine, chlorine, bromine, and iodine atoms; and a cyano group.

The substituents represented in any one of the formulae [6] to [11], i.e., $R_{30}$ to $R_{57}$ each preferably represent a hydrogen atom, an alkyl group having 1 to 4 carbon atoms, or a phenyl group that may be substituted with an alkyl group having 1 to 4 carbon atoms.

In the formulae [8] to [11], *1 represents a bonding position with an oxygen atom and *2 represents a bonding position with a carbon atom sandwiched between heteroatoms in a heterocyclic five-membered ring skeleton represented below.

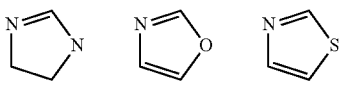 [SMILES: C1=NCCN1 ; c1cocn1 ; c1cscn1]

In the formulae [8] to [11], a ring B is any one of the cyclic structures represented by the following general formulae [12] to [14].

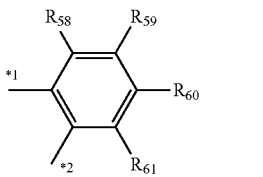

[12]

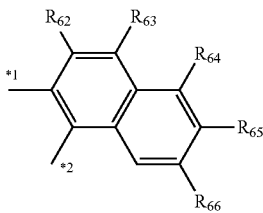

[13]

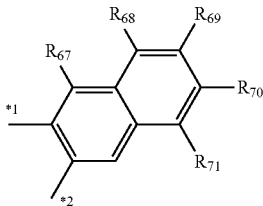

[14]

In the formulae [12] to [14], $R_{58}$ to $R_{71}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

Specific examples of the halogen atom, alkyl group, alkoxy group, substituted amino group, aromatic hydrocarbon group, and heteroaromatic group represented by $R_{58}$ to $R_{71}$, and the substituent that the alkyl group, the aromatic hydrocarbon group, and the heteroaromatic group may each further have are the same as the specific examples in $R_{30}$ to $R_{57}$ in the general formulae [6] to [11].

(4) Actions and effects exhibited by host and guest The organic compound layer (especially the emission layer) constituting the organic light-emitting device of the present invention includes at least the iridium complex represented by the general formula [1] and the metal complex represented by the general formula [5]. The iridium complex represented by the formula [1] is an organometallic complex in which at least one arylnaphtho[2,1-f]isoquinoline ligand coordinates to an iridium metal, i.e., a niq-based Ir complex. Here, as disclosed in PTL 1, the niq-based Ir complex is a phosphorescent light-emitting material having a high emission quantum yield and capable of emitting red light. Here, the term "red light emission" refers to such light emission that an emission peak wavelength is 580 nm or more and 650 nm or less, i.e., the lowest triplet excited level ($T_1$) falls within the range of 1.9 eV or more to 2.1 eV or less. Therefore, the incorporation of the niq-based Ir complex as a guest into the emission layer makes the emission efficiency of the organic light-emitting device extremely high.

Meanwhile, performances required in the organic light-emitting device are, for example, a luminescent color, a driving voltage, and a device lifetime as well as the emission efficiency. A high-performance organic light-emitting device can be produced by satisfying those requirements.

The optimization of the combination of the light-emitting material and the host is important for realizing the high-performance organic light-emitting device. Here, when a material that emits phosphorescence at room temperature is used as the light-emitting material, the following items are important:

[Item 1] a relationship between the excitation energies ($T_1$) in a triplet state of the light-emitting material and the host;

[Item 2] a relationship between the band gaps ($S_1$) of the light-emitting material and the host;

[Item 3] a relationship between the HOMO-LUMO's of the light-emitting material and the host; and

[Item 4] the emission efficiency of the light-emitting material.

The fact that [Item 1] is important results from the fact that the light emission of the phosphorescent light-emitting material is light emission from the $T_1$. If values for the $T_1$ of the host and the $T_1$ of the light-emitting material are close to each other, an energy (emission energy) needed for the light-emitting material to emit phosphorescence is absorbed by the host. In that case, the emission efficiency reduces. Accordingly, the values for the $T_1$ of the host and the $T_1$ of the light-emitting material are prevented from becoming close to each other. In addition, the materials are preferably selected so that the host may have a longer phosphorescence lifetime than that of the light-emitting material. This is because in that case, the energy can be passed to the light-emitting material. In this respect, the host to be used is a metal complex having a $T_1$ in terms of a wavelength shorter than that of the light-emitting material by 30 nm or more, and having a longer phosphorescence lifetime and a smaller atomic number than those of the light-emitting material. As a result, the high-performance organic light-emitting device can be produced.

It is because the $S_1$ of each material is largely involved in the driving voltage of the device that the fact that [Item 2] is important. Here, values for the $S_1$'s of the light-emitting material and the host are preferably set to be as close as possible to each other in order that the driving voltage of the device may be reduced. In this respect, in view of a relationship between the $S_1$ and $T_1$ of the host, a difference between the $S_1$ and the $T_1$ is preferably as small as possible.

It is because the HOMO-LUMO of each of the light-emitting material and the host is largely related to the driving voltage that the fact that [Item 3] is important. Here, the HOMO-LUMO level of the light-emitting material (phosphorescent light-emitting material) to be used in the organic light-emitting device of the present invention is shallow and hence the emission layer traps a hole. In this regard, when the trapping property of the layer is excessively high, the voltage increases and hence the power consumption of the device increases. Accordingly, a material having as shallow an HOMO as possible needs to be used as the host.

It is because the emission efficiency directly affects the performance of the organic light-emitting device that the fact that [Item 4] is important. Therefore, the use of a high-efficiency light-emitting material is essential for the production of the high-performance organic light-emitting device. In that respect, the light-emitting material used in the present invention is a light-emitting material having very high emission efficiency out of the light-emitting materials that emit red light.

Upon combination of the light-emitting material and the host for producing the high-performance organic light-emitting device in consideration of the four items, the emission efficiency of the light-emitting material itself needs to be improved (a light-emitting material having high emission efficiency needs to be selected). In addition, a material having a small $S_1$ and a small $T_1$ needs to be selected as the host. A material optimum as a host satisfying those conditions is a metal complex. This is because the metal complex has a small $S_1$ and its HOMO can be shallowed as compared to any other compound. In addition, the light-emitting material emits light having a wavelength of 610 nm or more, and hence a metal having a $T_1$ of 580 nm or less, and having a longer phosphorescence lifetime and a smaller atomic number than those of the light-emitting material is preferably used in the metal complex to be used as the host.

In this respect, the organic light-emitting device including the iridium complex represented by the general formula [1] and the metal complex represented by the general formula [5] has higher performance than that of a related art phosphorescent light-emitting device particularly from the viewpoint of emission efficiency.

(5) Specific Examples of Iridium Complex

Specific structural formulae of the iridium complex defined by the general formula [1] are exemplified below.

KK-01
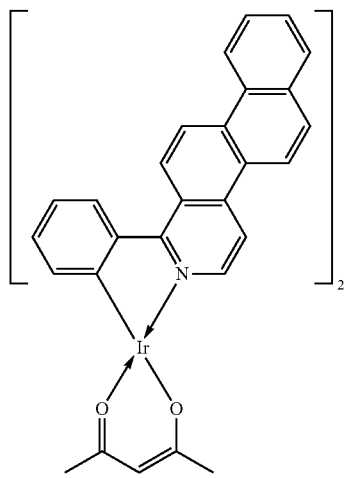

KK-02
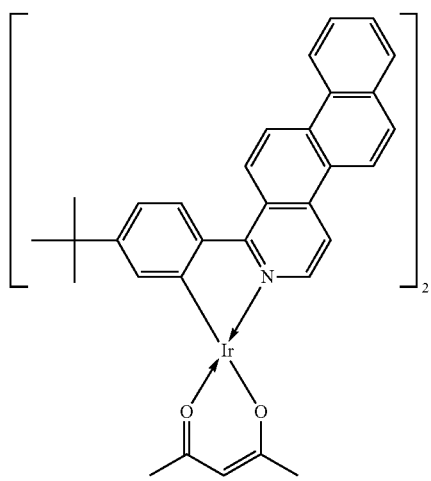

KK-03
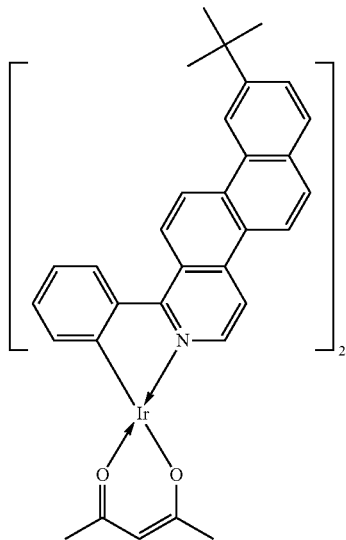

KK-04
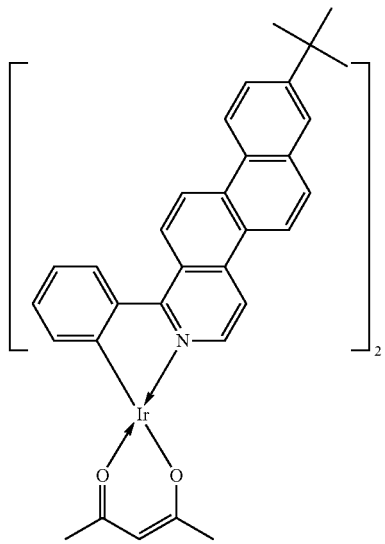

KK-05
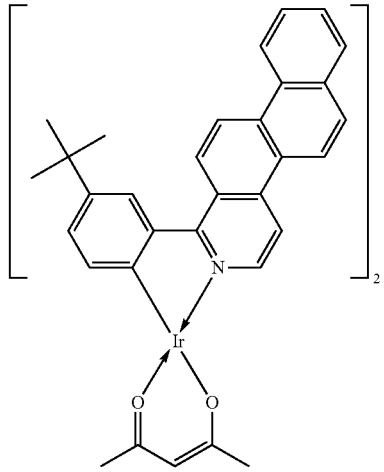

KK-06
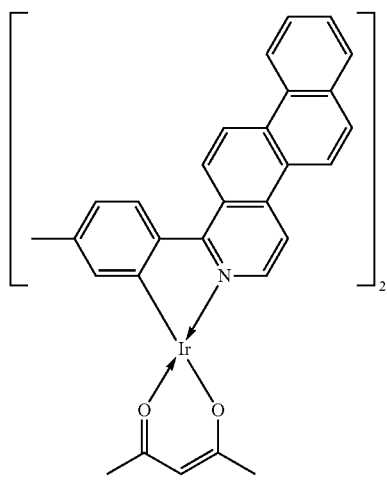
KK-09
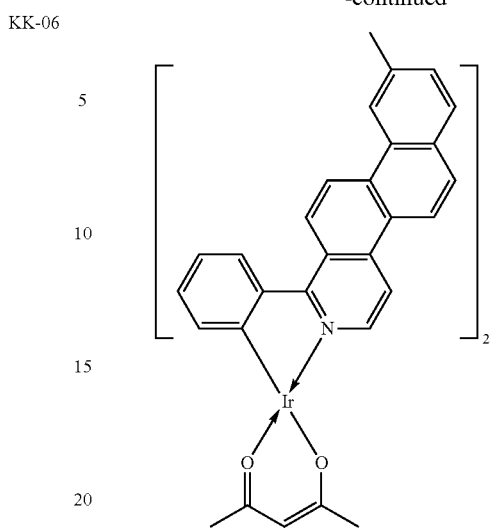
KK-07
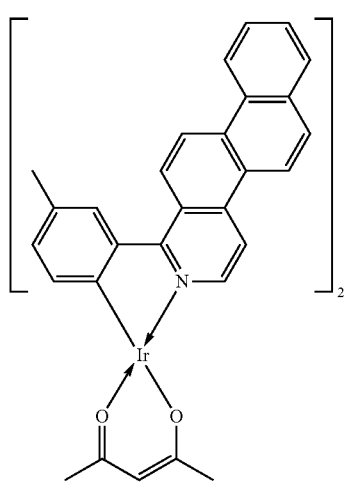
KK-10
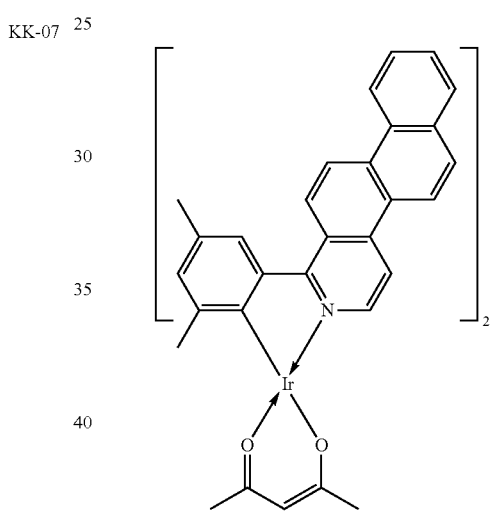
KK-08
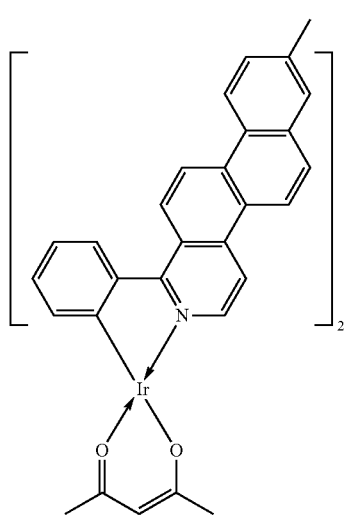
KK-11
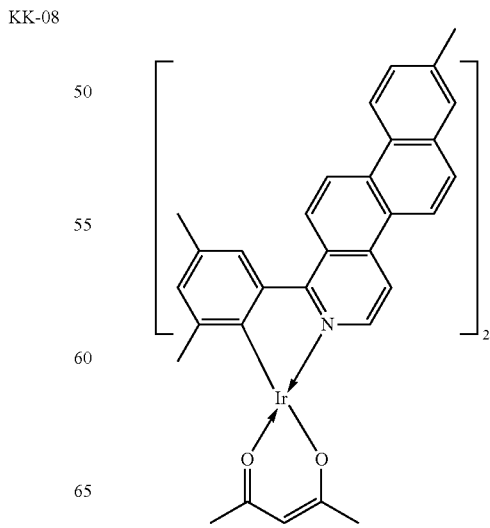

KK-12
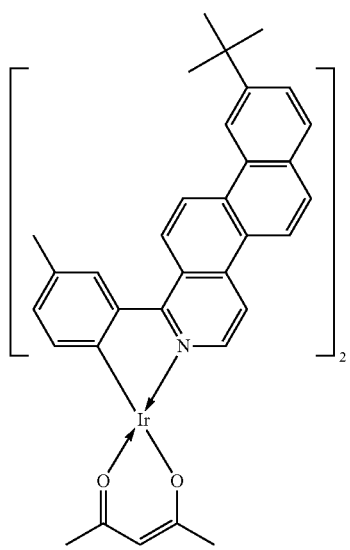
KK-15
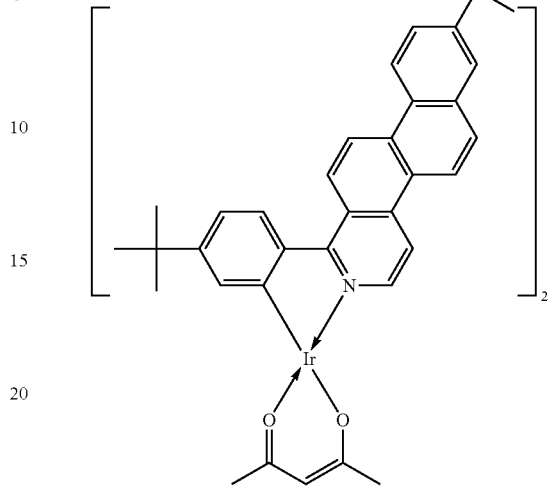
KK-13
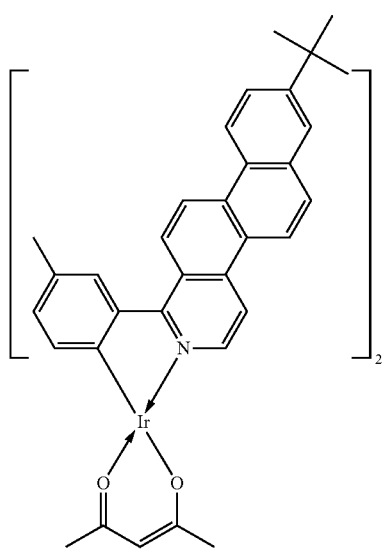
KK-16
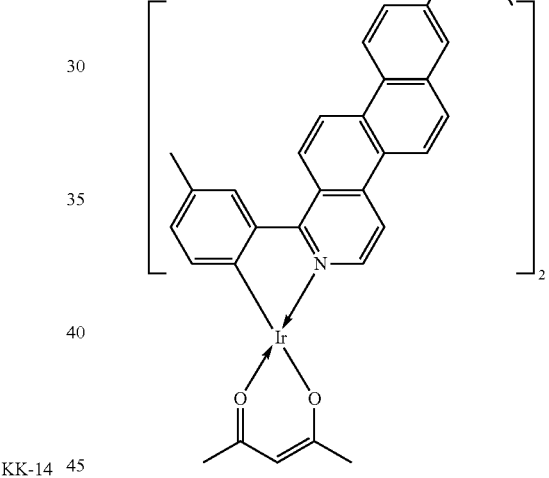
KK-14
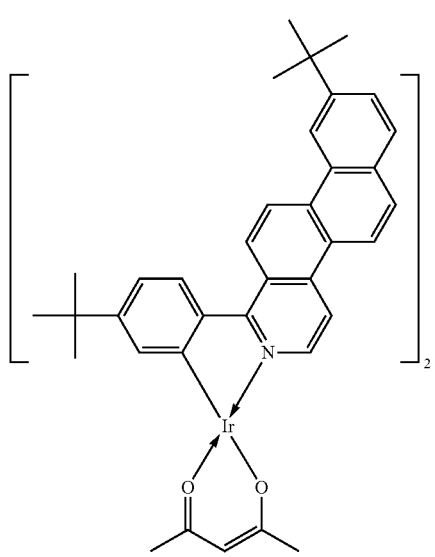
KK-17
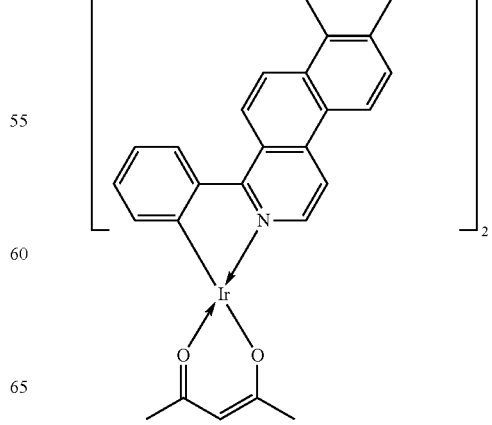

-continued
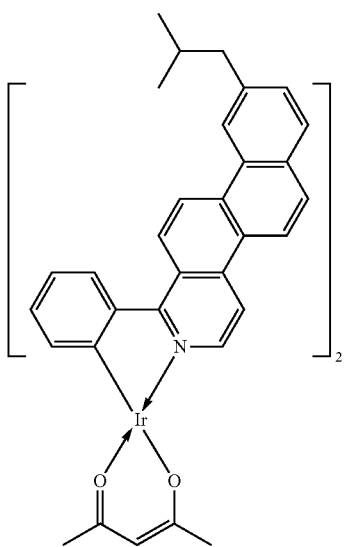
KK-18
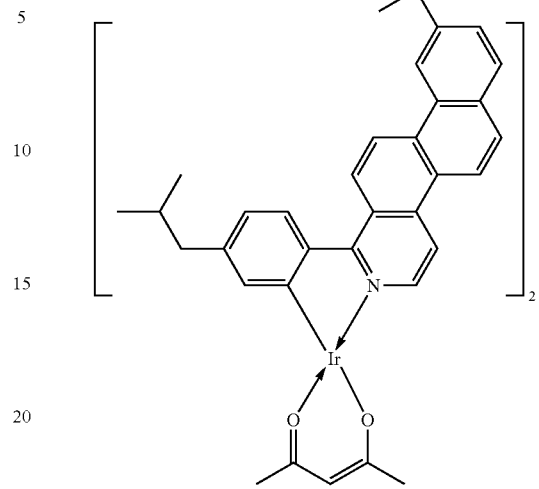
KK-21
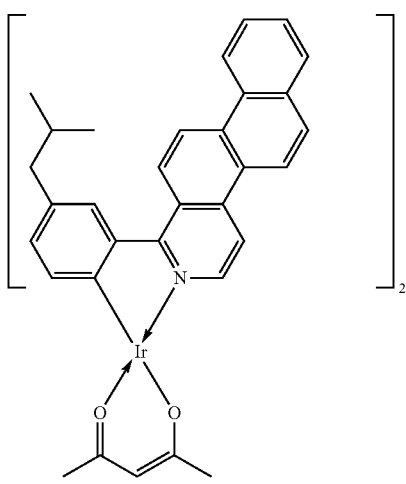
KK-19
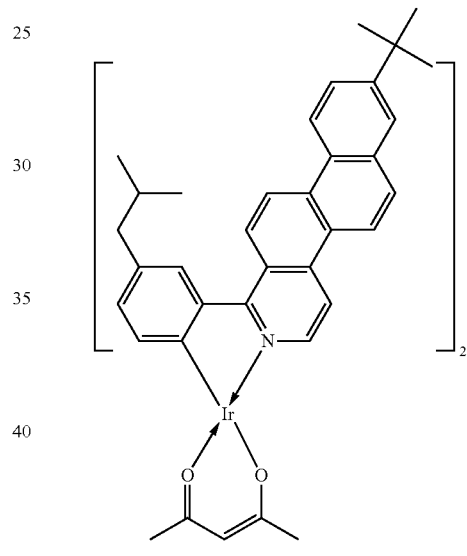
KK-22
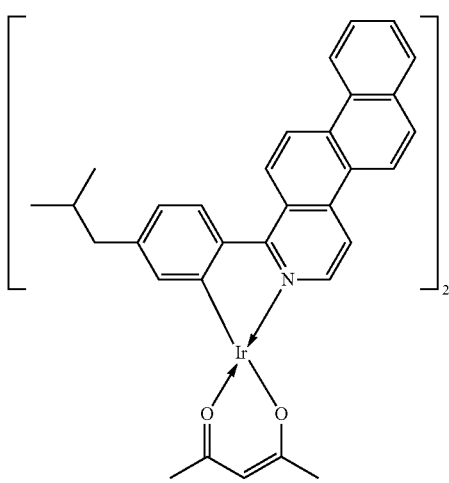
KK-20
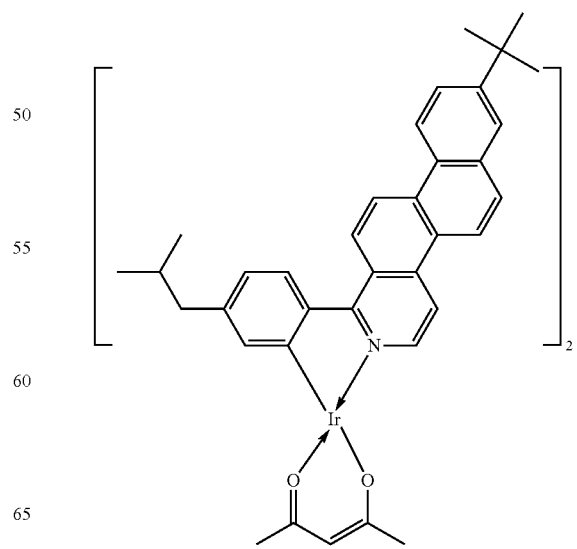
KK-23

KK-24
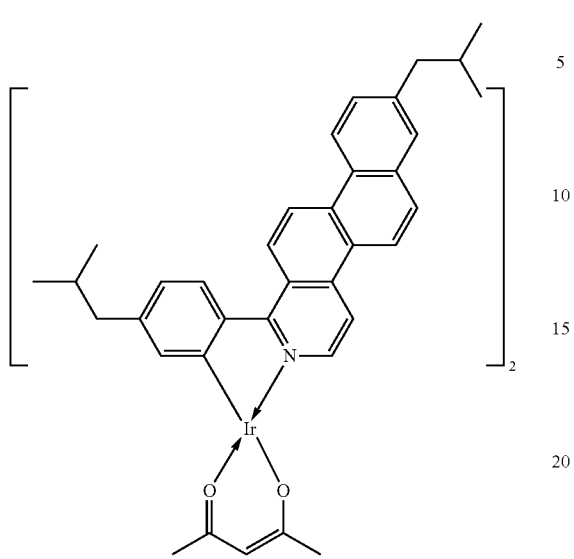
KK-25
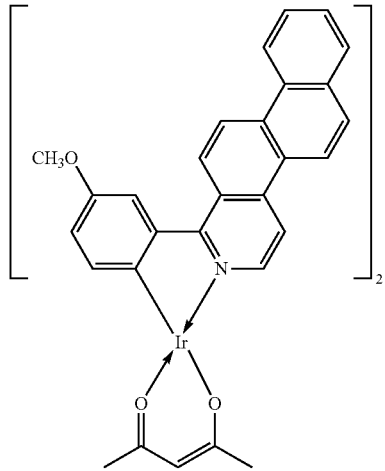
KK-26
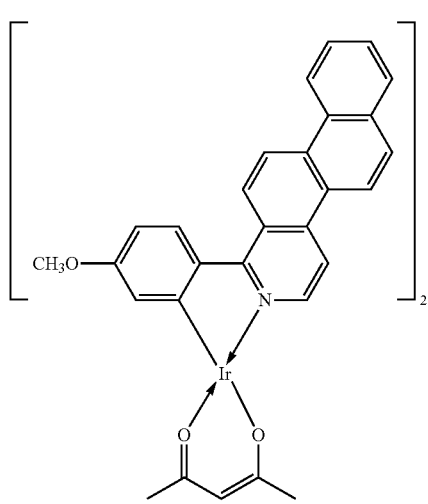
KK-27
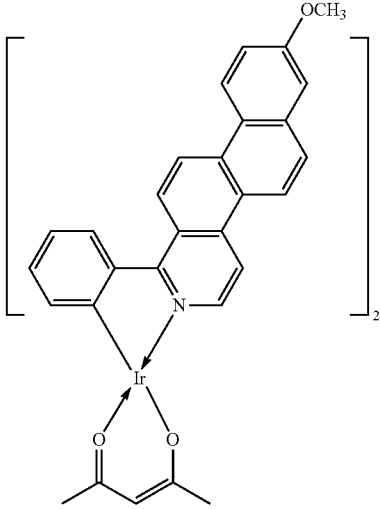
KK-28
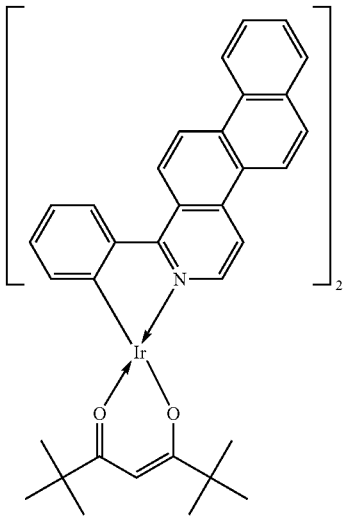
KK-29
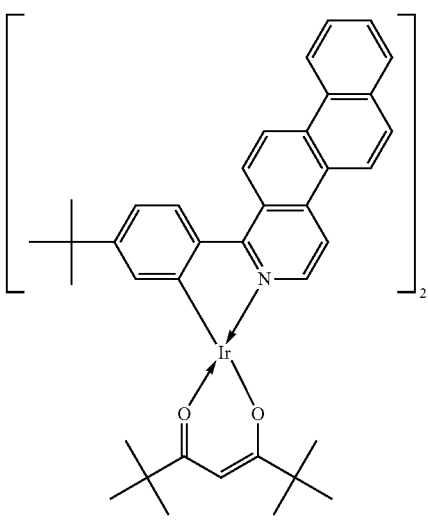

KK-30
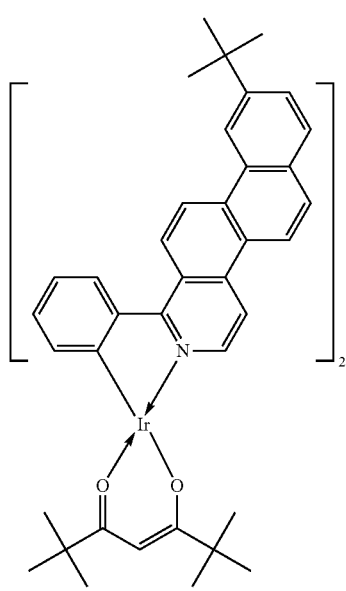
KK-31
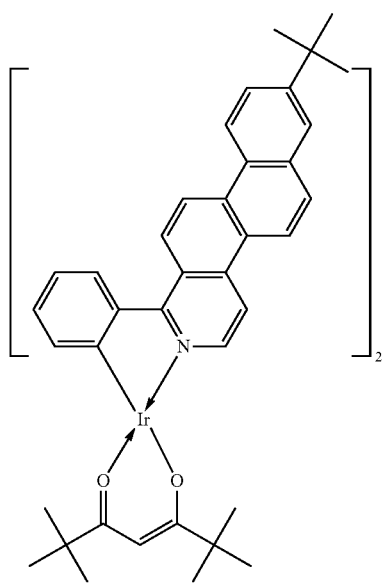
KK-32
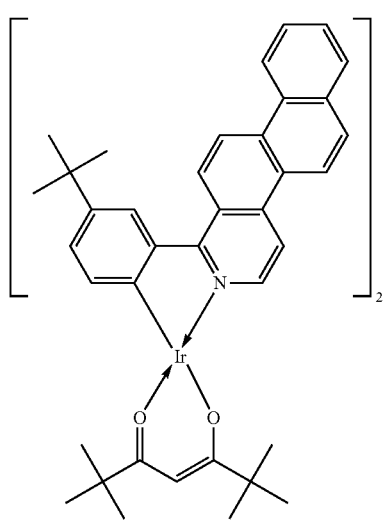
KK-33
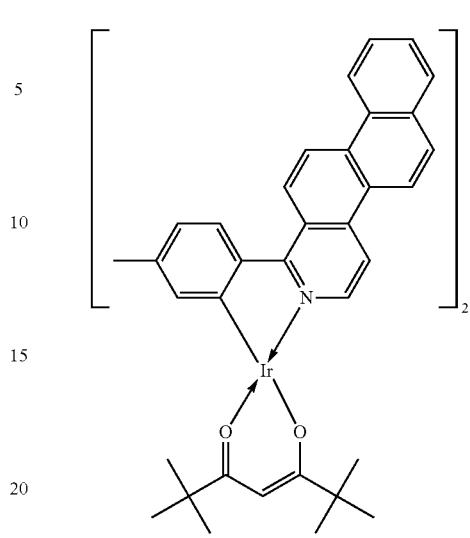
KK-34
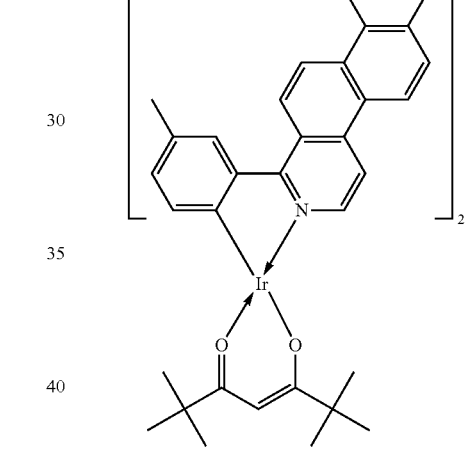
KK-35
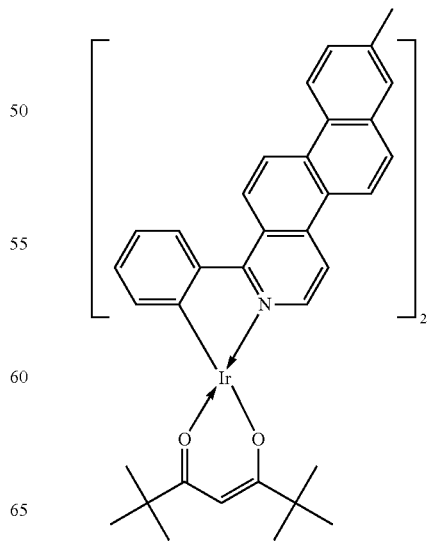

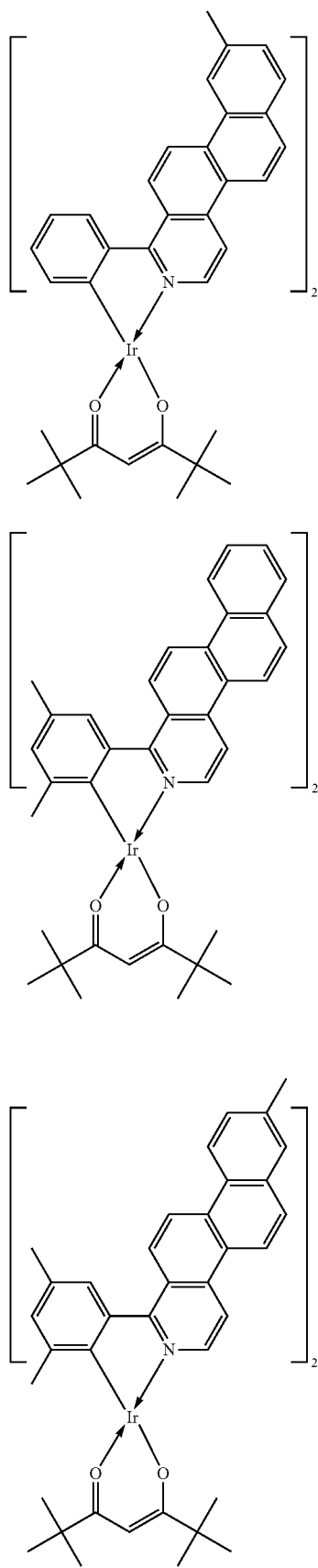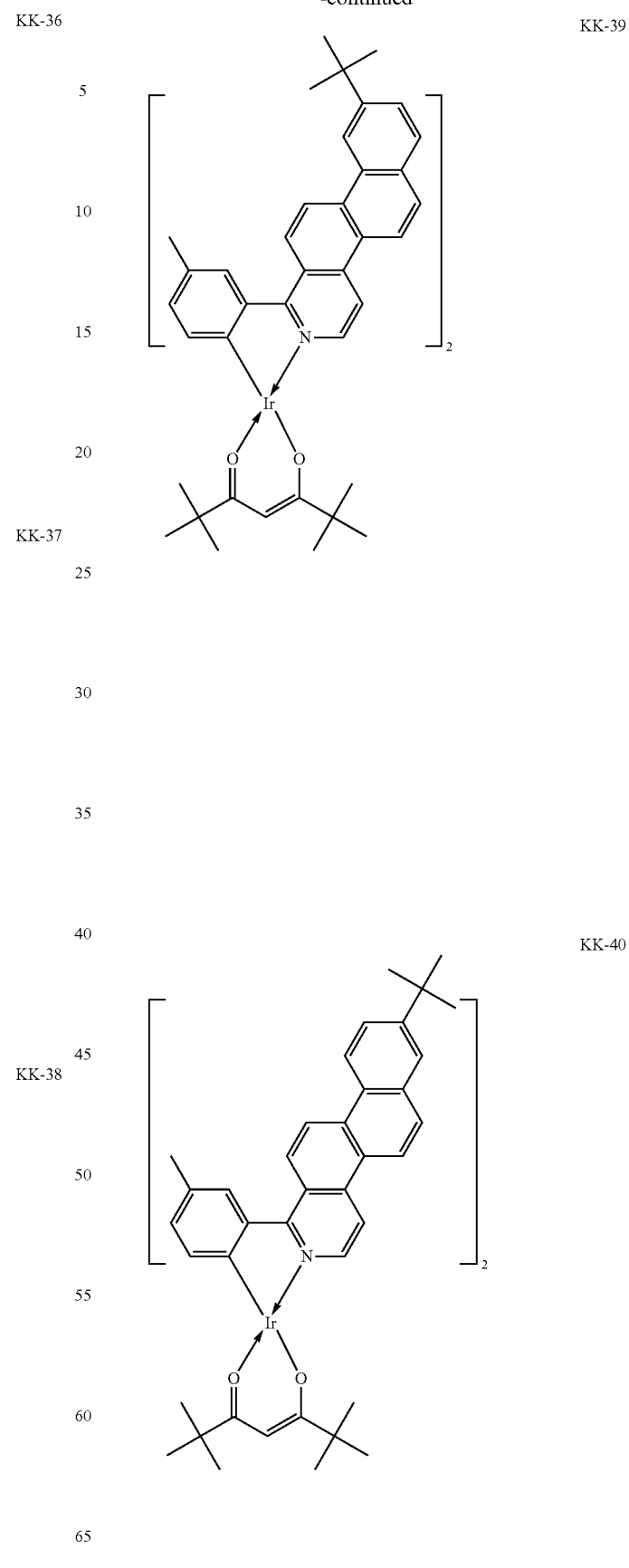

-continued
KK-41
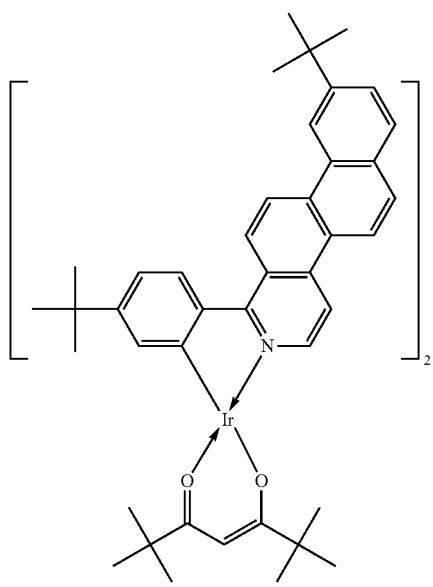
KK-42
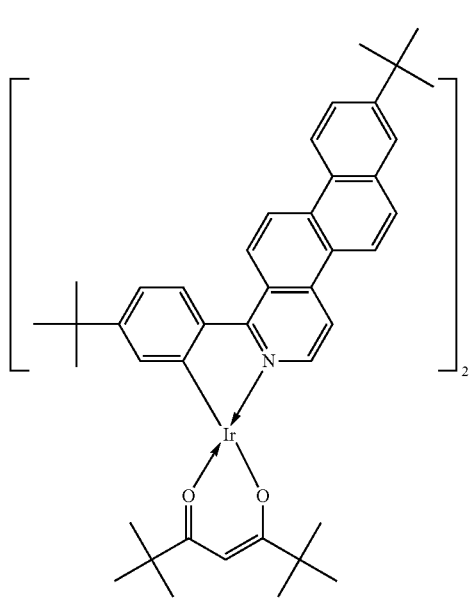
-continued
KK-43
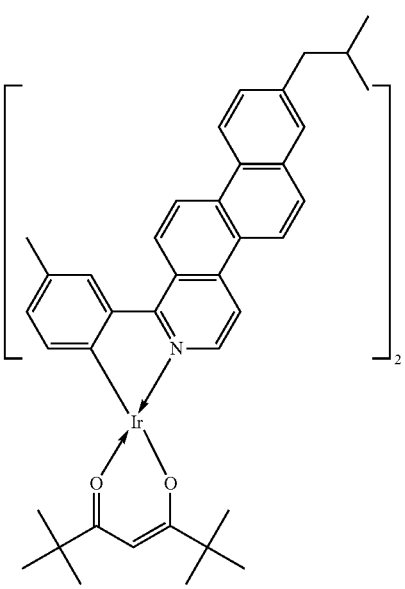
KK-44

KK-45
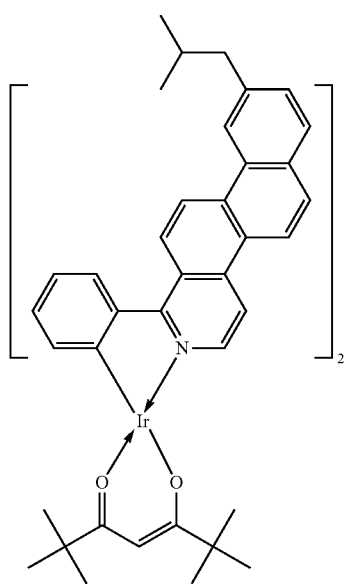
KK-46
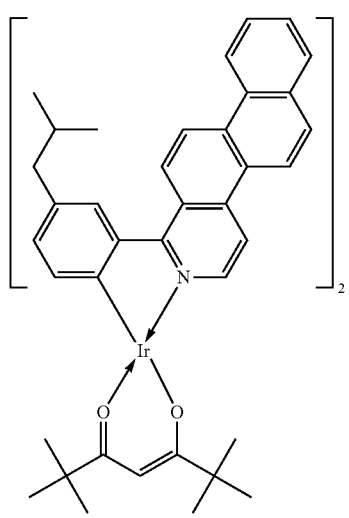
KK-47
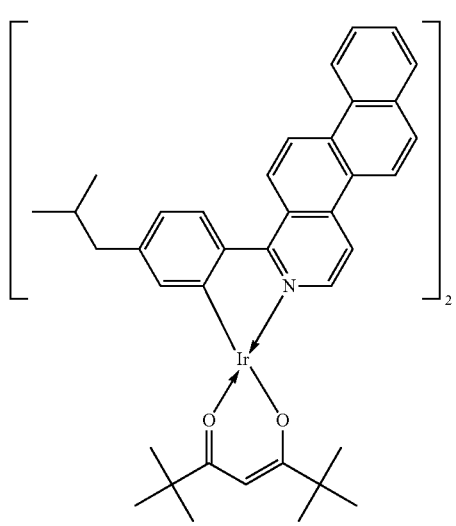
KK-48
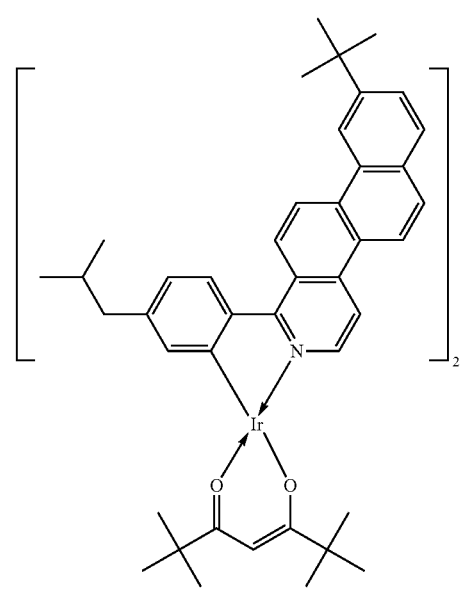
KK-49
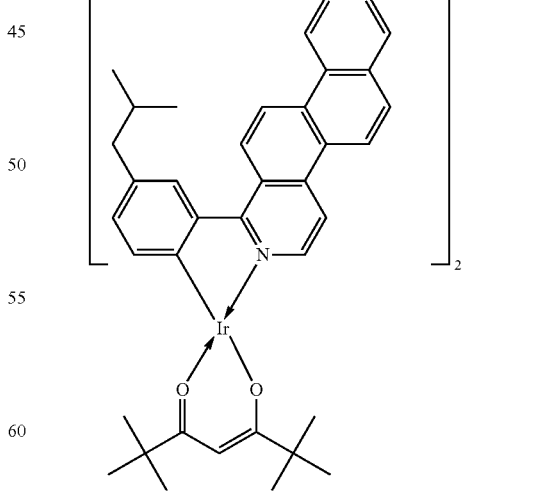

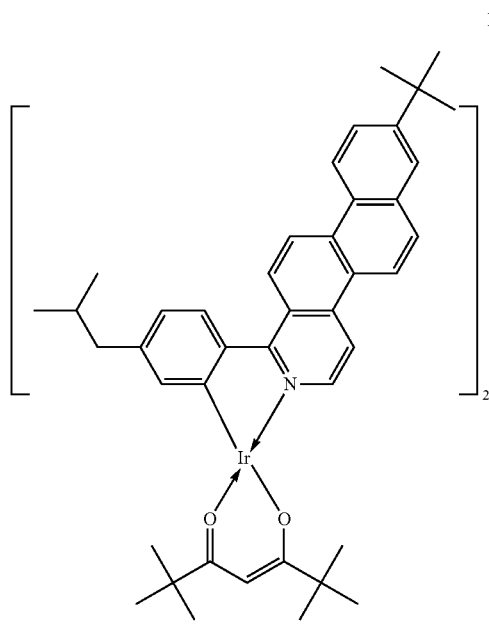
KK-50
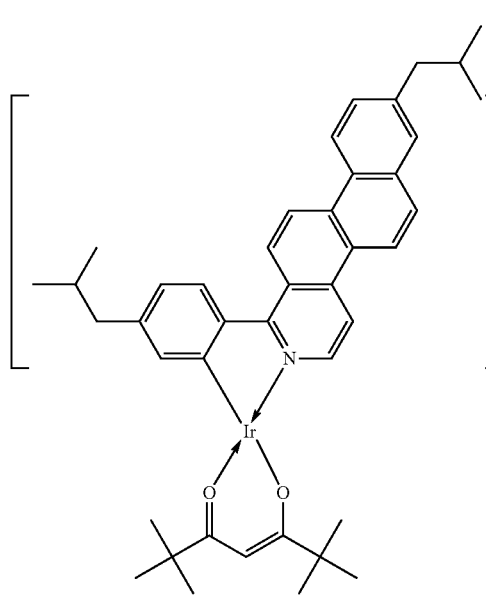
KK-51
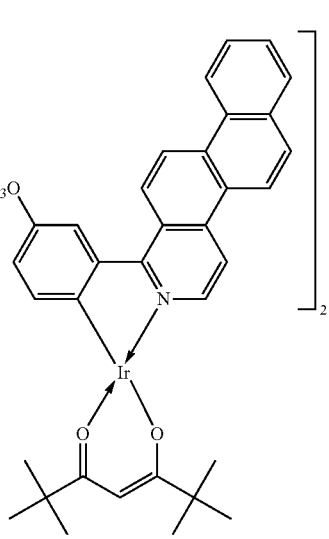
KK-52
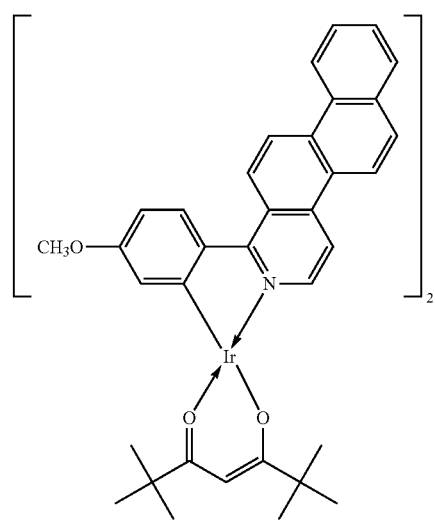
KK-53
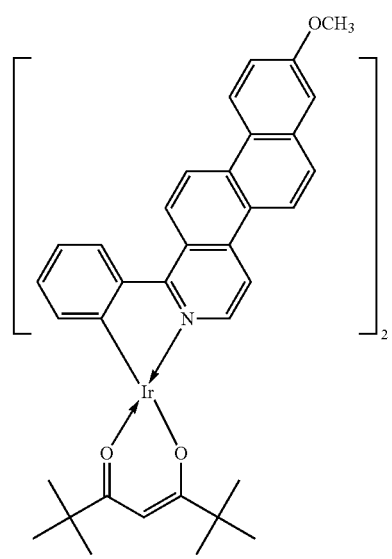
KK-54

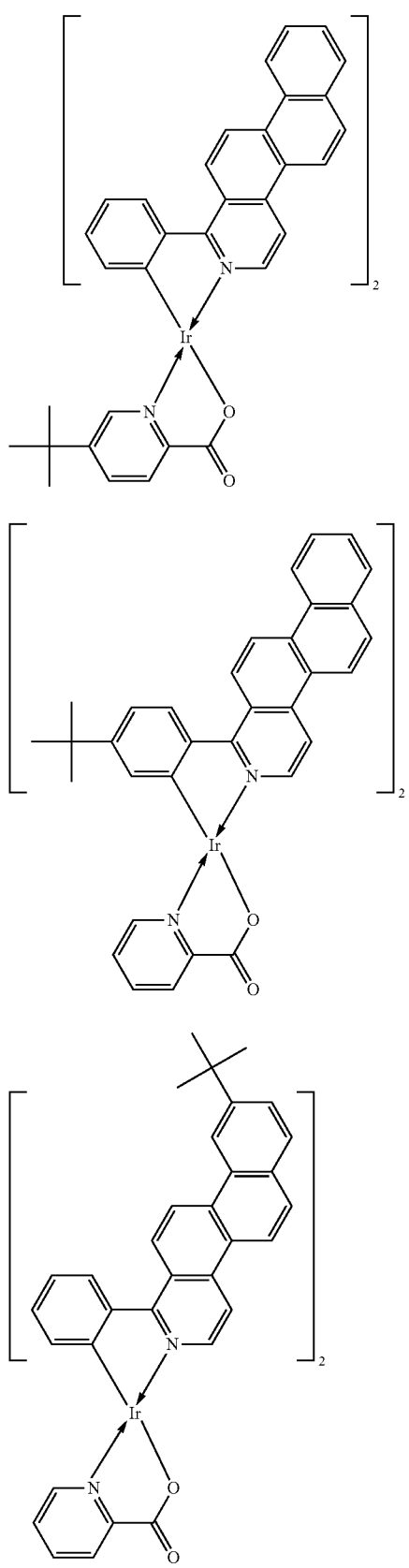
KK-55
KK-56
KK-57
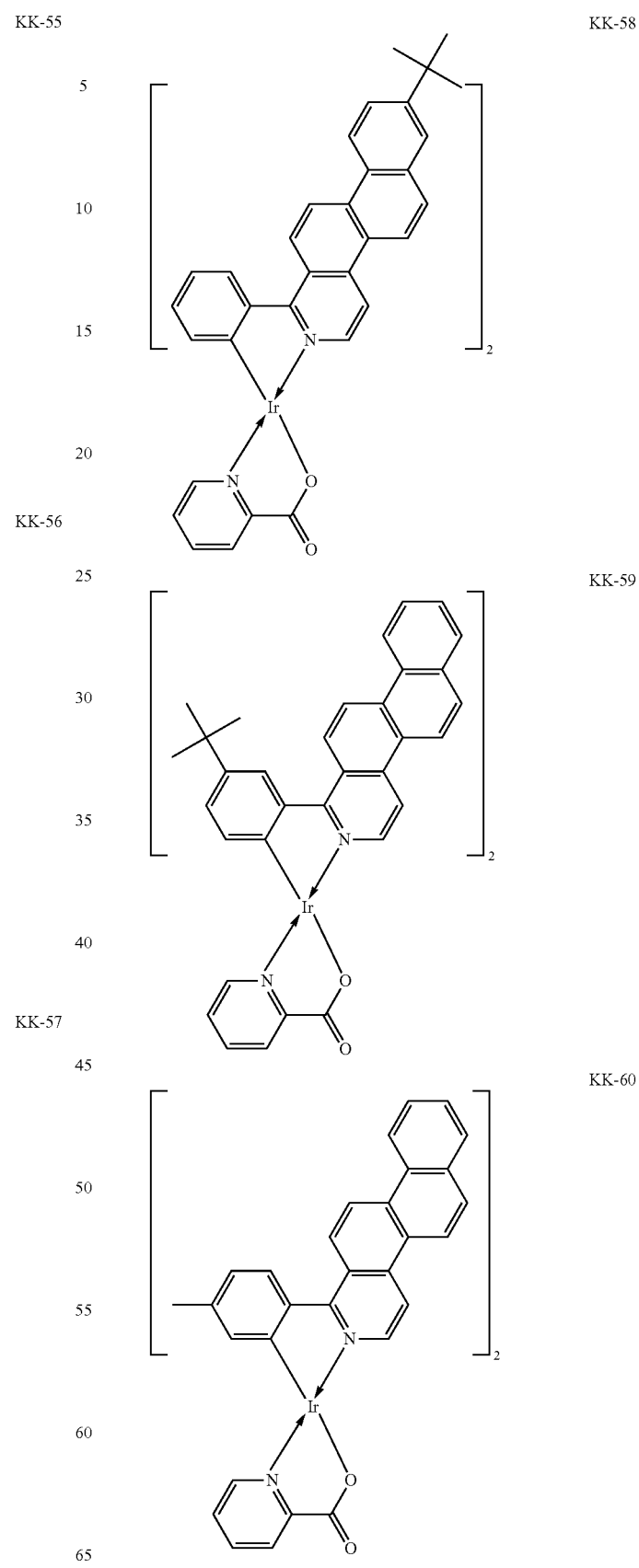
KK-58
KK-59
KK-60

KK-61
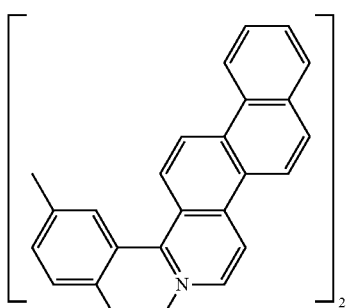
KK-62
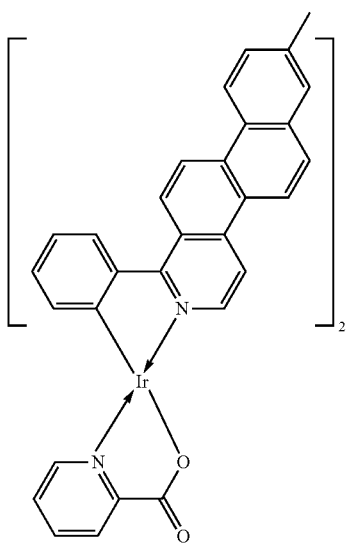
KK-63
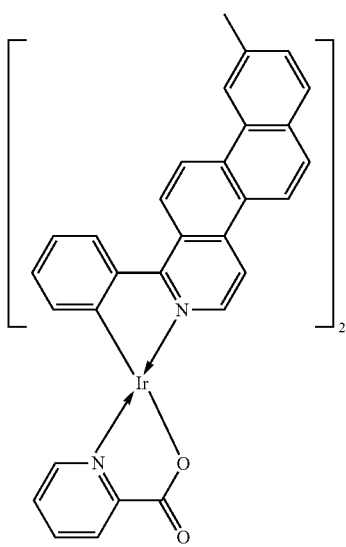
KK-64
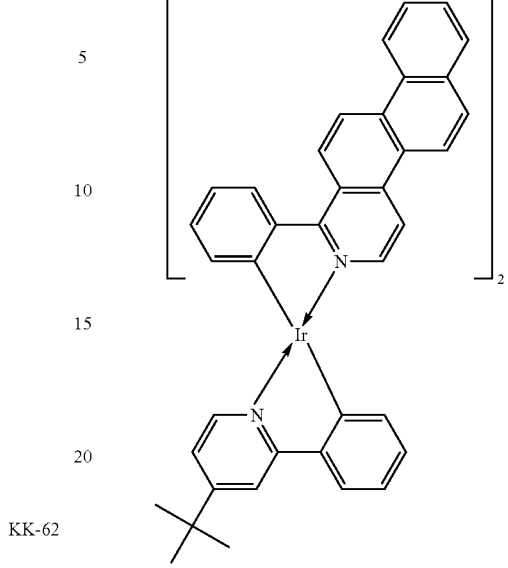
KK-65
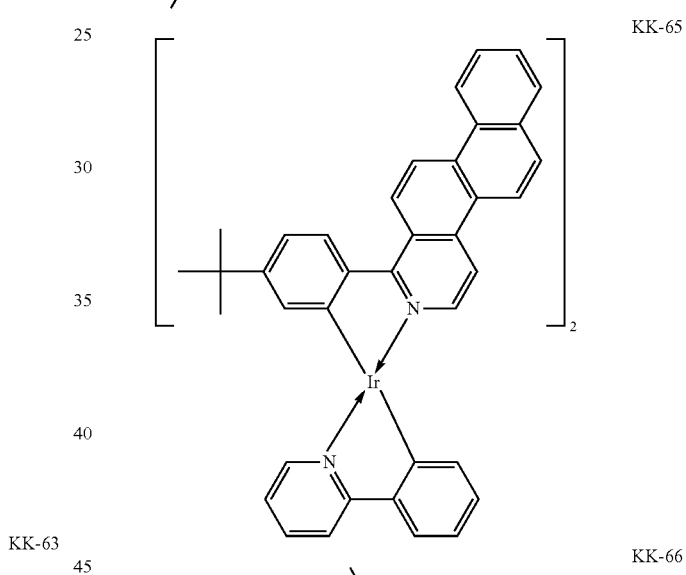
KK-66
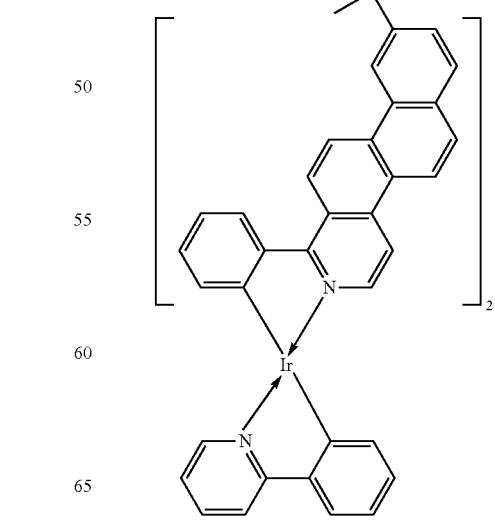

KK-67
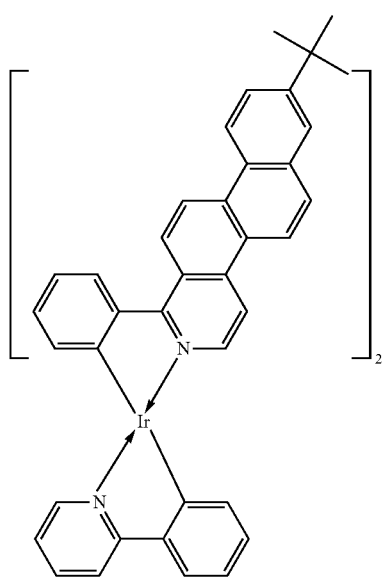
KK-68
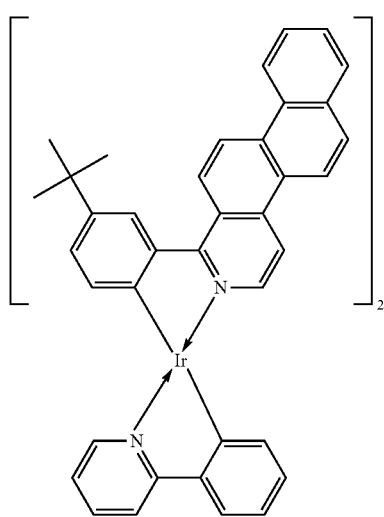
KK-69
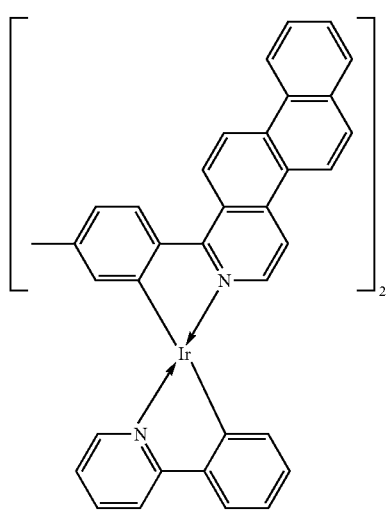
KK-70
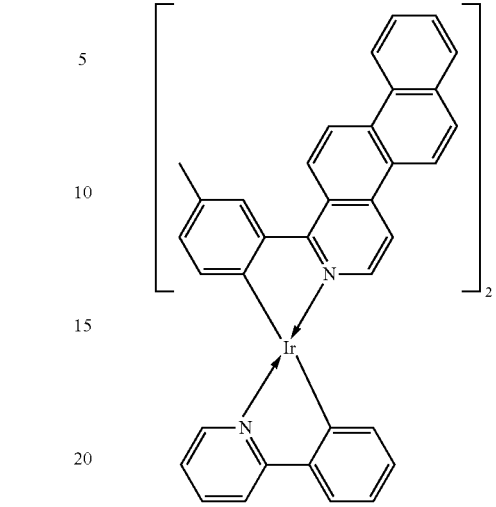
KK-71
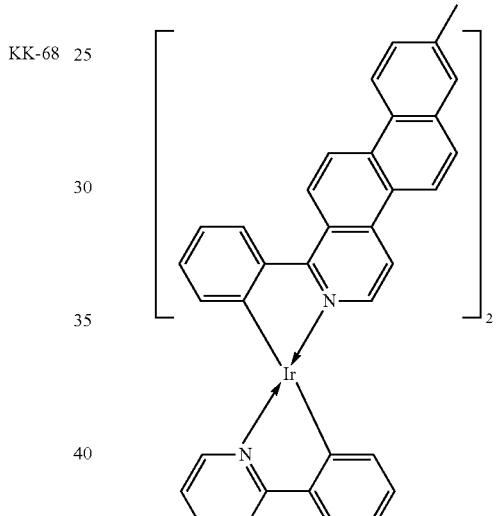
KK-72
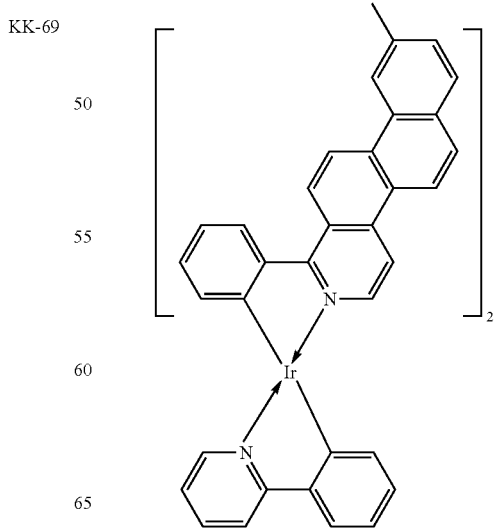

KK-73
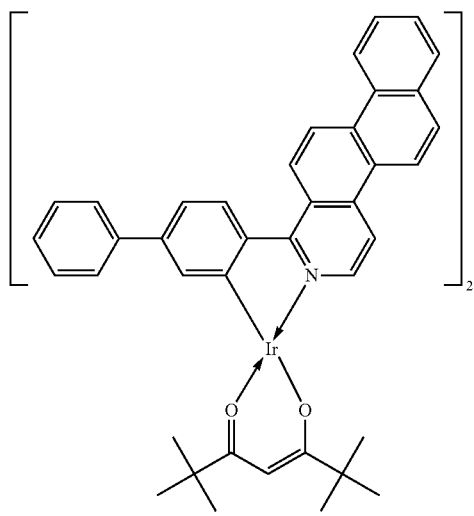
KK-76
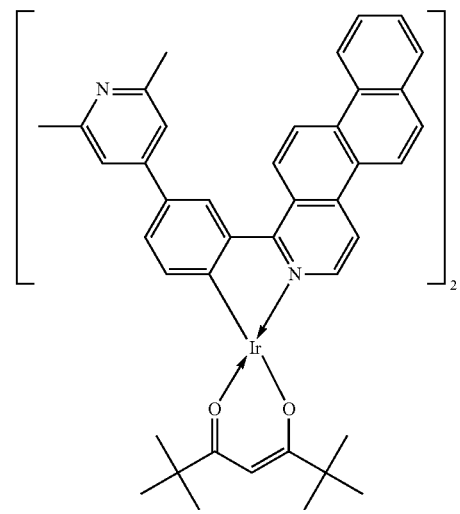
KK-74
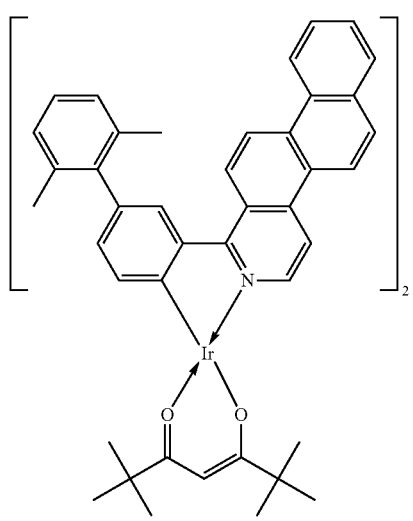
KK-77
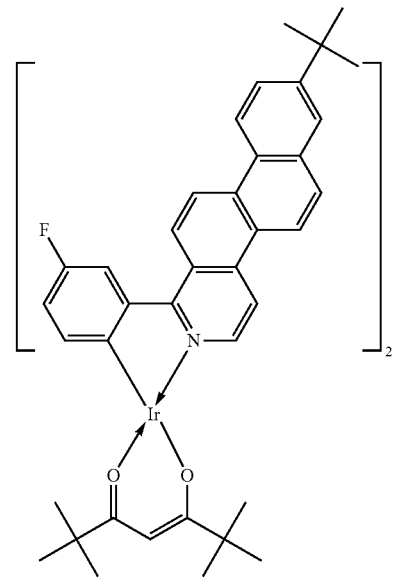
KK-75
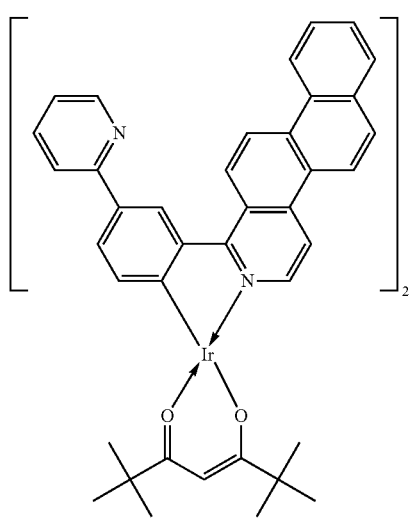
KK-78
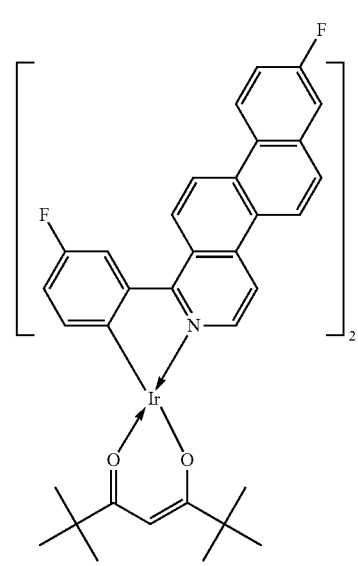

-continued
KK-79
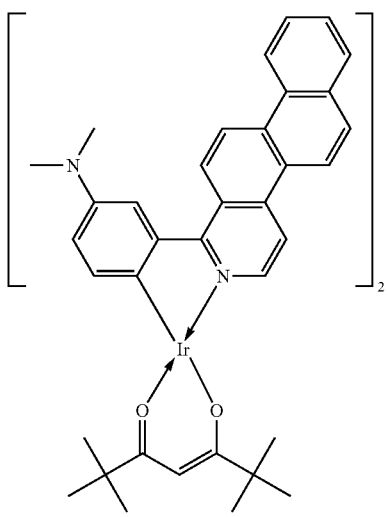
KK-80
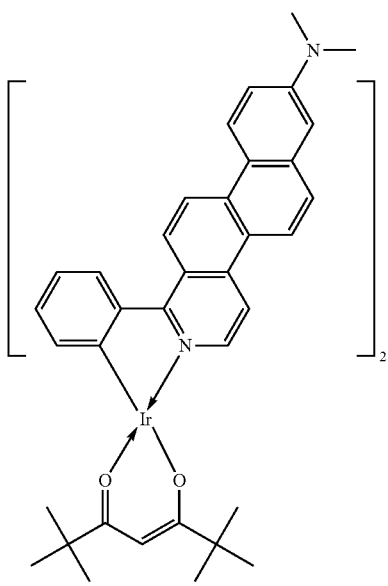
KK-81
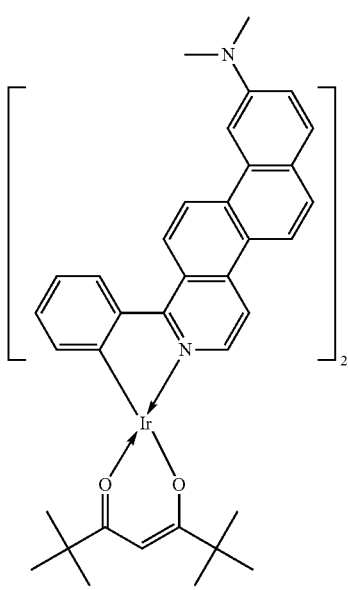
-continued
KK-82
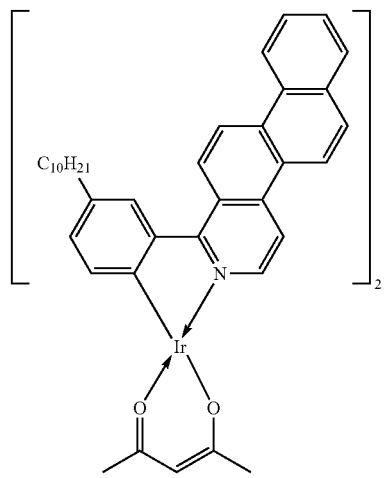
KK-83
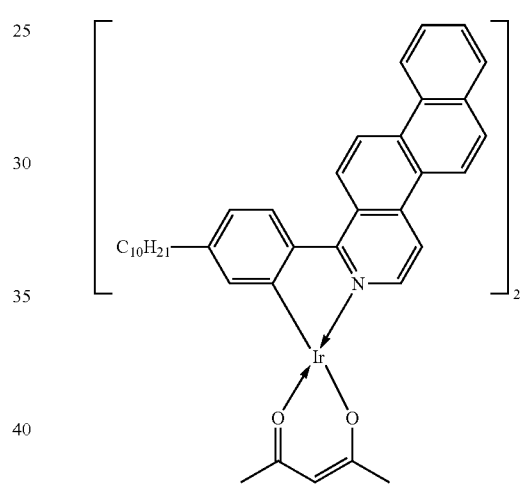
KK-84
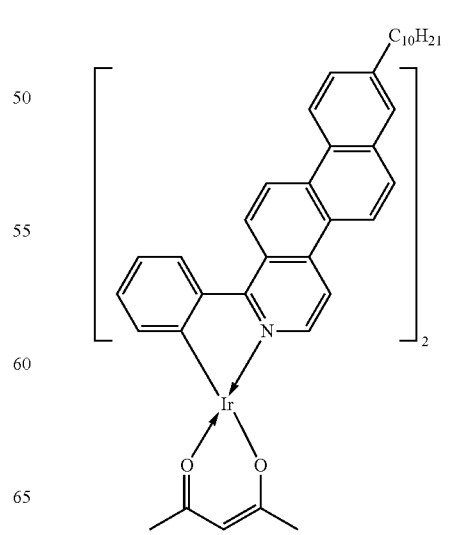

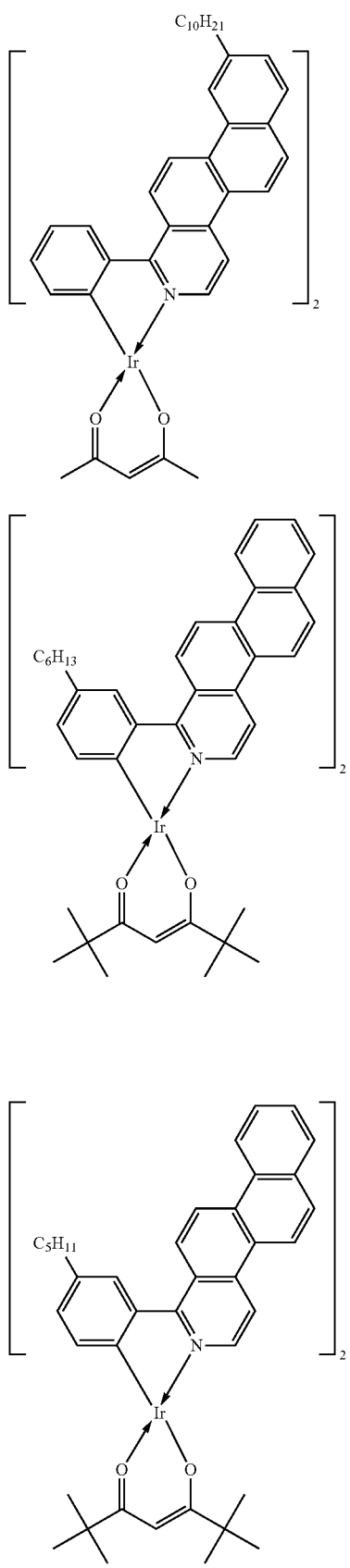

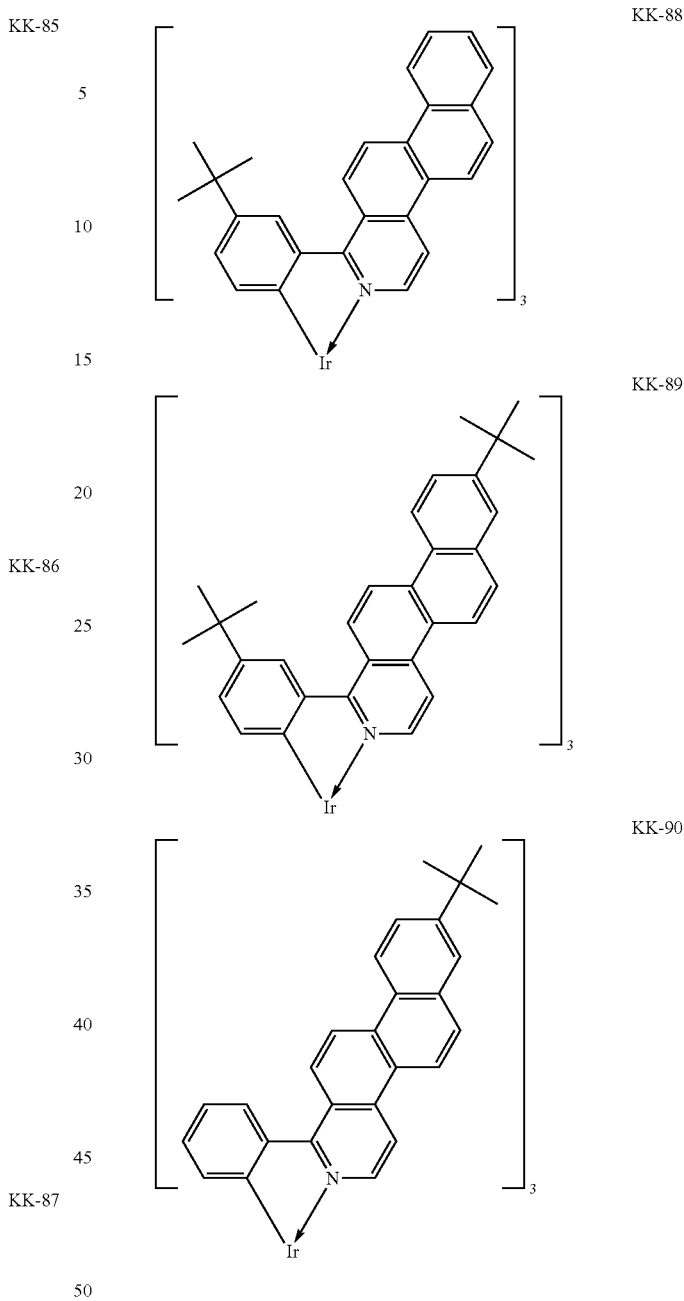

Iridium complexes in a group 1 to which Exemplified Compounds KK-01 to KK-27 correspond are each an iridium complex in which $IrX_n$ is represented by the formula [4], and at least one of $R_{27}$ and $R_{29}$ represents a methyl group out of the iridium complexes represented by the formula [1].

Those iridium complexes in the group 1 are each a complex having an extremely high emission quantum yield, and the use of the complex as a guest molecule for an emission layer provides an organic light-emitting device having high emission efficiency. Further, the iridium complexes in the group 1 are each an iridium complex formed of two ligands of a 1-phenylnaphtho[2,1-f]isoquinoline derivative and one diketone-based bidentate ligand called acetylacetone. Accordingly, the complex can be easily subjected to sublimation purification because of its relatively small molecular weight.

Iridium complexes in a group 2 to which Exemplified Compounds KK-28 to KK-54 correspond are each an iridium complex in which $IrX_n$ is represented by the formula [4], and at least one of $R_{27}$ and $R_{29}$ represents a tert-butyl group out of the iridium complexes represented by the formula [1].

Those iridium complexes in the group 2 are each a complex having an extremely high emission quantum yield, and the incorporation of the complex as a guest into an emission layer provides an organic light-emitting device having high emission efficiency. Further, the iridium complexes in the group 2 are each an iridium complex formed of two ligands of a 1-phenylnaphtho[2,1-f]isoquinoline derivative and one diketone-based bidentate ligand called dipivaloylmethane. Accordingly, the complex can be easily subjected to sublimation purification because the complex has relatively small molecular weight and dipivaloylmethane functions as a steric hindrance group. Further, the complex can be easily handled at the time of synthesis or purification because of its high solubility.

Iridium complexes in a group 3 to which Exemplified Compounds KK-55 to KK-63 correspond are each an iridium complex in which $IrX_n$ is represented by the formula [3] out of the iridium complexes represented by the formula [1].

Those iridium complexes in the group 3 are each a complex having one picolinic acid derivative as a ligand and having a shorter emission peak wavelength than that in the case where the complex has a diketone-based bidentate ligand.

Iridium complexes in a group 4 to which Exemplified Compounds KK-64 to KK-72 correspond are each an iridium complex in which $IrX_n$ is represented by the formula [2] out of the iridium complexes represented by the formula [1].

Each of those iridium complexes in the group 4 has one phenylpyridine derivative as a non-light-emitting ligand and hence provides red light emission derived from 1-phenylnaphtho[2,1-f]isoquinoline ligand. Accordingly, the complex has a small molecular weight and can be easily subjected to sublimation purification as compared to a homoleptic iridium complex using 1-phenylnaphtho[2,1-f]isoquinoline as a ligand, and the complex can provide an organic light-emitting device having a long lifetime comparable to that provided by the homoleptic iridium complex.

Iridium complexes in a group 5 to which Exemplified Compounds KK-73 to KK-76 correspond are each an iridium complex in which $IrX_n$ is represented by the formula [4] out of the iridium complexes represented by the formula [1].

Those iridium complexes in the group 5 are each a complex having an extremely high emission quantum yield, and the incorporation of the complex as a guest into an emission layer provides an organic light-emitting device having high emission efficiency.

In addition, the iridium complexes in the group 5 are each an iridium complex obtained by introducing a substituted or unsubstituted aryl group such as a phenyl group, or a substituted or unsubstituted heterocyclic group into a ligand formed of a 1-phenylnaphtho[2,1-f]isoquinoline derivative. Accordingly, the complex can be easily subjected to sublimation purification because the aryl group or the heterocyclic group functions as a substituent that induces steric hindrance.

Iridium complexes in a group 6 to which Exemplified Compounds KK-77 and KK-78 correspond are each an iridium complex in which $IrX_n$ is represented by the formula [4] out of the iridium complexes represented by the formula [1].

Those iridium complexes corresponding to the group 6 are each a complex having an extremely high emission quantum yield, and the incorporation of the complex as a guest into an emission layer provides an organic light-emitting device having high emission efficiency. Further, the iridium complexes in the group 6 are each an iridium complex in which a ligand is substituted with a fluorine atom. Accordingly, the complex can be easily subjected to sublimation purification not only because of a steric hindrance group of an alkyl group but also because of the occurrence of repulsion between light-emitting ligands. In addition, the complex can cause the device to emit light without reducing its emission efficiency even when the complex is doped at a concentration as high as 5 wt % or more with respect to a matrix.

Iridium complexes in a group 7 to which Exemplified Compounds KK-79 to KK-81 correspond are each an iridium complex in which $IrX_n$ is represented by the formula [4] out of the iridium complexes represented by the formula [1].

Those iridium complexes in the group 7 are each a complex having an extremely high emission quantum yield, and the use of the complex as a guest for an emission layer provides an organic light-emitting device having high emission efficiency. Further, the iridium complexes in the group 7 are each an iridium complex in which a ligand has a substituted amino group. Accordingly, the HOMO level of the compound is shallow (close to a vacuum level) and its combination with a host material (host molecule) having a shallow HOMO level can reduce a charge barrier, whereby low-voltage driving of the device is realized. In addition, the complex can be easily subjected to sublimation purification because the substituted amino group functions as a steric hindrance group as well.

Iridium complexes in a group 8 to which Exemplified Compounds KK-82 to KK-87 correspond are each an iridium complex in which $IrX_n$ is represented by the formula [4] out of the iridium complexes represented by the formula [1].

Those iridium complexes in the group 8 are each a complex having an extremely high emission quantum yield, and the use of the complex as a guest (for an emission layer) provides an organic light-emitting device having high emission efficiency. Further, the iridium complexes in the group 8 are each an iridium complex having a long-chain alkyl group as a substituent. Accordingly, the complex has so high solubility as to be capable of being easily formed into a film by application such as a wet method.

Iridium complexes in a group 9 to which Exemplified Compounds KK-88 to KK-90 correspond are each an iridium complex in which m represents 3 and n represents 0 out of the iridium complexes represented by the formula [1]. In each of those iridium complexes in the group 9, all three ligands are 1-phenylnaphtho[2,1-f]isoquinoline ligands, and hence the stability of the complex is extremely high. Therefore, the incorporation of the complex as a guest into an emission layer provides an organic light-emitting device having high driving durability and a long lifetime.

(6) Specific Examples of Metal Complex

Specific structural formulae of the metal complex compound to be used as the host are exemplified below.

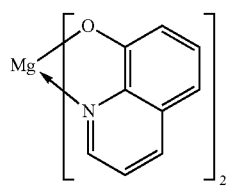 H101
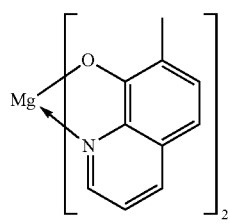 H102
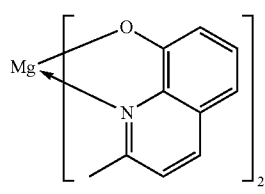 H103
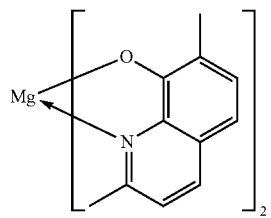 H104
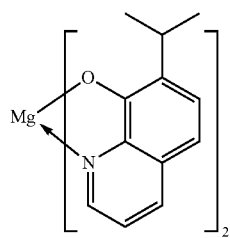 H105
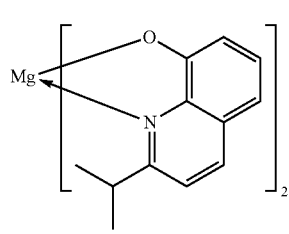 H106
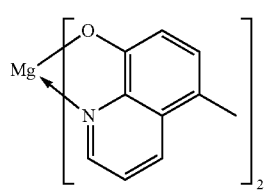 H107
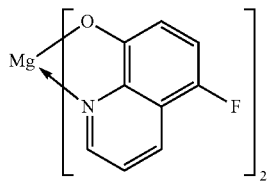 H108
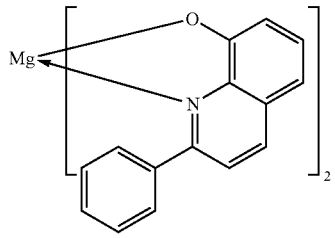 H109
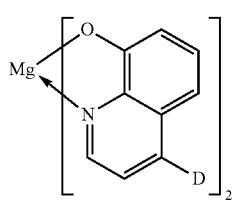 H110
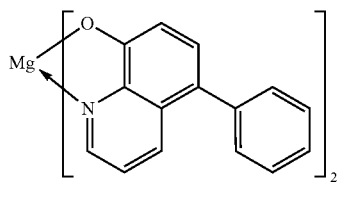 H111
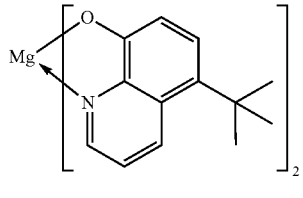 H112
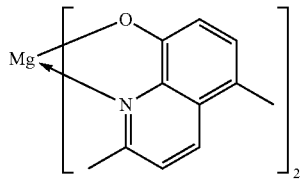 H113
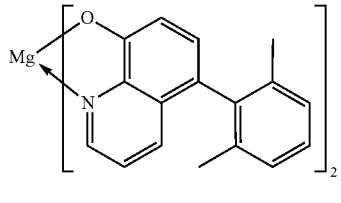 H114
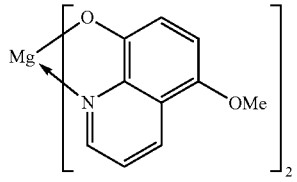 H115

H116 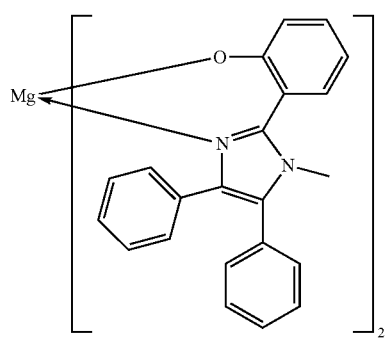
H117 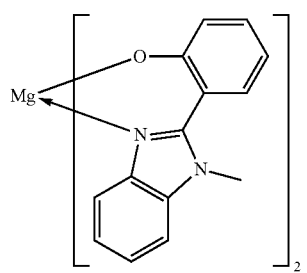
H118 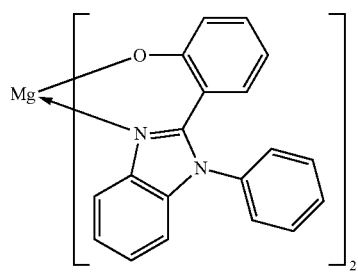
H119 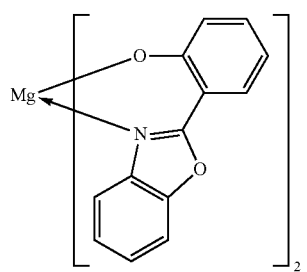
H120 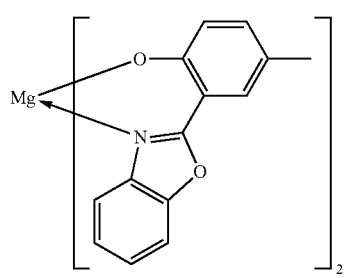
H121 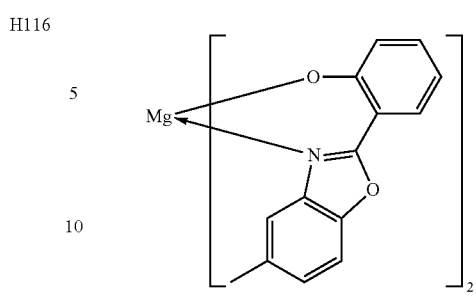
H122 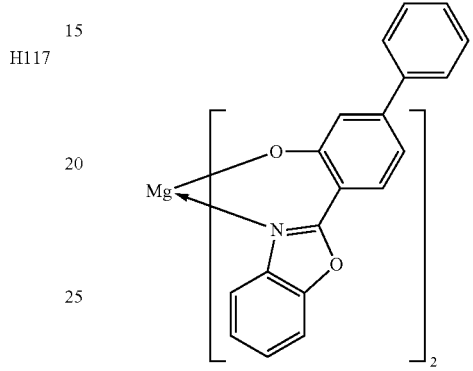
H123 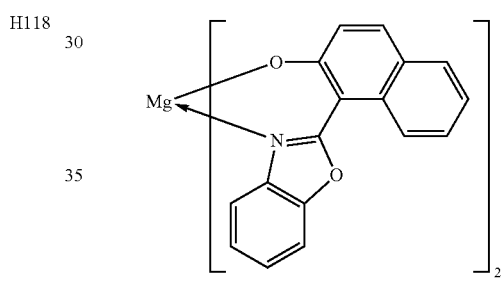
H124 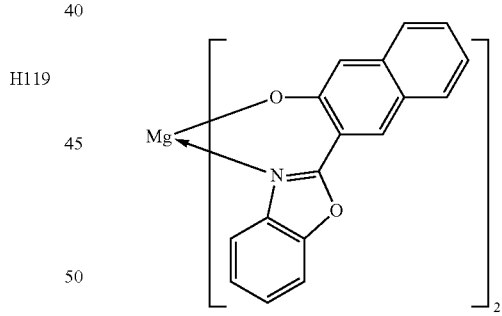
H125 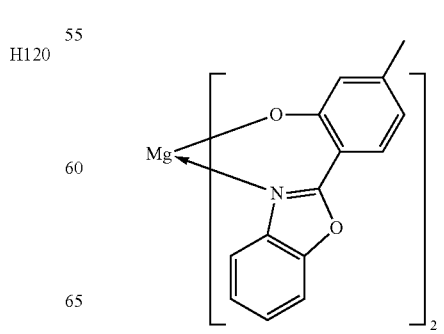

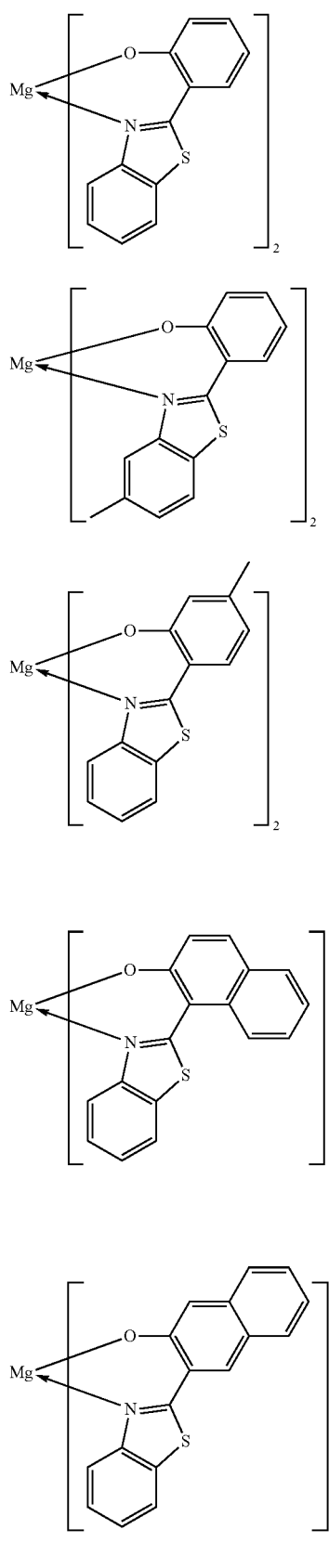
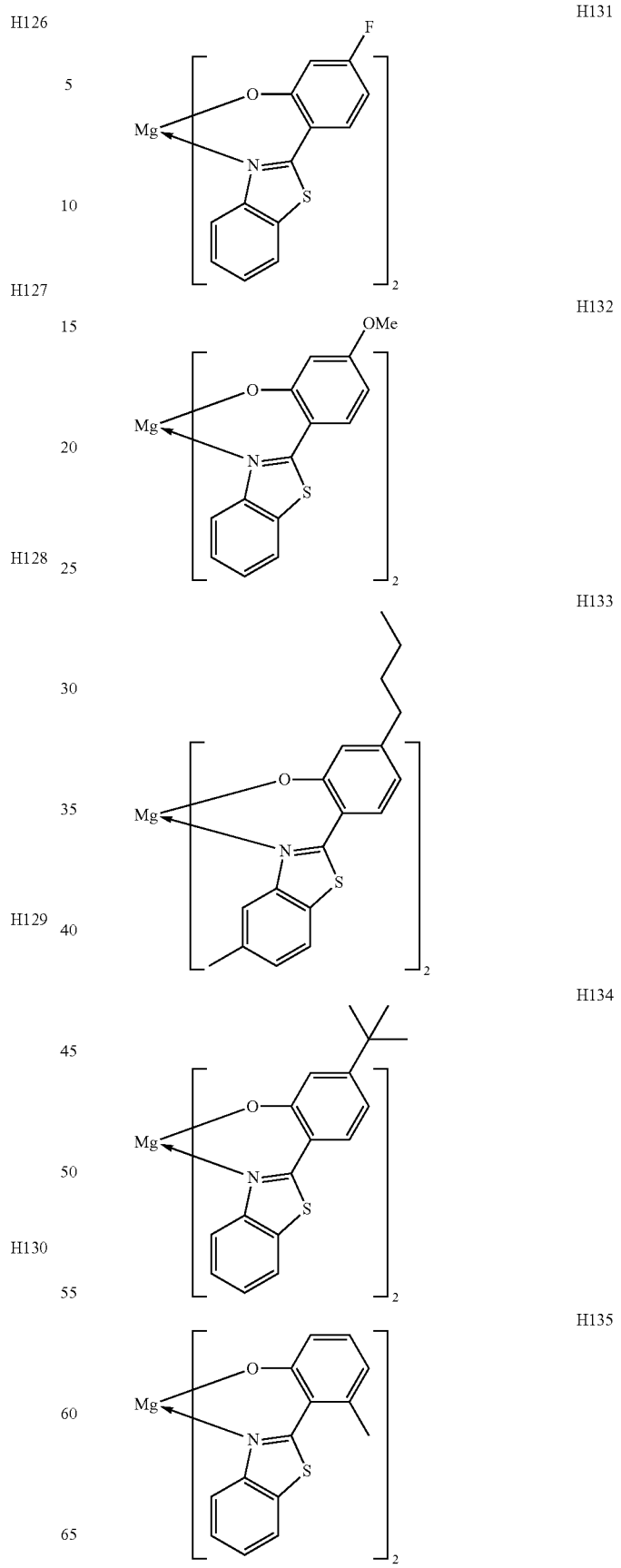

-continued
H136
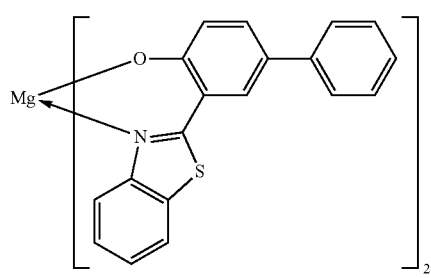
H201
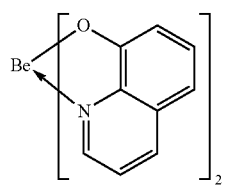
H202
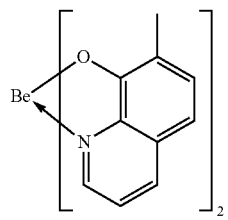
H203
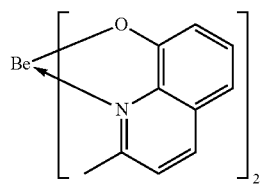
H204
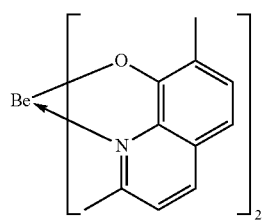
H205
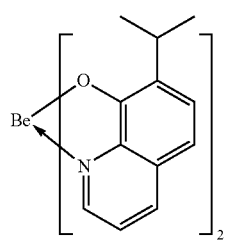
H206
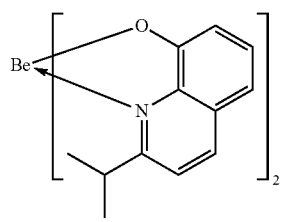
-continued
H207
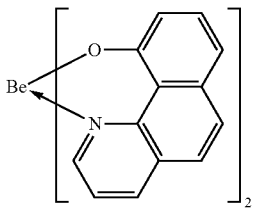
H208
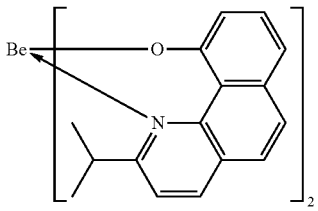
H209
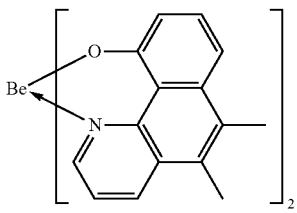
H210
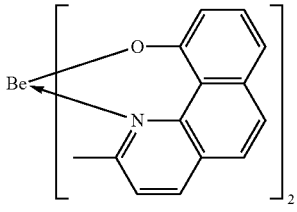
H211
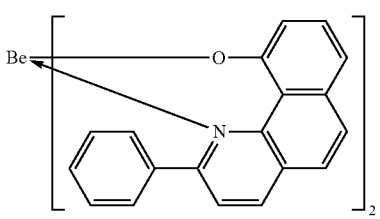
H212
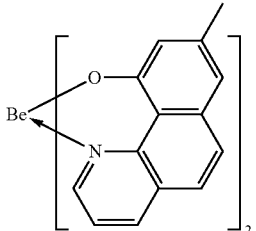
H213
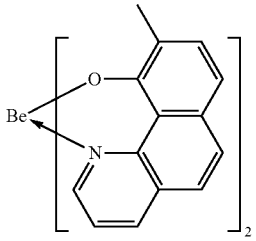

H214
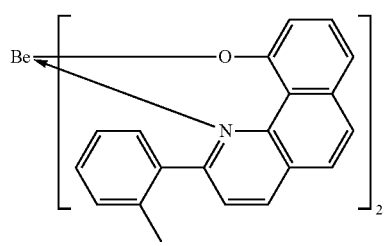
H215
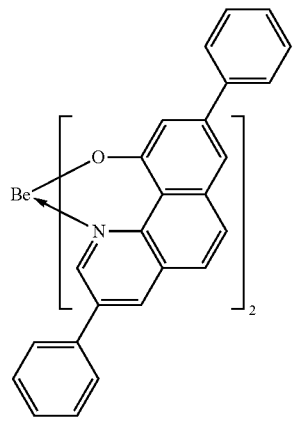
H216
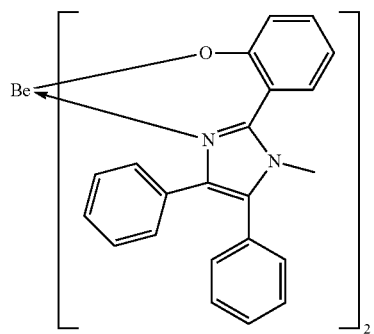
H217
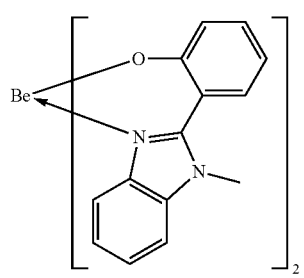
H218
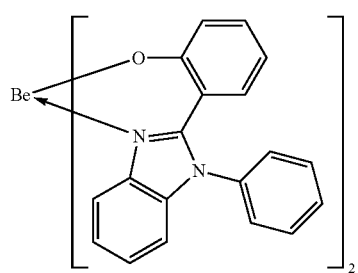
H219
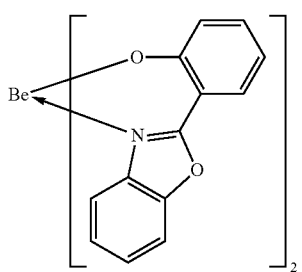
H220
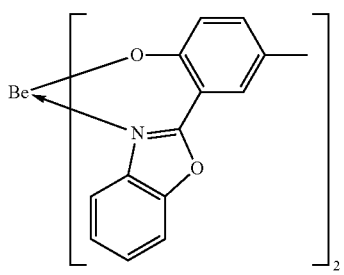
H221
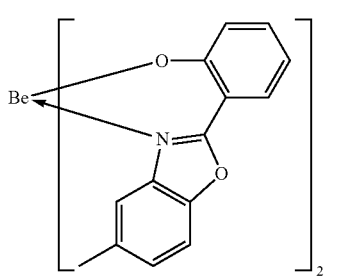
H222
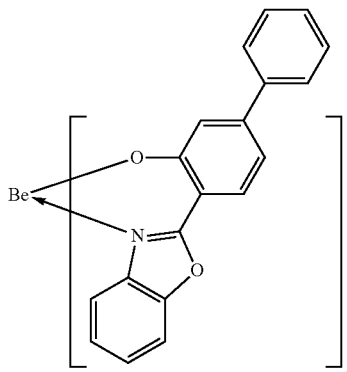
H223
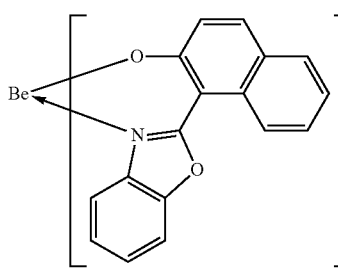

-continued
H224
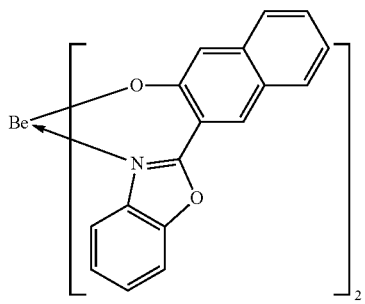
H225
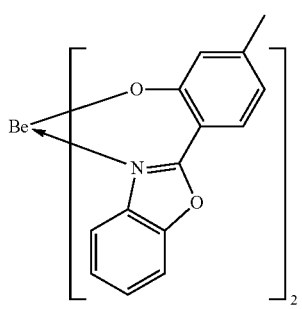
H226
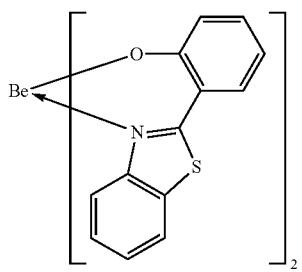
H227
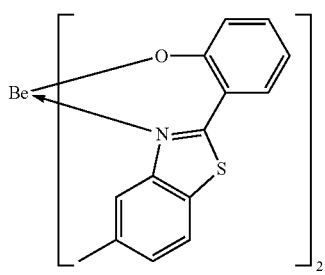
H228
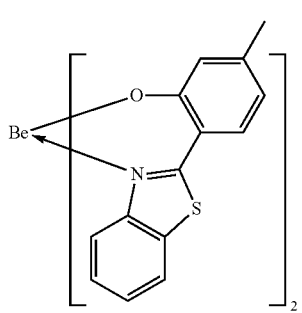
-continued
H229
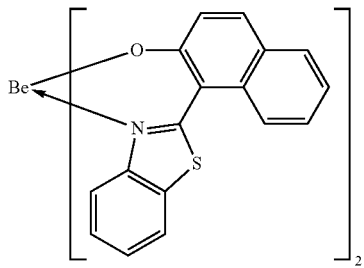
H230
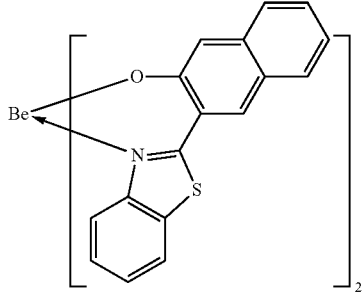
H231
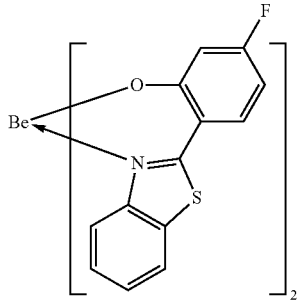
H232
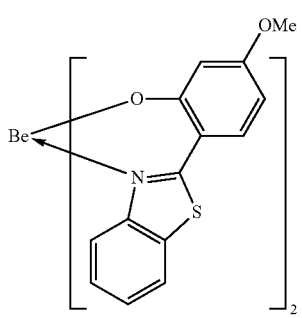
H233
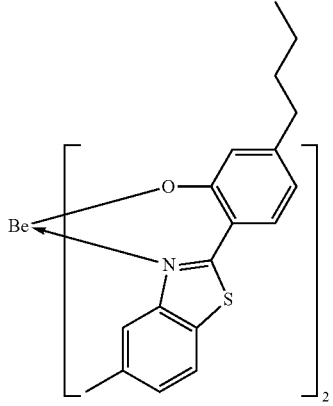

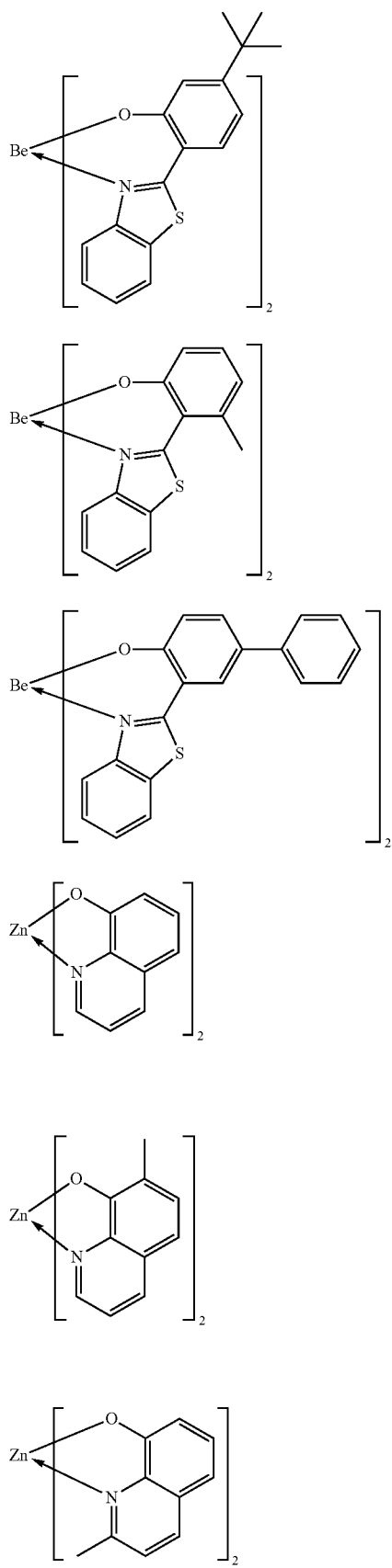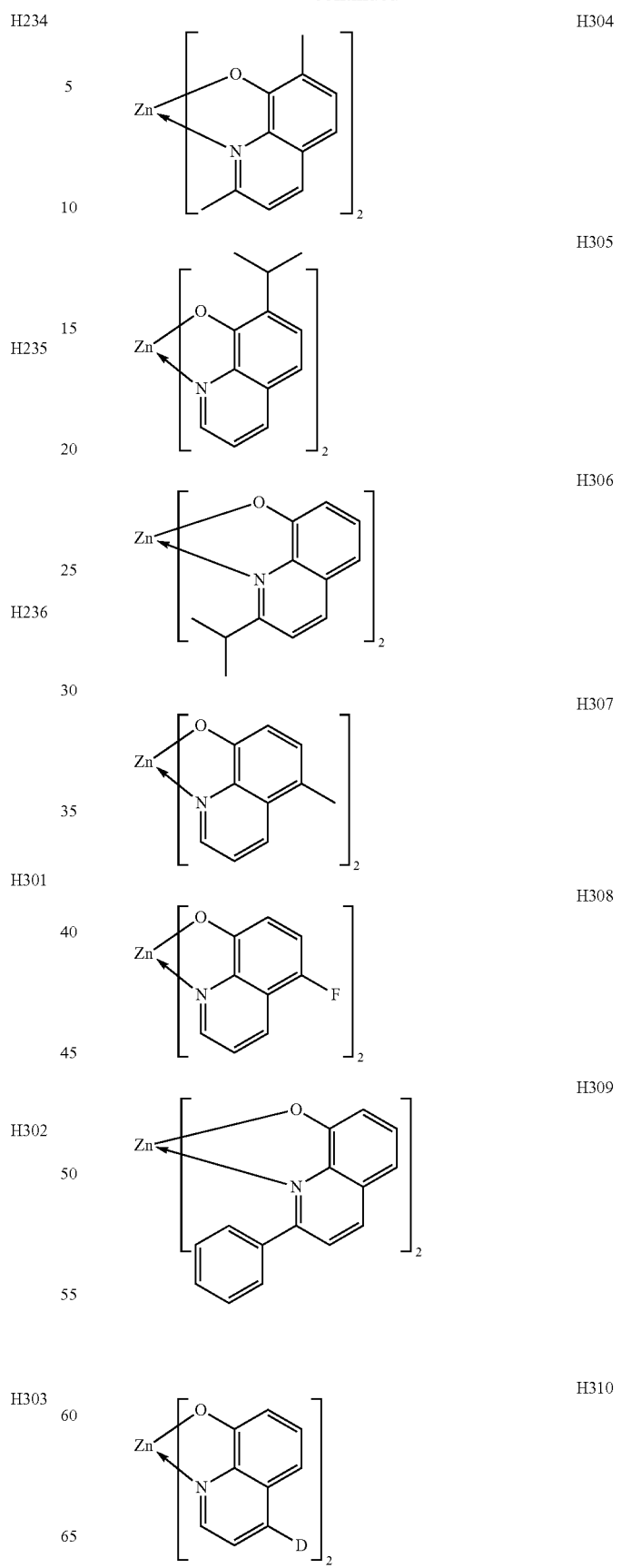

H311 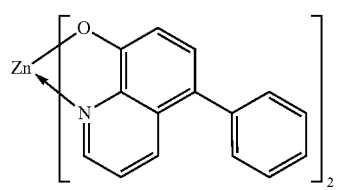
H312 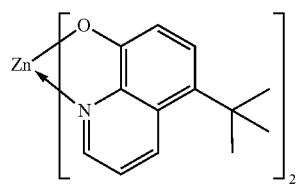
H313 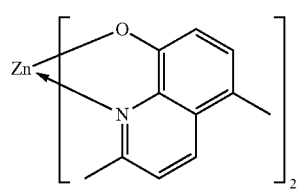
H314 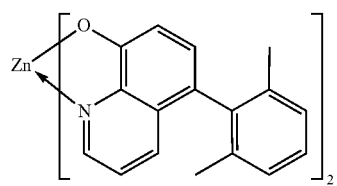
H315 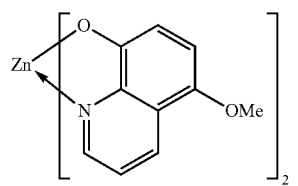
H316 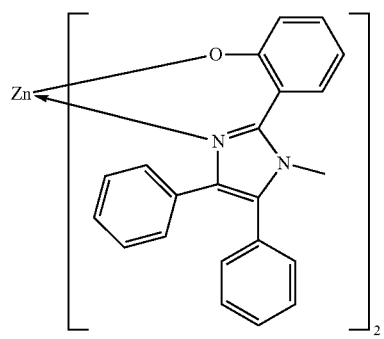
H317 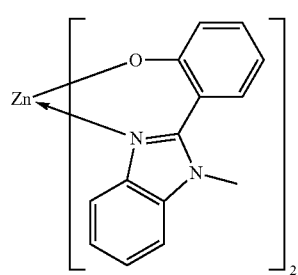
H318 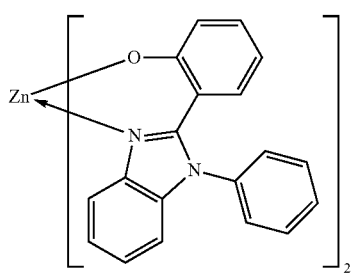
H319 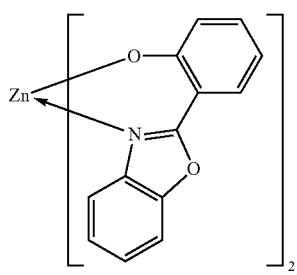
H320 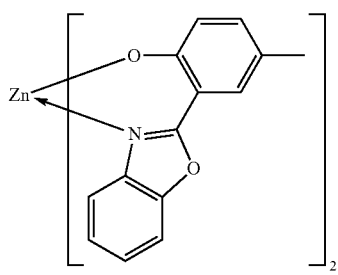
H321 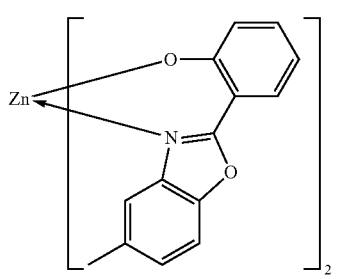
H322 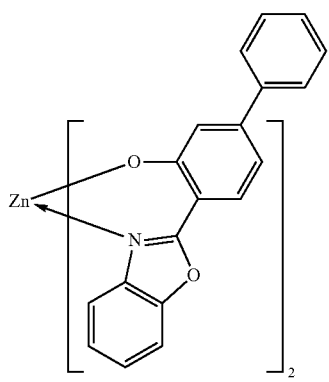

H323 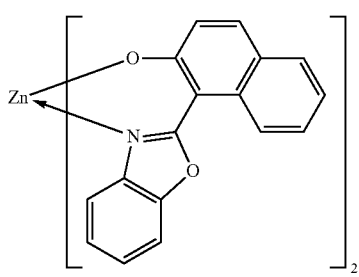
H324 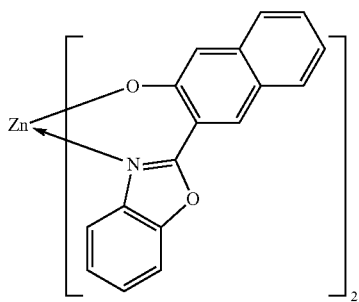
H325 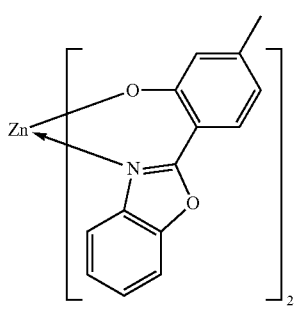
H326 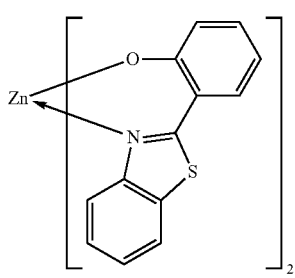
H327 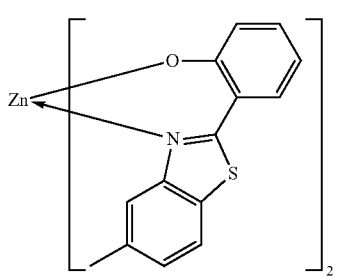
H328 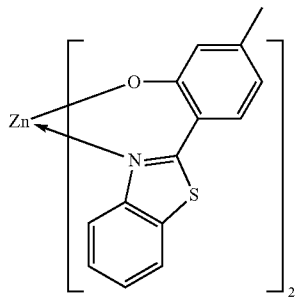
H329 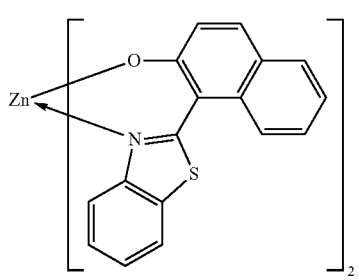
H330 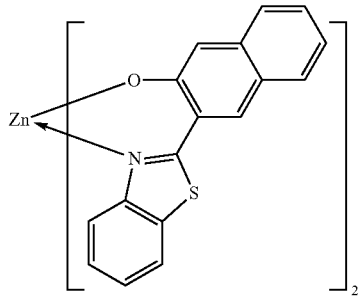
H331 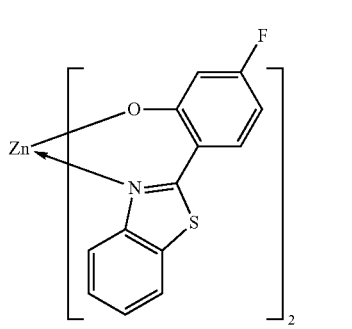
H332 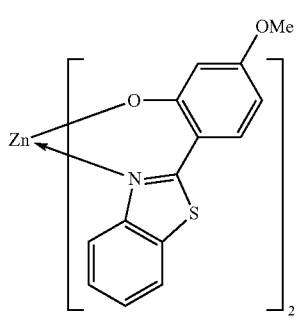

-continued

H333

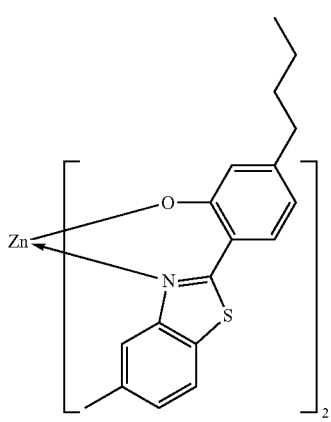

H334

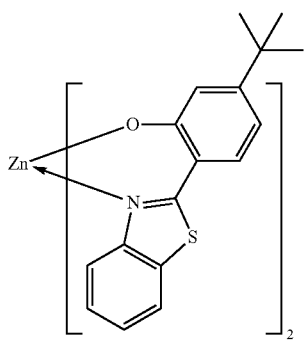

H335

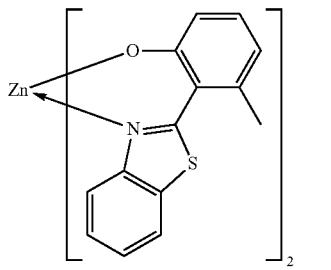

H336

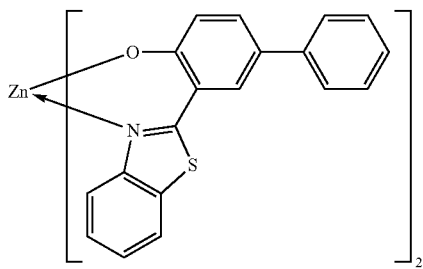

The exemplified compounds can be classified into several groups depending on a relationship between a ligand and a metal from the viewpoint of the stability of a metal complex itself.

Here, for ligands represented in the following type I to type III, distances between a nitrogen atom and oxygen atom included in each of the ligands and serving to coordinate to a metal atom are compared. The distances were each determined as follows: the stable structure of each of the ligands was calculated by employing an MM2 method as molecular mechanical calculation, and then the distance between the nitrogen atom and the oxygen atom was calculated from the structure.

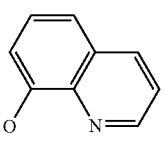 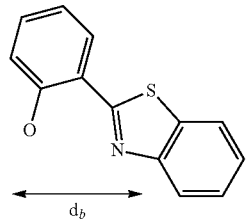

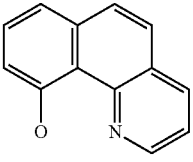

As a result of the calculation, the $d_a$ of a quinolinol ligand (type I) was found to be 2.68 Å, the $d_b$ of a phenylbenzothiazole ligand (type II) was found to be 2.60 Å, and the $d_c$ of a benzoquinolinol ligand (type III) was found to be 2.52 Å.

Meanwhile, the respective metal ionic radii of Mg, Zn, and Be are 0.75 Å, 0.83 Å, and 0.30 Å, respectively. In that case, Mg and Zn as metals having large ionic radii are suitable for the quinolinol ligand as the type I, and Be as a metal having a small metal ionic radius is suitable for the phenylbenzoxazole ligand as the type III. By the same reason, Be is also suitable for the phenylbenzothiazole ligand or the benzoquinolinol ligand. In actuality, when Mg or Zn is selected as a metal atom to be incorporated into a complex, it is difficult to synthesize a complex containing the benzoquinolinol ligand in which the distance between the nitrogen atom and the oxygen atom is long.

The metal complexes represented by Exemplified Compounds H101 to H115 are each a complex in which a central metal is Mg and a ligand is a quinolinol derivative. The quinolinol derivative is a ligand capable of producing a stable complex based on the ionic radius of Mg and is a compound having a small molecular weight. Accordingly, the complex can sublimate at a low sublimation temperature. The metal complexes represented by H116 to H118 are each a complex in which a central metal is Mg and a ligand is a phenylimidazole derivative. According to calculation, a distance between a nitrogen atom and oxygen atom in the phenylimidazole derivative is 2.56 Å, and hence the ligand can complex Mg. The ligand itself has a wide bang gap and hence the ligand is suitable for obtaining a high $T_1$ energy. The metal complexes represented by H119 to H125 are each a complex in which a central metal is Mg and a ligand is a phenylbenzoxazole derivative. A benzoxazole ring is a stable heterocycle. In addition, according to calculation, a distance between a nitrogen atom and oxygen atom in the benzoxazole derivative is 2.69 Å, and hence the ligand can produce a stable Mg complex. In addition, the ligand is a ligand suitable for the utilization of a high $T_1$ energy because of its wide bang gap. Therefore, an organic light-emitting device having high emission efficiency can be obtained. The metal complexes represented by H126 to H136 are each a complex in which a central metal is Mg and a ligand is a phenylbenzothiazole derivative. A benzothiazole ring is a stable heterocycle and is a ligand capable of producing the most stable complex. Accordingly, the ligand is suitable for improving the stability and device lifetime of a device. By the way, the introduction of a substituent into any one of the ligands described above can suppress its stacking. Accordingly, the introduction can improve the sublimability of a complex and can change the band gap of the complex. It is to be noted that a carbon atom adjacent to the nitrogen atom has high activity and hence the activity of the carbon atom can be controlled through substitution with a methyl group or an isopropyl group.

H201 to H206 are each a complex in which a central metal is Be and a ligand is a quinolinol derivative. Although the stability of each of the complexes is not very high in consideration of the ionic radius of a Be atom, the complex can sublimate at a low sublimation temperature because of its small molecular weight. H207 to H215 are each a complex in which a central metal is Be and a ligand is a benzoquinolinol derivative. A benzoquinolinol ring is a stable heterocycle. In addition, in consideration of the ionic radius of Be, the complex containing the benzoquinolinol ligand is a stable complex out of the Be complexes, and hence can provide a high-efficiency and long-lifetime organic light-emitting device. H216 to H218 are each a metal complex in which a central metal is Be, and each have a ligand having a wide band gap and suitable upon utilization of a high $T_1$ energy. Therefore, a high-efficiency organic light-emitting device can be obtained. H219 to H225 are each a complex in which a central metal is Be and a ligand is a phenylbenzoxazole derivative. A benzoxazole ligand is a stable heterocycle and is hence a ligand capable of producing a stable Be complex. In addition, the benzoxazole ligand is suitable for the utilization of a high $T_1$ energy and hence can provide a high-efficiency organic light-emitting device. H226 to H236 are each a complex in which a central metal is Be and a ligand is a phenylbenzothiazole derivative. A benzothiazole ligand is a stable heterocycle and is a ligand capable of producing the most stable Be complex. In addition, the complex has a $T_1$ energy suitable for red phosphorescence, and hence can provide a high-efficiency and long-lifetime organic light-emitting device. By the way, the introduction of a substituent into any one of the ligands described above can suppress its stacking. Accordingly, the introduction can improve the sublimability of a complex and can change the band gap of the complex. It is to be noted that a carbon atom adjacent to the nitrogen atom has high activity and hence the activity of the carbon atom can be controlled through substitution with a methyl group or an isopropyl group.

H301 to H315 are each a complex in which a central metal is Zn and a ligand is a quinolinol derivative. The ligand can produce an extremely stable complex based on the ionic radius of a Zn complex and has a small molecular weight, and hence the complex can sublimate at a low sublimation temperature. In addition, the introduction of a substituent suppresses the stacking of the ligand, and hence can improve the sublimability of the complex and can change the band gap of the complex. H316 to H318 are each a complex in which a central metal is Zn and a ligand is a phenylimidazole derivative. A distance between a nitrogen atom and oxygen atom in the ligand is 2.56 Å, and hence the ligand can complex Zn. The ligand itself has a wide bang gap and hence the ligand is suitable upon utilization of a high $T_1$ energy. The introduction of a substituent into any one of the ligands described above can suppress its stacking. Accordingly, the introduction can improve the sublimability of a complex and can change the band gap of the complex. It is to be noted that a carbon atom adjacent to the nitrogen atom has high activity and hence the activity of the carbon atom can be controlled through substitution with a methyl group or an isopropyl group.

(7) Constituent Material Except Iridium Complex and metal Complex

As described above, the organic compound layer (preferably the emission layer) of the organic light-emitting device of the present invention contains at least the iridium complex represented by the general formula [1] and the metal complex compound represented by the general formula [5]. It is to be noted that in the present invention, conventionally known low-molecular weight and high-molecular weight materials can each be used as required in addition to these compounds. More specifically, a hole-injectable/transportable material, a light emission assist material, an electron-injectable/transportable material, or the like can be used together with the iridium complex and the metal complex compound.

Examples of those materials are listed below.

The hole-injectable/transportable material is preferably a material having a high hole mobility so that the injection of a hole from the anode may be facilitated and the injected hole can be transported to the emission layer. In addition, the material is preferably a material having a high glass transition point for preventing the degradation of film quality such as crystallization in the organic light-emitting device. Examples of the low-molecular weight and high-molecular weight materials each having hole-injecting/transporting performance include a triarylamine derivative, an arylcarbazole derivative, a phenylenediamine derivative, a stilbene derivative, a phthalocyanine derivative, a porphyrin derivative, poly(vinyl carbazole), poly(thiophene), and other conductive polymers. Further, the hole-injectable/transportable material is suitably used for the electron blocking layer as well.

Specific examples of a compound to be used as the hole-injectable/transportable material are shown below. However, the compound is of course not limited thereto.

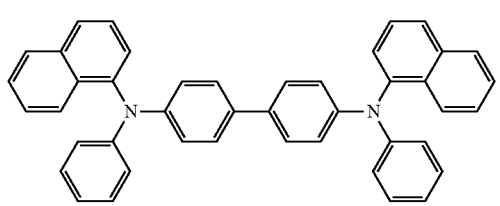

HT1

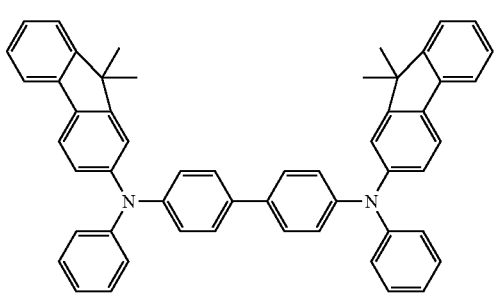

HT2

-continued
HT3
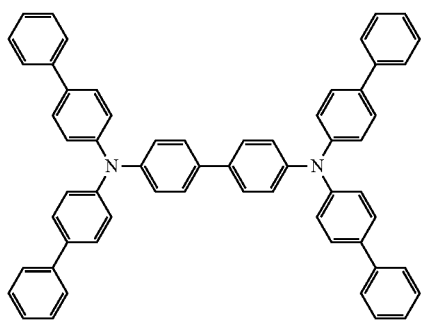
HT4
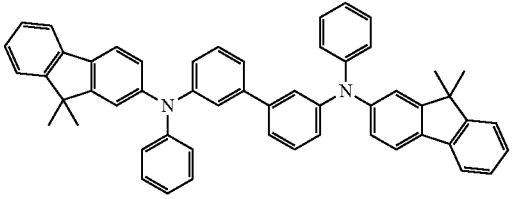
HT5
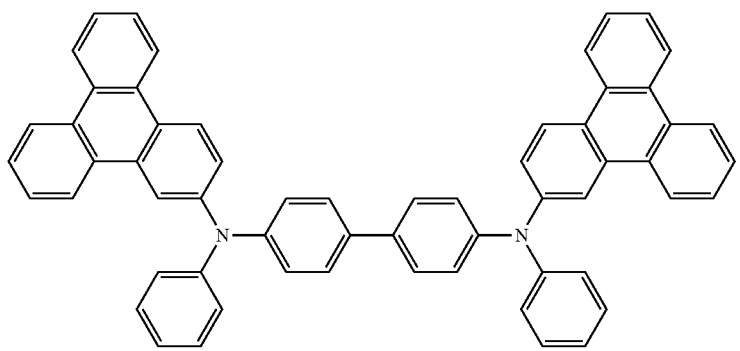
HT6
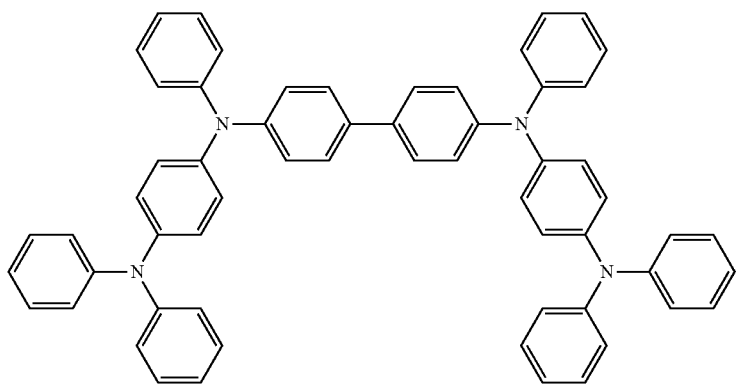
HT7
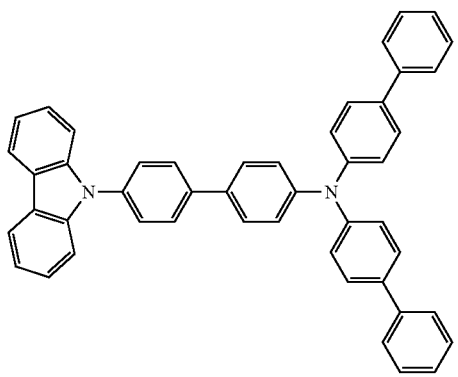
HT8
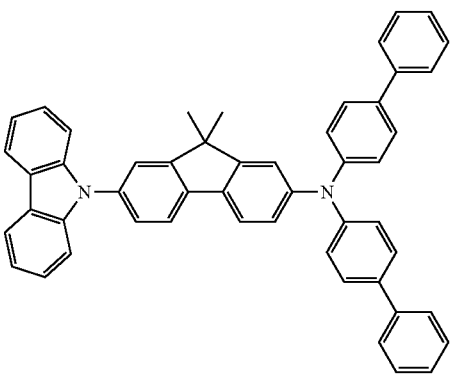

-continued
HT9
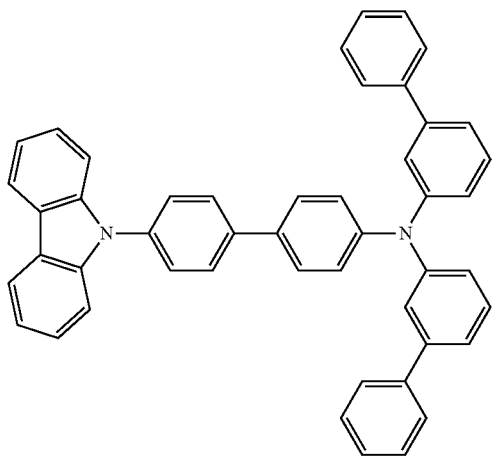
HT10
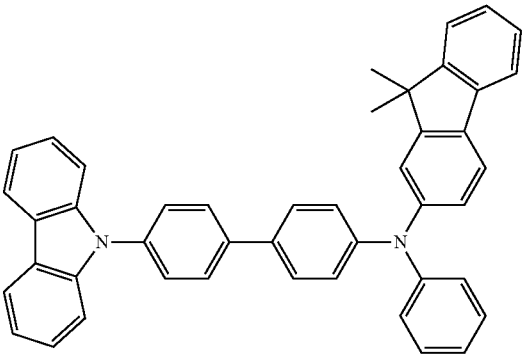
HT11
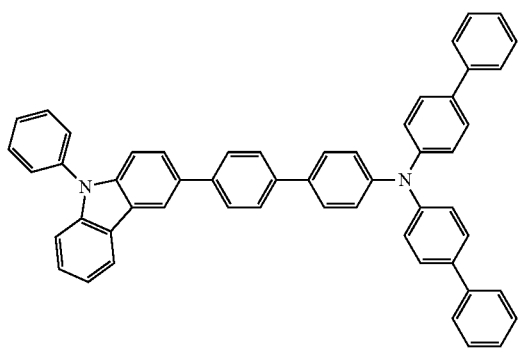
HT12
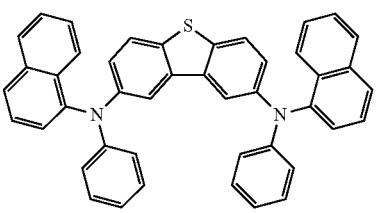
HT13
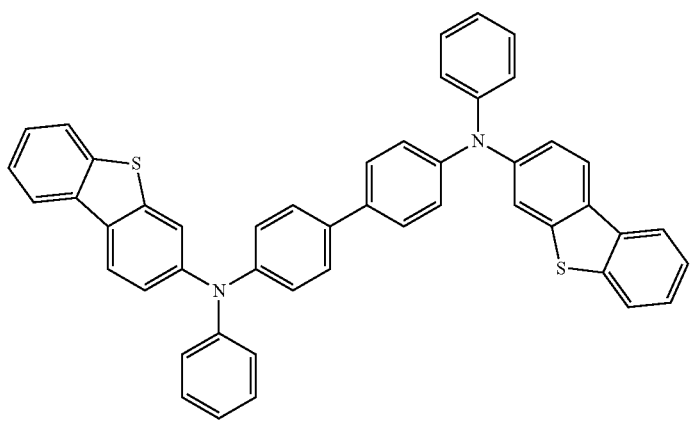

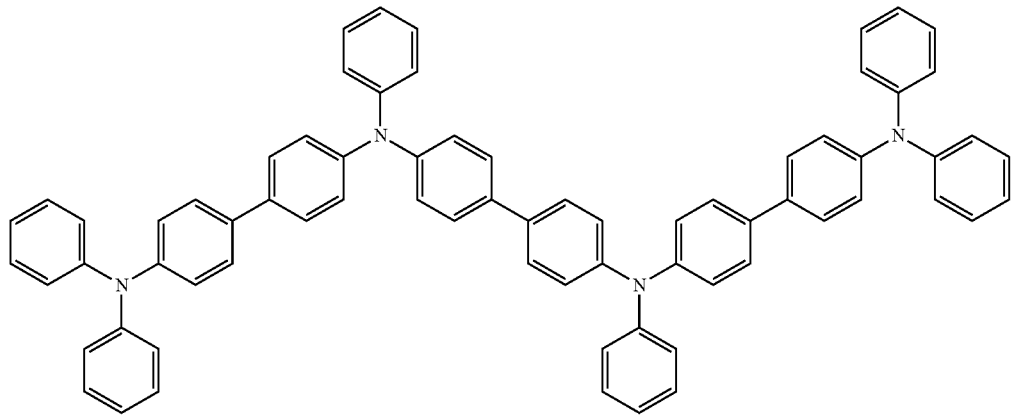

HT14

Examples of the light-emitting material mainly involved in a light-emitting function include: condensed ring compounds (such as a fluorene derivative, a naphthalene derivative, a pyrene derivative, a perylene derivative, a tetracene derivative, an anthracene derivative, and rubrene); a quinacridone derivative; a coumarin derivative; a stilbene derivative; an organic aluminum complex such as tris(8-quinolinolato)aluminum; a platinum complex; a rhenium complex; a copper complex; a europium complex; a ruthenium complex; and polymer derivatives such as a poly(phenylene vinylene) derivative, a poly(fluorene) derivative, and a poly(phenylene) derivative in addition to the iridium complex represented by the general formula [1] or a derivative thereof.

Specific examples of a compound to be used as the light-emitting material are shown below. However, the compound is of course not limited thereto.

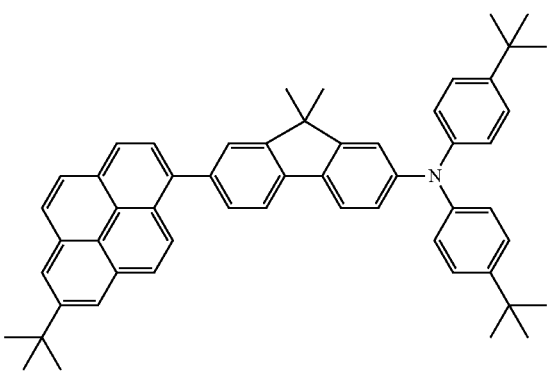

BD3

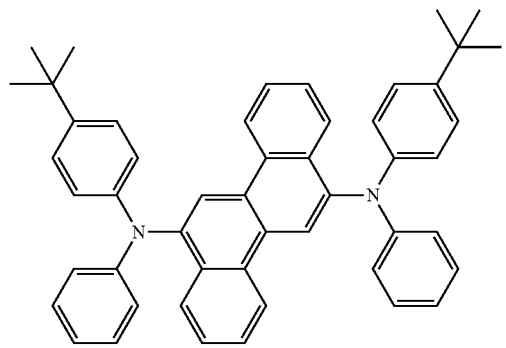

BD1

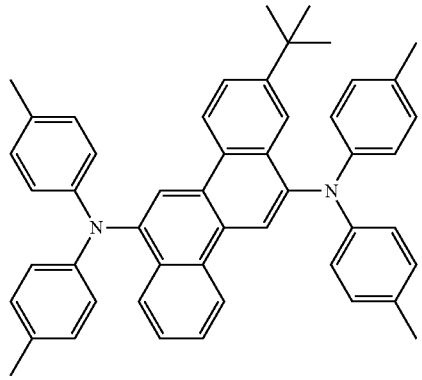

BD2

BD6 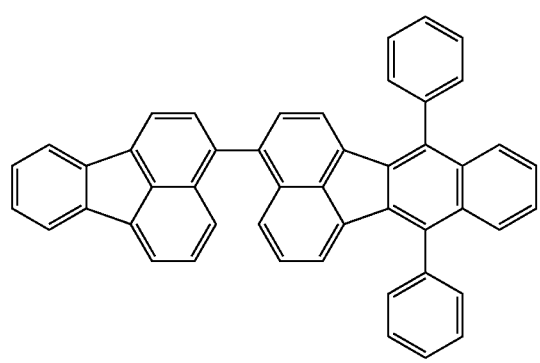
GD3 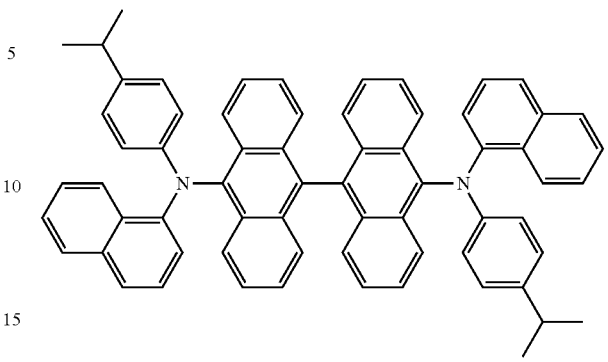
BD7 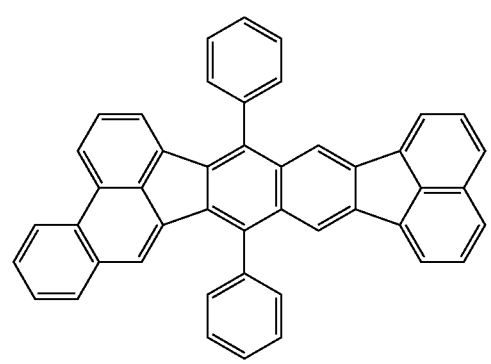
GD4 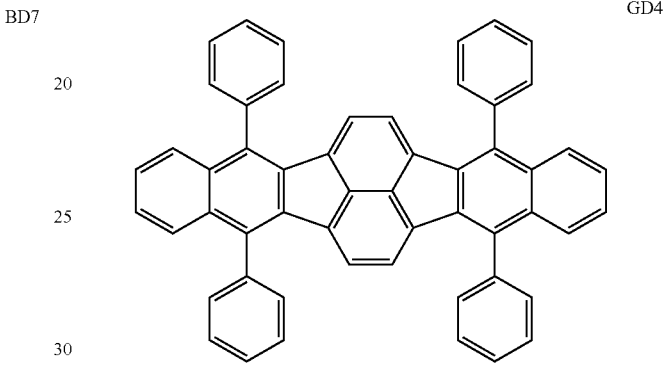
BD8 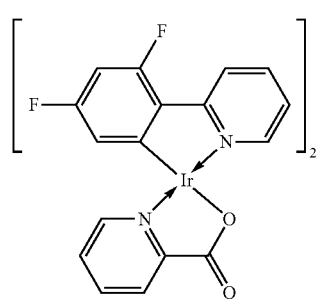
GD5 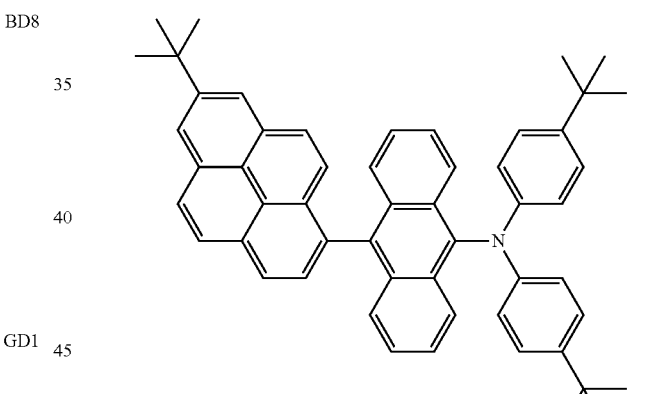
GD1 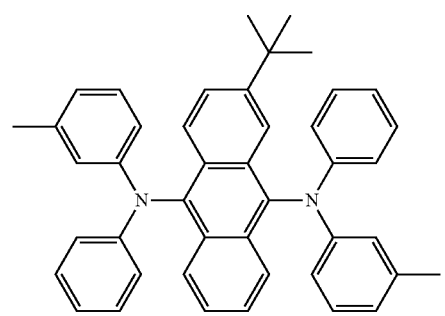
GD6 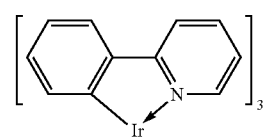
GD2 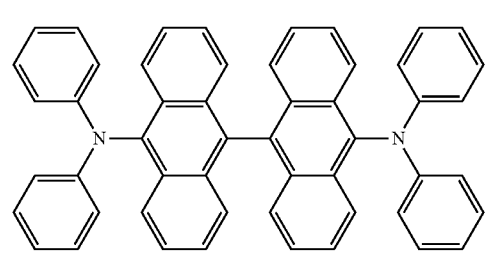
GD7 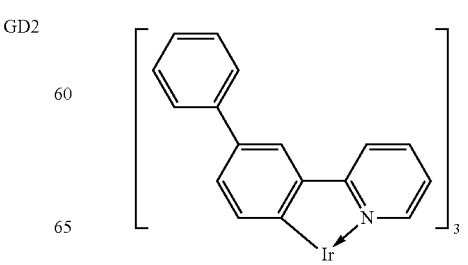

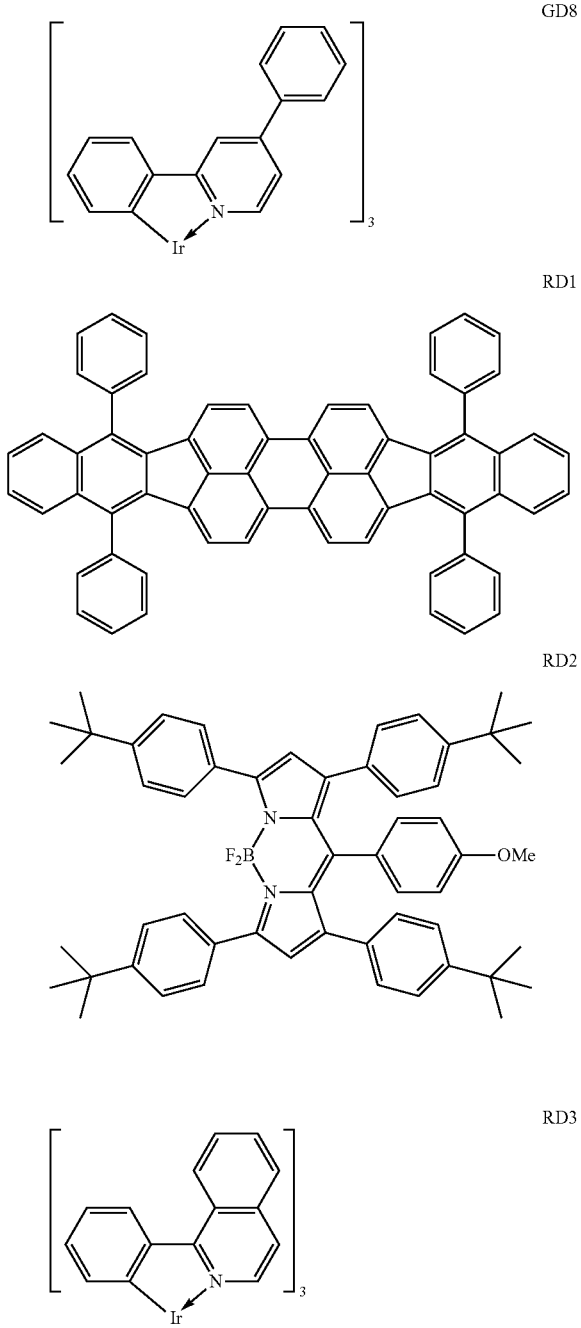
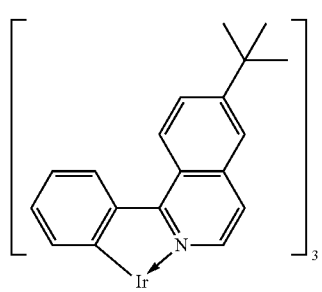

Examples of the host or assist material to be incorporated into the emission layer include: an aromatic hydrocarbon compound or a derivative thereof; a carbazole derivative; a dibenzofuran derivative; a dibenzothiophene derivative; an organic aluminum complex such as tris(8-quinolinolato) aluminum; and an organic beryllium complex in addition to the heterocycle-containing compound represented the general formula [5].

Specific examples of a compound to be used as the host or assist material to be incorporated into the emission layer are shown below. However, the compound is of course not limited thereto.

EM1
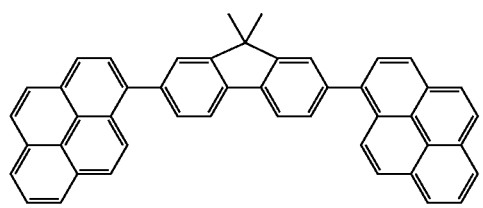
EM2
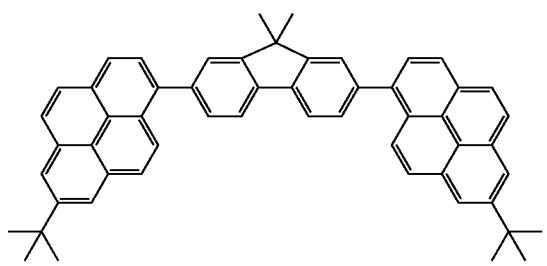
EM3
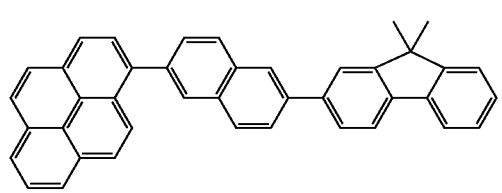
EM4
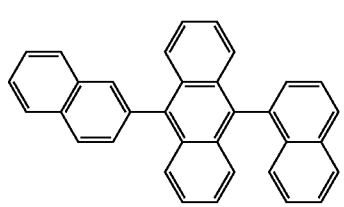
EM5
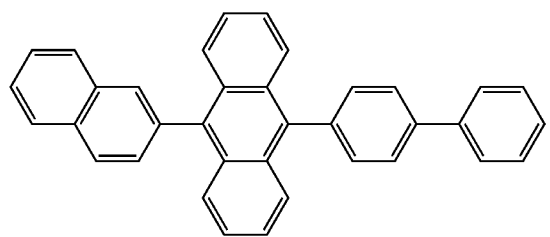
EM6
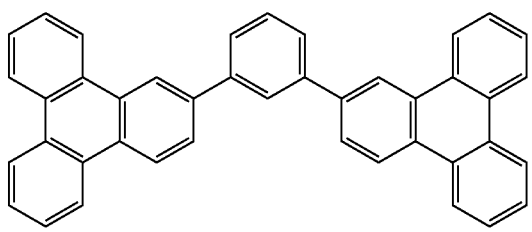
EM7
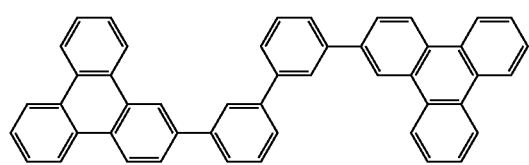
EM8
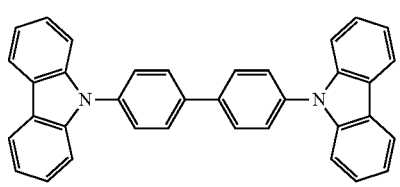
EM9
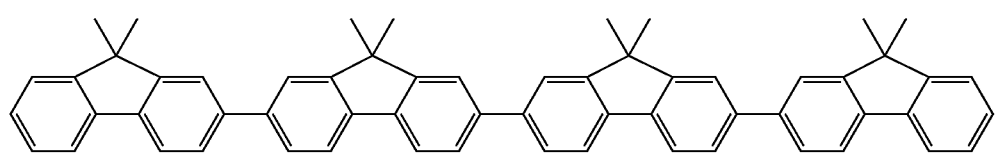
EM10
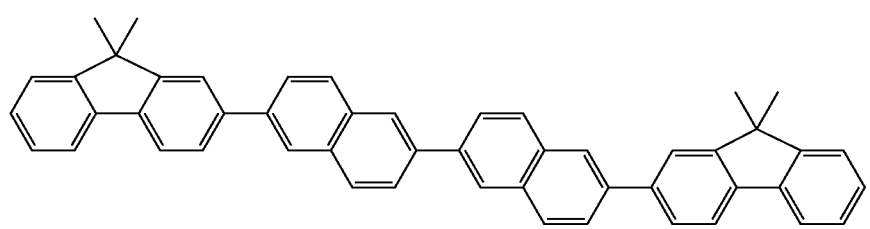

-continued

EM11

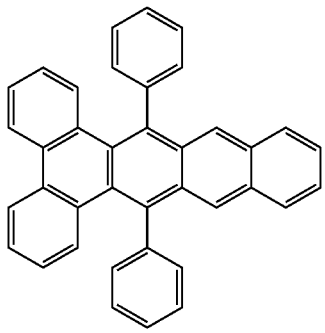

EM12

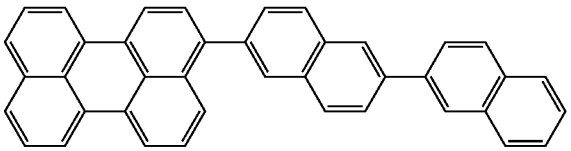

EM13

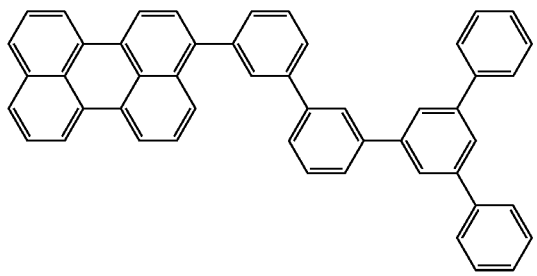

EM14

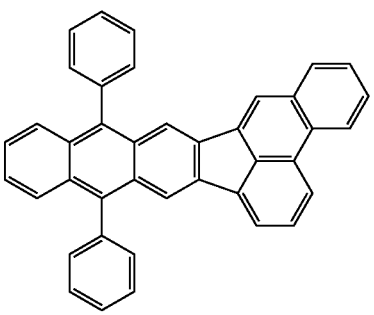

EM15

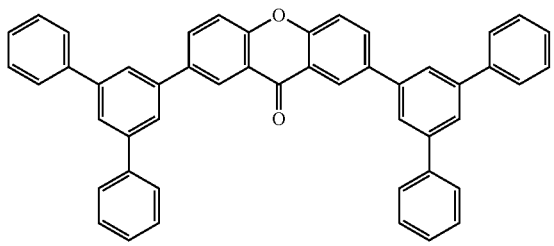

EM16

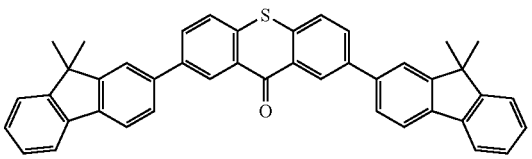

EM17

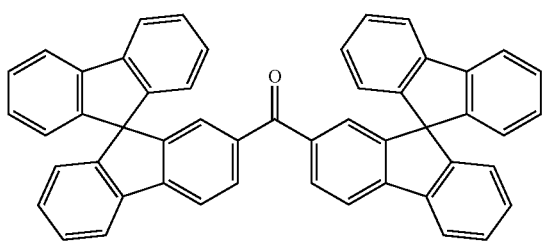

The electron-injectable/transportable material can be arbitrarily selected from materials that allow electrons to be easily injected from the cathode and can transport the injected electrons to the emission layer in consideration of, for example, the balance with the hole mobility of the hole-transportable material. Examples of the material having electron-injecting performance and electron-transporting performance include an oxadiazole derivative, an oxazole derivative, a pyrazine derivative, a triazole derivative, a triazine derivative, a quinoline derivative, a quinoxaline derivative, a phenanthroline derivative, and an organic aluminum complex. Further, the electron-injectable/transportable material is suitably used for the hole blocking layer as well.

Specific examples of a compound to be used as the electron-injectable/transportable material are shown below. However, the compound is of course not limited thereto.

ET1

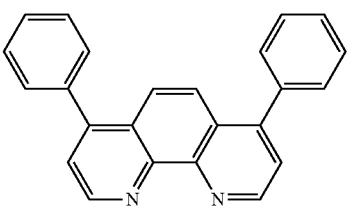

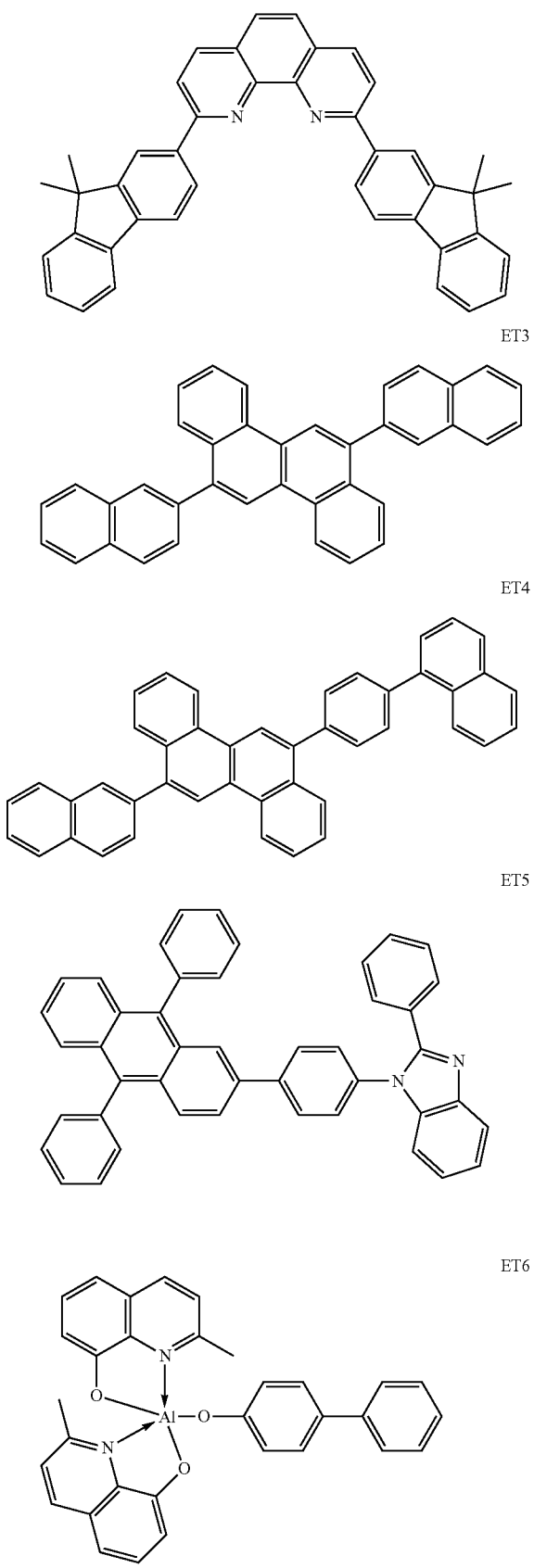

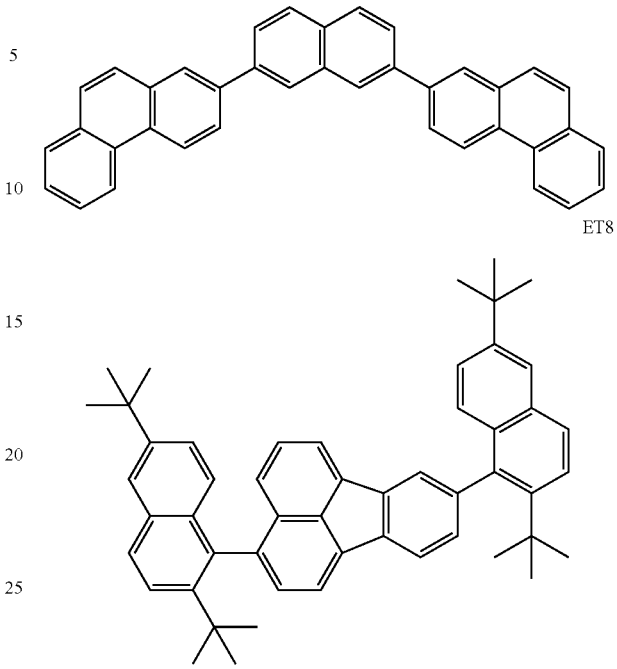

A constituent material for the anode desirably has as large a work function as possible. Examples thereof may include: metal simple substances such as gold, platinum, silver, copper, nickel, palladium, cobalt, selenium, vanadium, and tungsten or alloys obtained by combining these metal simple substances; metal oxides such as tin oxide, zinc oxide, indium oxide, indium tin oxide (ITO), and indium zinc oxide; and conductive polymers such as polyaniline, polypyrrole, and polythiophene.

One kind of those electrode substances may be used alone, or two or more kinds thereof may be used in combination. In addition, the anode may be of a single-layer construction or may be of a multilayer construction.

On the other hand, a constituent material for the cathode desirably has as small a work function as possible. Examples thereof include: metal simple substances such as alkali metals such as lithium, alkaline earth metals such as calcium, aluminum, titanium, manganese, silver, lead, and chromium. Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may be of a single-layer construction or may be of a multilayer construction.

The organic compound layer (such as the hole-injecting layer, the hole transport layer, the electron blocking layer, the emission layer, the hole blocking layer, the electron transport layer, or the electron-injecting layer) for forming the organic light-emitting device of the present invention is formed by the following method.

A dry process such as a vacuum vapor deposition method, an ionized vapor deposition method, sputtering, or a plasma process can be used for the formation of the organic compound layer for forming the organic light-emitting device of the present invention. In addition, a wet process involving dissolving the constituent materials in an appropriate solvent and forming a layer by a known application method (such as spin coating, dipping, a casting method, an LB method, or an ink jet method) can be used instead of the dry process.

Here, when the layer is formed by the vacuum vapor deposition method, the solution application method, or the like, the layer hardly undergoes crystallization or the like and is excellent in stability over time. In addition, when the layer is formed by the application method, the film can be formed by using the constituent materials in combination with an appropriate binder resin.

Examples of the binder resin include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

(8) Application of Organic Light-Emitting Device of the Present Invention

The organic light-emitting device of the present invention can be used as a constituent member for a display apparatus or lighting apparatus. In addition, the device finds use in applications such as an exposure light source for an image-forming apparatus of an electrophotographic system, a backlight for a liquid crystal display apparatus, and a light-emitting apparatus including a white light source and a color filter. Examples of the color filter include filters that transmit light beams having three colors, i.e., red, green, and blue colors.

A display apparatus of the present invention includes the organic light-emitting device of the present invention in its display portion. It is to be noted that the display portion includes multiple pixels.

In addition, the pixels each have the organic light-emitting device of the present invention and a transistor as an example of an active device (switching device) or amplifying device for controlling emission luminance, and the anode or cathode of the organic light-emitting device and the drain electrode or source electrode of the transistor are electrically connected to each other. Here, the display apparatus can be used as an image display apparatus for a PC or the like. The transistor is, for example, a TFT device and the TFT device is provided on, for example, the insulating surface of a substrate. In addition, the TFT device preferably includes an electrode formed of a transparent oxide semiconductor.

The display apparatus may be an information processing apparatus that includes an image input portion for inputting image information from, for example, an area CCD, a linear CCD, or a memory card, and displays an input image on its display portion.

In addition, the display portion of an imaging apparatus or inkjet printer may have a touch panel function. The drive system of the touch panel function is not particularly limited.

In addition, the display apparatus may be used in the display portion of a multifunction printer.

A lighting apparatus is an apparatus for lighting, for example, the inside of a room. The lighting apparatus may emit light having any one of the following colors: a white color (having a color temperature of 4,200 K), a daylight color (having a color temperature of 5,000 K), and colors ranging from blue to red colors.

Figure 2:
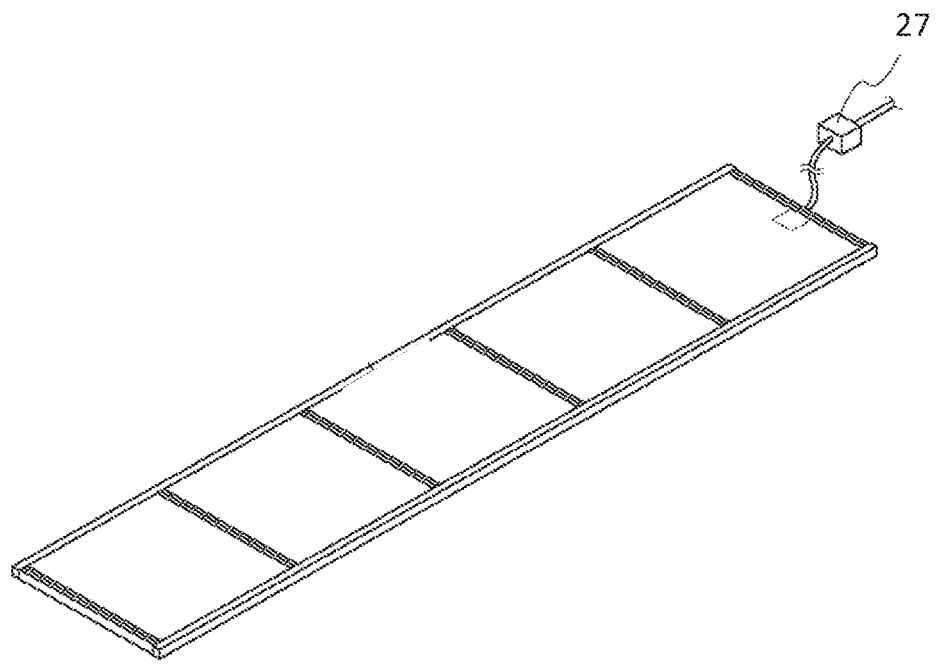
FIG. 2 shows a lighting apparatus according to an embodiment of the present invention.

A lighting apparatus of the present invention includes the organic light-emitting device of the present invention and an AC/DC converter circuit 27 (circuit for converting an AC voltage into a DC voltage) connected to the organic light-emitting device as shown in FIG. 2. It is to be noted that the lighting apparatus may further have a color filter.

Figure 3:
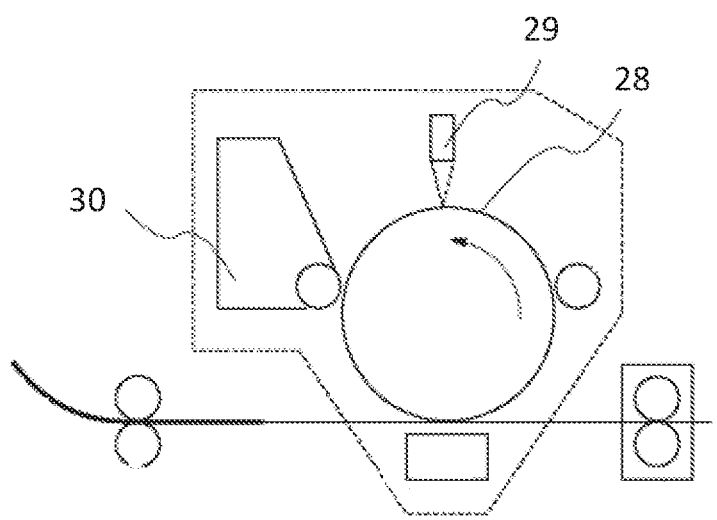
FIG. 3 shows an image-forming apparatus according to an embodiment of the present invention.

As shown in FIG. 3, an image-forming apparatus of the present invention is an image-forming apparatus including: a photosensitive member 28; charging unit for charging the surface of the photosensitive member; exposing unit 29 for exposing the photosensitive member to form an electrostatic latent image; and a developing unit 30 for developing the electrostatic latent image formed on the surface of the photosensitive member. Here, the exposing unit to be provided in the image-forming apparatus includes the organic light-emitting device of the present invention.

In addition, the organic light-emitting device of the present invention can be used as a constituent member for an exposing apparatus for exposing a photosensitive member. An exposing apparatus including a plurality of the organic light-emitting devices of the present invention is, for example, an exposing apparatus in which the organic light-emitting devices of the present invention are placed to form a line along a predetermined direction.

Next, the display apparatus of the present invention is described with reference to the drawing. FIG. 1 is a schematic sectional view illustrating an example of a display apparatus including an organic light-emitting device and a TFT device connected to the organic light-emitting device. It is to be noted that the organic light-emitting device of the present invention is used as the organic light-emitting device constituting a display apparatus 1 of FIG. 1.

The display apparatus 1 of FIG. 1 includes a substrate 11 made of glass or the like and a moisture-proof film 12 for protecting a TFT device or organic compound layer, the film being provided on the substrate. In addition, a metal gate electrode 13 is represented by reference numeral 13, a gate insulating film 14 is represented by reference numeral 14, and a semiconductor layer is represented by reference numeral 15.

A TFT device 18 includes the semiconductor layer 15, a drain electrode 16, and a source electrode 17. An insulating film 19 is provided on the TFT device 18. An anode 21 constituting the organic light-emitting device and the source electrode 17 are connected to each other through a contact hole 20.

It is to be noted that a system for the electrical connection between the electrode (anode or cathode) in the organic light-emitting device and the electrode (source electrode or drain electrode) in the TFT is not limited to the aspect illustrated in FIG. 1. In other words, one of the anode and the cathode, and one of the source electrode and drain electrode of the TFT device have only to be electrically connected to each other.

Although multiple organic compound layers are illustrated like one layer in the display apparatus 1 of FIG. 1, an organic compound layer 22 may be multiple layers. A first protective layer 24 and second protective layer 25 for suppressing the degradation of the organic light-emitting device are provided on a cathode 23.

When the display apparatus 1 of FIG. 1 is a display apparatus that emits white light, an emission layer in the organic compound layer 22 in FIG. 1 may be a layer obtained by mixing a red light-emitting material, a green light-emitting material, and a blue light-emitting material. In addition, the layer may be a stacked emission layer obtained by stacking a layer formed of the red light-emitting material, a layer formed of the green light-emitting material, and a layer formed of the blue light-emitting material. Further, alternatively, the following aspect is permitted: the layer formed of the red light-emitting material, the layer formed of the green light-emitting material, and the layer formed of the blue light-emitting material are, for example, arranged side by side to form domains in one emission layer.

Although the transistor is used as a switching device in the display apparatus 1 of FIG. 1, an MIM device may be used instead of the transistor as the switching device.

In addition, the transistor to be used in the display apparatus 1 of FIG. 1 is not limited to a transistor using a monocrystalline silicon wafer and may be a thin-film transistor including an active layer on the insulating surface of a substrate. A thin-film transistor using monocrystalline silicon as the active layer, a thin-film transistor using non-monocrystalline silicon such as amorphous silicon or microcrystalline silicon as the active layer, or a thin-film transistor using a non-monocrystalline oxide semiconductor such as an indium zinc oxide or an indium gallium zinc oxide as the active layer is also permitted. It is to be noted that the thin-film transistor is also called a TFT device.

The transistor in the display apparatus 1 of FIG. 1 may be formed in a substrate such as an Si substrate. Here, the phrase "formed in a substrate" means that the transistor is produced by processing the substrate itself such as an Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light-emitting device is preferably provided in the Si substrate.

As described above, the driving of the display apparatus using the organic light-emitting device of the present invention enables display that has good image quality and is stable over a long time period.

EXAMPLES

Synthesis Example 1 and Comparative Example 1

Synthesis of Exemplified Compound KK-01 and Comparative Compound E2

Exemplified Compound KK-01 and Compound E2 were synthesized with reference to, for example, PTL 1 and NPL 1 to 7 according to the following synthesis scheme. In the following synthesis scheme, THF represents tetrahydrofuran, r.t. represents room temperature, Ph represents a phenyl group, Bu represents a butyl group, and Et represents an ethyl group.

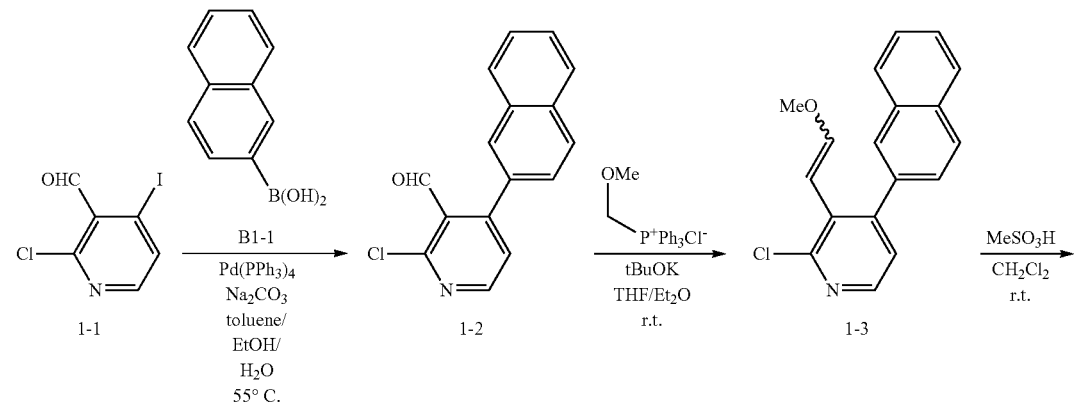

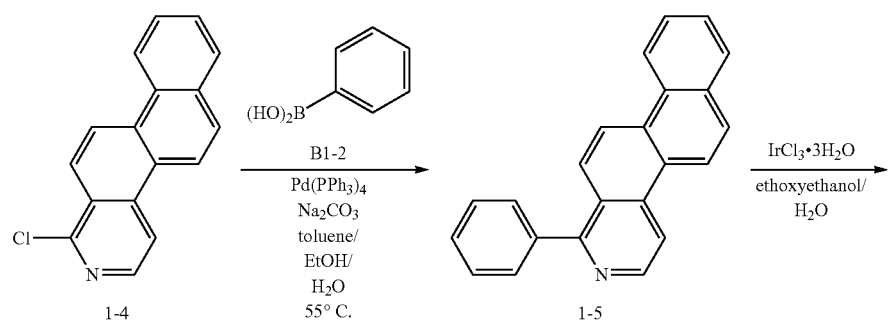

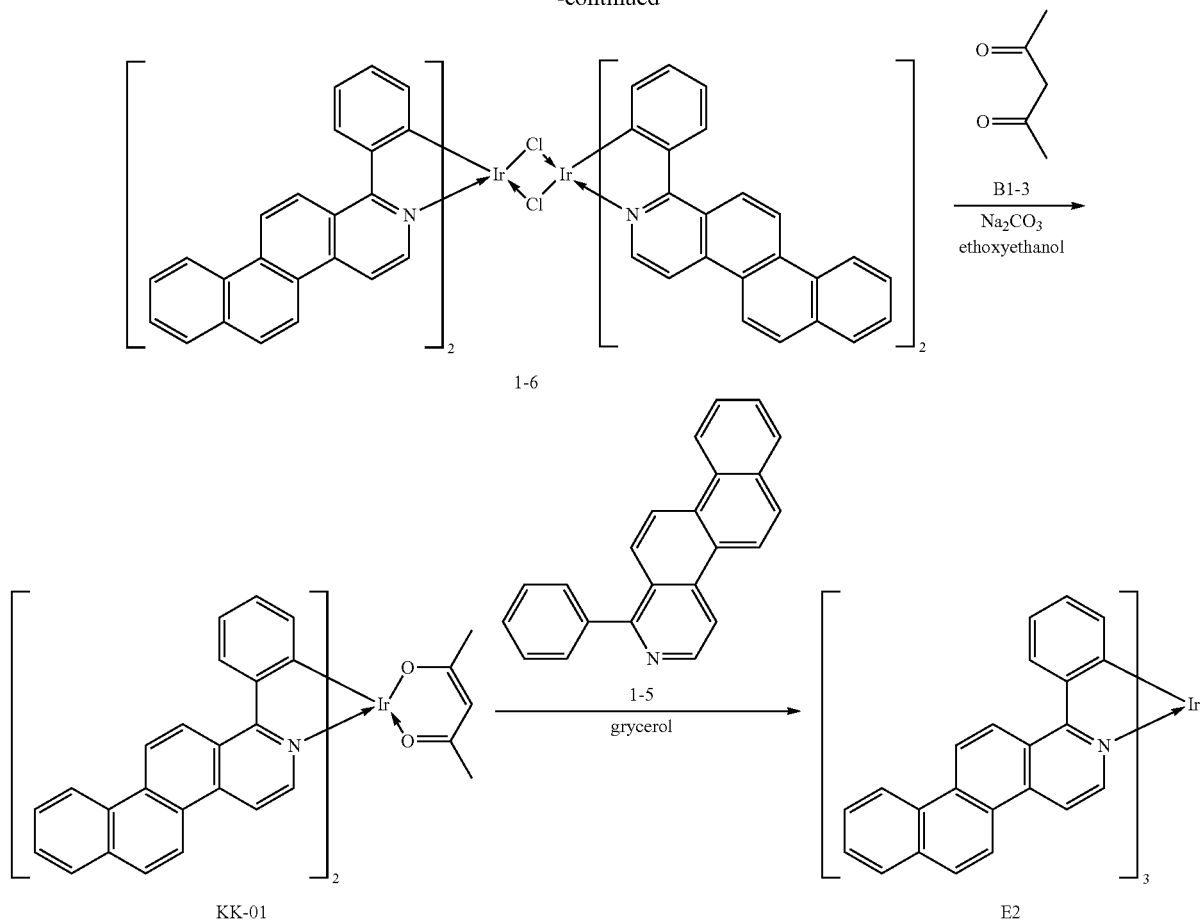

1-6

KK-01

E2

Specifically, Exemplified Compound KK-01 and Compound E2 were obtained through the following steps (1) to (4):
(1) the synthesis of an organic compound (Compound 1-5) serving as a ligand with Compound 1-1 as a starting raw material;
(2) the synthesis of a chloro-crosslinked complex (Compound 1-6);
(3) the synthesis of a complex having an auxiliary ligand (Exemplified Compound KK-01); and
(4) the synthesis of a three-coordinate complex (Compound E2).

The identification of KK-01 and E2 thus obtained was performed by matrix assisted ionization time-of-flight mass spectrometry (MALDI-TOF-MS). Table 1 shows the results. Subsequently, sublimation purification was performed under the condition of $1\times10^{-4}$ Pa. As a result, KK-01 sublimated at 390° C. and hence a sublimated product was able to be obtained. In contrast, E2 thermally decomposed at 390° C. and hence no sublimated product could be obtained.

Synthesis Example 2

Synthesis of Exemplified Compound KK-04

Exemplified Compound KK-04 was synthesized by the same synthesis method as that of Synthesis Example 1 except that in Synthesis Example 1, a compound shown below was used instead of Synthesis Raw Material B1-1.

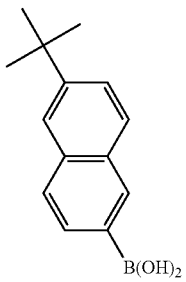

The structure of a purified product obtained by subjecting the synthesized iridium complex to sublimation purification under the condition of $1\times10^{-4}$ Pa was confirmed by the same method as that of Synthesis Example 1. Table 1 shows the result.

Synthesis Example 3

Synthesis of Exemplified Compound KK-05

Exemplified Compound KK-05 was synthesized by the same synthesis method as that of Synthesis Example 1 except that in Synthesis Example 1, a compound shown below was used instead of Synthesis Raw Material B1-2.

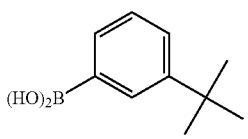

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 4

Synthesis of Exemplified Compound KK-13

Exemplified Compound KK-13 was synthesized by the same synthesis method as that of Synthesis Example 2 except that in Synthesis Example 2, a compound shown below was used instead of Synthesis Raw Material B1-2.

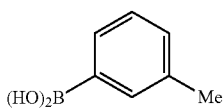

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 5

Synthesis of Exemplified Compound KK-28

Exemplified Compound KK-28 was synthesized by the same synthesis method as that of Synthesis Example 1 except that in Synthesis Example 1, a compound shown below was used instead of Synthesis Raw Material B1-3.

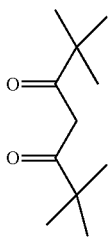

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 6

Synthesis of Exemplified Compound KK-31

Exemplified Compound KK-31 was synthesized by the same synthesis method as that of Synthesis Example 5 except that in Synthesis Example 5, a compound shown below was used instead of Synthesis Raw Material B1-1.

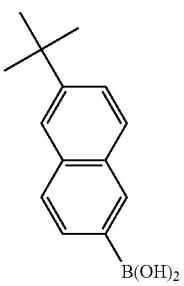 [SMILES: CC(C)(C)c1ccc2cc(B(O)O)ccc2c1]

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 7

Synthesis of Exemplified Compound KK-32

Exemplified Compound KK-32 was synthesized by the same synthesis method as that of Synthesis Example 5 except that in Synthesis Example 5, a compound shown below was used instead of Synthesis Raw Material B1-2.

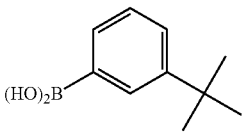

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 8

Synthesis of Exemplified Compound KK-03

KK-03 was synthesized with reference to the same references as those of Synthesis Example 1 above according to the following synthesis scheme. In the following synthesis scheme, THF represents tetrahydrofuran, r.t. represents room temperature, Ph represents a phenyl group, Bu represents a butyl group, and Et represents an ethyl group.

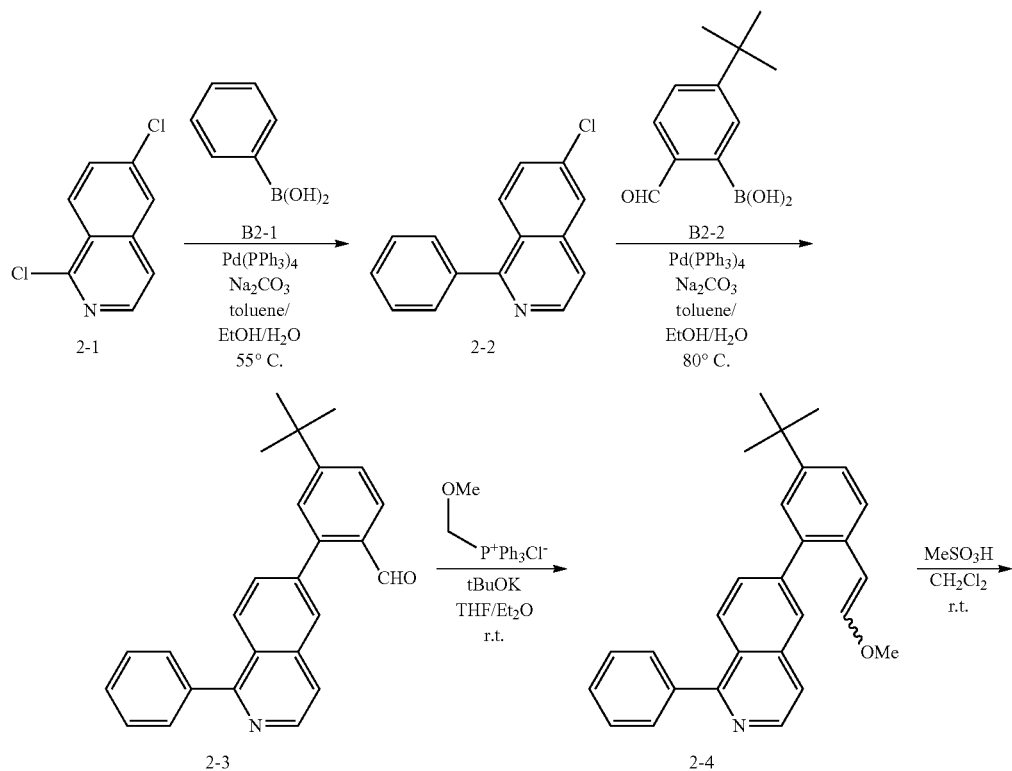
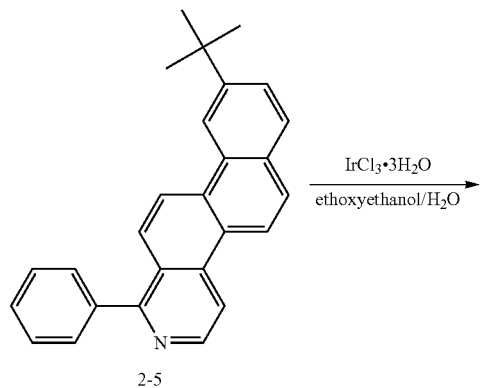
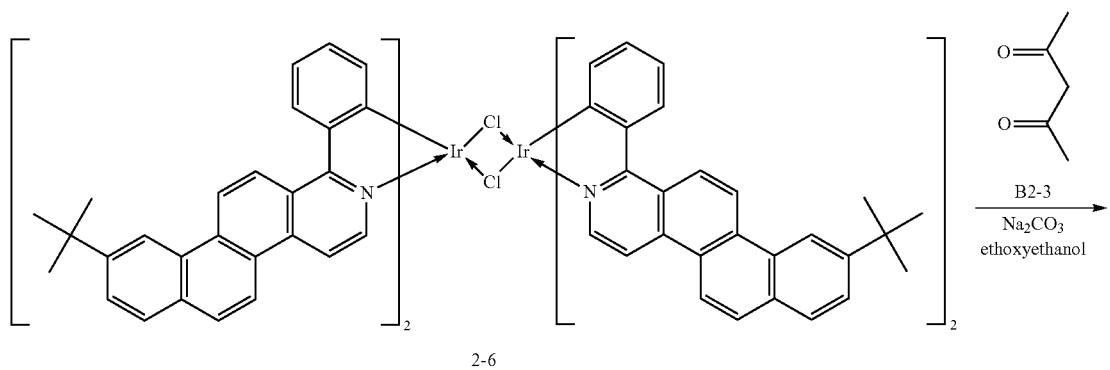

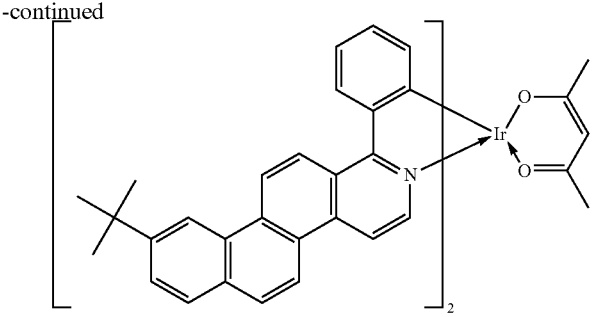

KK-03

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 9

Synthesis of Exemplified Compound KK-12

Exemplified Compound KK-12 was synthesized by the same synthesis method as that of Synthesis Example 8 except that in Synthesis Example 8, a compound shown below was used instead of Synthesis Raw Material B2-1.

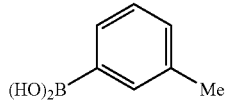

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 10

Synthesis of Exemplified Compound KK-30

Exemplified Compound KK-30 was synthesized by the same synthesis method as that of Synthesis Example 8 except that in Synthesis Example 8, a compound shown below was used instead of Synthesis Raw Material B2-3.

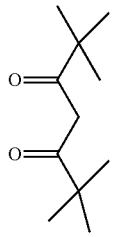

The structure of a purified product obtained by subjecting the synthesized iridium complex to sublimation purification under the condition of 1×10⁻⁴ Pa was confirmed by the same method as that of Synthesis Example 1. Table 1 shows the result.

Synthesis Example 11

Synthesis of Exemplified Compound KK-36

Exemplified Compound KK-36 was synthesized by the same synthesis method as that of Synthesis Example 10 except that in Synthesis Example 10, a compound shown below was used instead of Synthesis Raw Material B2-2.

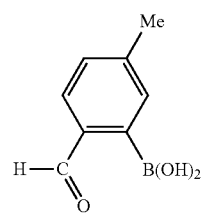 [SMILES: Cc1ccc(C=O)c(B(O)O)c1]

The structure of a purified product obtained by subjecting the synthesized iridium complex to sublimation purification under the condition of 1×10⁻⁴ Pa was confirmed by the same method as that of Synthesis Example 1. Table 1 shows the result.

TABLE 1

| | Ir complex | MS (calculated value) | MS (measured value) | Sublimation temperature (° C.) |
|---|---|---|---|---|
| Synthesis Example 1 | KK-01 | 900.05 | 900.22 | 390 |
| Synthesis Example 2 | KK-04 | 1012.27 | 1012.29 | 375 |
| Synthesis Example 3 | KK-05 | 1012.27 | 1012.36 | 390 |
| Synthesis Example 4 | KK-13 | 1040.32 | 1040.46 | 370 |
| Synthesis Example 5 | KK-28 | 984.21 | 984.35 | 370 |
| Synthesis Example 6 | KK-31 | 1096.42 | 1096.53 | 375 |
| Synthesis Example 7 | KK-32 | 1096.42 | 1096.50 | 370 |
| Synthesis Example 8 | KK-03 | 1012.27 | 1012.32 | 385 |
| Synthesis Example 9 | KK-12 | 1040.32 | 1040.42 | 370 |

TABLE 1-continued

| | Ir complex | MS (calculated value) | MS (measured value) | Sublimation temperature (° C.) |
|---|---|---|---|---|
| Synthesis Example 10 | KK-30 | 1096.42 | 1096.85 | 370 |
| Synthesis Example 11 | KK-36 | 1012.27 | 1012.49 | 370 |
| Comparative Example 1 | E2 | 1105.31 | 1105.52 | Thermal decomposition |

Synthesis Examples 12 to 14

Synthesis of Exemplified Compounds H101, H201, and H301

Exemplified Compounds H101, H201, and H301 were each synthesized according to the following synthesis scheme, specifically, by performing a complexation reaction in methanol involving using quinolin-8-ol as a starting raw material.

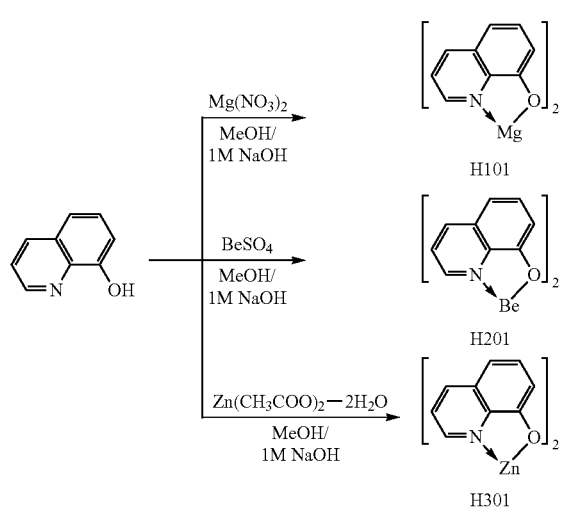

The resultant compounds (Exemplified Compounds H101, H201, and H301) were identified by MALDI-TOF-MS. Table 6 shows the results.

Synthesis Examples 15 to 18

Metal complexes were each synthesized by the same synthesis method as that of Synthesis Example 12 except that in Synthesis Example 12, the synthesis raw material was changed from quinolin-8-ol to a compound shown in Table 2 below. The structures of the resultant metal complexes were confirmed by the same method as that of Synthesis Example 12. Table 6 shows the results.

TABLE 2

| Starting raw material | Synthesized metal complex |
|---|---|
| Synthesis Example 15 | H119 |

TABLE 2-continued

| Starting raw material | Synthesized metal complex |
|---|---|
| Synthesis Example 16 | H126 |
| Synthesis Example 17 | H129 |
| Synthesis Example 18 | H130 |

Synthesis Examples 19 to 28

Metal complexes were each synthesized by the same synthesis method as that of Synthesis Example 13 except that in Synthesis Example 13, the synthesis raw material was changed from quinolin-8-ol to a compound shown in Table 3 or Table 4 below. The structures of the resultant metal complexes were confirmed by the same method as that of Synthesis Example 13. Table 6 shows the results.

TABLE 3

| Starting raw material | Synthesized metal complex |
|---|---|
| Synthesis Example 19 | H203 |
| Synthesis Example 20 | H207 |
| Synthesis Example 21 | H212 |

TABLE 3-continued

| | Starting raw material | Synthesized metal complex |
|---|---|---|
| Synthesis Example 22 | 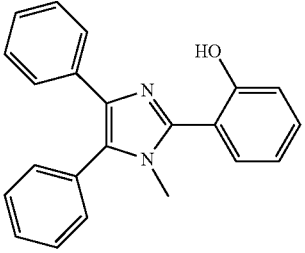 [SMILES: Cn1c(-c2ccccc2O)nc(-c2ccccc2)c1-c1ccccc1] | H216 |
| Synthesis Example 23 | 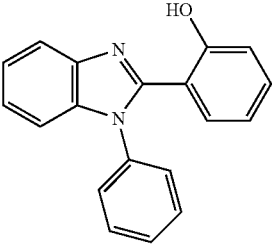 [SMILES: Oc1ccccc1-c1nc2ccccc2n1-c1ccccc1] | H218 |

TABLE 4

| | Starting raw material | Synthesized metal complex |
|---|---|---|
| Synthesis Example 24 | 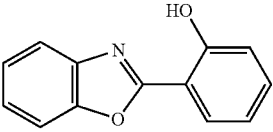 [SMILES: Oc1ccccc1-c1nc2ccccc2o1] | H219 |
| Synthesis Example 25 | 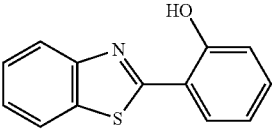 | H226 |
| Synthesis Example 26 | 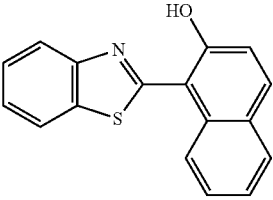 [SMILES: Oc1ccc2ccccc2c1-c1nc2ccccc2s1] | H229 |
| Synthesis Example 27 | 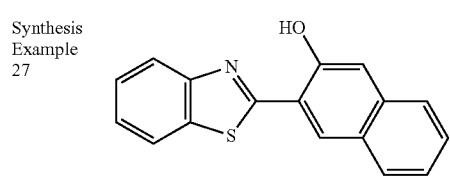 | H230 |

TABLE 4-continued

| | Starting raw material | Synthesized metal complex |
|---|---|---|
| Synthesis Example 28 | 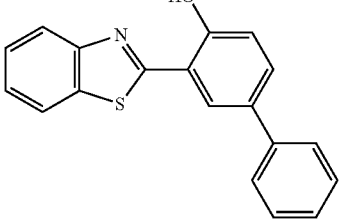 | H236 |

Synthesis Examples 29 to 31

Metal complexes were each synthesized by the same synthesis method as that of Synthesis Example 14 except that in Synthesis Example 14, the synthesis raw material was changed from quinolin-8-ol to a compound shown in Table 5 below. The structures of the resultant metal complexes were confirmed by the same method as that of Synthesis Example 14. Table 6 shows the results.

TABLE 5

| | Starting raw material | Synthesized metal complex |
|---|---|---|
| Synthesis Example 29 | 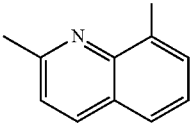 | H303 |
| Synthesis Example 30 | 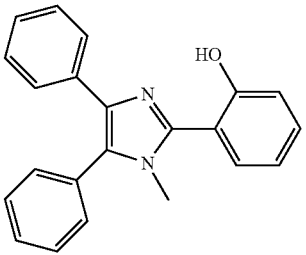 [SMILES: Cn1c(-c2ccccc2O)nc(-c2ccccc2)c1-c1ccccc1] | H316 |
| Synthesis Example 31 | 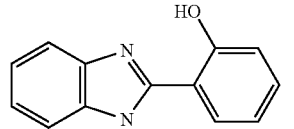 | H318 |

TABLE 6

| Exemplified Compound | MS (calculated value) | MS (measured value) |
|---|---|---|
| Synthesis Example 12 | H101 | 312.07 | 312.33 |
| Synthesis Example 13 | H201 | 297.10 | 297.23 |

TABLE 6-continued

| Exemplified Compound | MS (calculated value) | MS (measured value) |
|---|---|---|
| Synthesis Example 14 | H301 | 352.02 | 352.08 |
| Synthesis Example 15 | H119 | 444.10 | 444.22 |
| Synthesis Example 16 | H126 | 476.05 | 476.34 |
| Synthesis Example 17 | H129 | 576.08 | 576.53 |
| Synthesis Example 18 | H130 | 576.08 | 576.57 |
| Synthesis Example 19 | H203 | 325.13 | 325.98 |
| Synthesis Example 20 | H207 | 397.13 | 397.67 |
| Synthesis Example 21 | H212 | 425.16 | 425.51 |
| Synthesis Example 22 | H216 | 659.28 | 659.33 |
| Synthesis Example 23 | H218 | 579.22 | 579.52 |
| Synthesis Example 24 | H219 | 429.12 | 429.46 |
| Synthesis Example 25 | H226 | 461.08 | 461.34 |
| Synthesis Example 26 | H229 | 561.11 | 561.87 |
| Synthesis Example 27 | H230 | 561.11 | 561.81 |
| Synthesis Example 28 | H236 | 613.14 | 613.54 |
| Synthesis Example 29 | H303 | 380.05 | 380.11 |
| Synthesis Example 30 | H316 | 714.20 | 714.29 |
| Synthesis Example 31 | H318 | 579.22 | 579.53 |

Example 1

In this example, an organic light-emitting device having a construction in which "an anode/a hole transport layer/an electron blocking layer/an emission layer/a hole blocking layer/an electron transport layer/a cathode" were formed on a substrate in the stated order was produced by the following method.

First, ITO was formed into a film on a glass substrate and then subjected to desired patterning processing to form an ITO electrode (anode). At this time, the thickness of the ITO electrode was set to 100 nm. The substrate on which the ITO electrode had been thus formed was used as an ITO substrate in the following steps.

An organic light-emitting device was obtained by continuously forming, on the ITO substrate, organic compound layers and electrode layers shown in Table 7 below. It is to be noted that at this time, the electrode area of the opposing electrode (metal electrode layers, cathode) was set to 3 mm$^2$.

TABLE 7

| | Material | Thickness [nm] |
|---|---|---|
| Hole transport layer: HTL | HT2 | 40 |
| Electron blocking layer: EBL | HT7 | 10 |
| Emission layer | | |
| HOST | H-226 | |
| GUEST | KK-01 (H226:KK-01 = 96:4 (weight ratio)) | 30 |
| Hole blocking layer: HBL | ET3 | 10 |
| Electron transport layer: ETL | ET2 | 50 |
| First metal electrode layer | LiF | 0.5 |
| Second metal electrode layer | Al | 100 |

The characteristics of the resultant device were measured and evaluated by measuring its current-voltage characteristics with a microammeter 4140B manufactured by Hewlett-Packard Company and measuring its emission luminance with a BM7 manufactured by TOPCON CORPORATION. In this example, the light-emitting device had a maximum emission wavelength of 619 nm and chromaticity coordinates (x, y) of (0.66, 0.34).

As a result, emission efficiency when the organic light-emitting device of this example was caused to emit light with its luminance set to 2,000 cd/m$^2$ was 23.1 cd/A. In addition, the luminance half lifetime of the organic light-emitting device of this example at a current value of 100 mA/cm$^2$ was 400 hours.

Examples 2 to 22 and Comparative Examples 2 to 6

Organic light-emitting devices were each produced by the same method as that of Example 1 except that in Example 1, the compounds used as the hole transport layer (HTL), the electron blocking layer (EBL), the emission layer host (HOST), the emission layer guest (GUEST), the hole blocking layer (HBL), and the electron transport layer (ETL) were appropriately changed to compounds shown in Table 8 below. The characteristics of the resultant devices were measured and evaluated in the same manner as in Example 1. Table 8 shows the results of the measurement.

TABLE 8

| | HTL | EBL | HOST | GUEST | HBL | ETL | Emission efficiency at 2,000 cd/m$^2$ [ca/A] |
|---|---|---|---|---|---|---|---|
| Example 1 | HT2 | HT7 | H226 | KK-01 | ET3 | ET2 | 23.1 |
| Example 2 | HT2 | HT7 | H119 | KK-31 | ET3 | ET2 | 26.4 |
| Example 3 | HT1 | HT8 | H126 | KK-31 | ET3 | ET2 | 24.3 |
| Example 4 | HT1 | HT8 | H129 | KK-03 | ET3 | ET2 | 24.8 |
| Example 5 | HT1 | HT7 | H201 | KK-02 | ET3 | ET2 | 24.9 |
| Example 6 | HT1 | HT7 | H201 | KK-04 | ET4 | ET2 | 23.6 |
| Example 7 | HT1 | HT7 | H203 | KK-01 | ET4 | ET1 | 23.3 |
| Example 8 | HT2 | HT8 | H207 | KK-31 | ET3 | ET2 | 26.8 |
| Example 9 | HT2 | HT7 | H207 | KK-31 | ET3 | ET2 | 26.6 |
| Example 10 | HT2 | HT7 | H218 | KK-30 | ET4 | ET2 | 24.2 |
| Example 11 | HT2 | HT11 | H219 | KK-31 | ET4 | ET1 | 24.7 |
| Example 12 | HT2 | HT7 | H226 | KK-35 | ET3 | ET1 | 23.9 |
| Example 13 | HT1 | HT8 | H226 | KK-28 | ET3 | ET2 | 24.2 |
| Example 14 | HT1 | HT7 | H229 | KK-30 | ET4 | ET2 | 22.7 |
| Example 15 | HT2 | HT8 | H229 | KK-36 | ET3 | ET2 | 25.9 |
| Example 16 | HT2 | HT7 | H230 | KK-31 | ET3 | ET2 | 26.2 |

TABLE 8-continued

|  | HTL | EBL | HOST | GUEST | HBL | ETL | Emission efficiency at 2,000 cd/m$^2$ [ca/A] |
|---|---|---|---|---|---|---|---|
| Example 17 | HT2 | HT7 | H236 | KK-03 | ET3 | ET2 | 24.8 |
| Example 18 | HT2 | HT8 | H236 | KK-01 | ET3 | ET2 | 25.1 |
| Example 19 | HT2 | HT8 | H301 | KK-02 | ET4 | ET2 | 23.0 |
| Example 20 | HT2 | HT7 | H303 | KK-03 | ET7 | ET2 | 23.1 |
| Example 21 | HT1 | HT7 | H316 | KK-03 | ET3 | ET2 | 24.1 |
| Example 22 | HT1 | HT11 | H318 | KK-28 | ET3 | ET1 | 24.3 |
| Comparative Example 2 | HT1 | HT7 | H226 | RD3 | ET3 | ET2 | 13.2 |
| Comparative Example 3 | HT1 | HT8 | H226 | RD4 | ET3 | ET2 | 13.1 |
| Comparative Example 4 | HT2 | HT7 | EM9 | RD6 | ET4 | ET2 | 17.5 |
| Comparative Example 5 | HT2 | HT7 | EM8 | RD7 | ET4 | ET2 | 18.9 |
| Comparative Example 6 | HT2 | HT7 | EM9 | KK-31 | ET3 | ET2 | 21.8 |

Each of the organic light-emitting devices of Comparative Examples 2 to 5 had a lower emission efficiency than those of the organic light-emitting devices of Examples. This is caused by the fact that the guest in the emission layer is not the iridium complex represented by the general formula [1] (iridium complex having an arylnaphtho[2,1-f]isoquinoline ligand). In addition, the organic light-emitting device of Comparative Example 6 has a lower emission efficiency than those of the organic light-emitting devices of Examples, though the difference is slight. This can be said to be because the efficiency of energy transfer from the host to the guest is lower than that of each of the organic light-emitting devices of Examples.

In addition, the luminance half lifetimes of the organic light-emitting devices of Examples 1 to 22 at a current value of 100 mA/cm$^2$ were about 200 hours to 400 hours. In other words, the devices had long lifetimes.

Therefore, the organic light-emitting device of the present invention, specifically, the organic light-emitting device including the metal complex compound (host) lengthening the lifetime of the emission layer and the iridium complex represented by the general formula [1] (guest) imparting high emission efficiency to the layer was found to have high emission efficiency and a long lifetime.

Example 23

In this example, an organic light-emitting device having a construction in which "an anode/a hole transport layer/an electron blocking layer/an emission layer/a hole blocking layer/an electron transport layer/a cathode" were formed on a substrate in the stated order was produced. It is to be noted that in this example, the emission layer contains an assist material.

First, organic compound layers and electrode layers shown in Table 9 below were continuously formed on an ITO substrate that had been produced by the same method as that of Example 1. It is to be noted that at this time, the electrode area of the opposing electrode (metal electrode layers, cathode) was set to 3 mm$^2$.

TABLE 9

|  | Material | Thickness (nm) |
|---|---|---|
| Hole transport layer: HTL | HT2 | 40 |
| Electron blocking layer: EBL | HT7 | 10 |
| Emission layer |  |  |
| HOST | H-229 |  |
| ASSIST | HT2 | 30 |
| GUEST | KK-03 |  |
|  | (H229:HT-2:KK-03 = 80:15:5 (weight ratio)) |  |
| Hole blocking layer: HBL | ET3 | 10 |
| Electron transport layer: ETL | ET1 | 50 |
| First metal electrode layer | LiF | 0.5 |
| Second metal electrode layer | Al | 100 |

The characteristics of the resultant device were measured and evaluated in the same manner as in Example 1. Here, the organic light-emitting device of this example had a maximum emission wavelength of 621 nm and chromaticity coordinates (x, y) of (0.66, 0.34). In addition, the device had an emission efficiency at the time of its light emission at a luminance of 1,500 cd/m$^2$ of 35.3 cd/A and a luminance half lifetime at a current value of 100 mA/cm$^2$ of 210 hours.

Examples 24 to 30

Organic light-emitting devices were each produced by the same method as that of Example 23 except that in Example 23, the compounds used as the hole transport layer (HTL), the electron blocking layer (EBL), the emission layer host (HOST), the emission layer assist (ASSIST), the emission layer guest (GUEST), the hole blocking layer (HBL), and the electron transport layer (ETL) were changed as shown in Table 10. The characteristics of the resultant devices were measured and evaluated in the same manner as in Example 23. Table 10 shows the results of the measurement.

TABLE 10

|  | HTL | EBL | HOST | ASSIST | GUEST | HBL | ETL | Emission efficiency at 2,000 cd/m$^2$ [ca/A] |
|---|---|---|---|---|---|---|---|---|
| Example 23 | HT2 | HT7 | H229 | HT2 | KK-03 | ET3 | ET1 | 35.3 |
| Example 24 | HT1 | HT8 | H129 | GD6 | KK-02 | ET3 | ET2 | 30.2 |
| Example 25 | HT2 | HT7 | H201 | HT2 | KK-04 | ET3 | ET2 | 37.2 |
| Example 26 | HT2 | HT11 | H219 | GD6 | KK-01 | ET4 | ET1 | 32.9 |
| Example 27 | HT2 | HT7 | H226 | GD6 | KK-02 | ET7 | ET2 | 38.4 |
| Example 28 | HT2 | HT7 | H229 | GD6 | KK-31 | ET3 | ET2 | 35.8 |
| Example 29 | HT3 | HT8 | H236 | HT1 | KK-31 | ET4 | ET2 | 32.4 |
| Example 30 | HT2 | HT7 | H318 | HT2 | KK-03 | ET3 | ET2 | 34.3 |

The foregoing shows that the organic light-emitting device of the present invention, whose emission layer contains the metal complex compound exhibiting a lifetime-lengthening effect and the niq-based Ir complex imparting high emission efficiency, is an organic light-emitting device having high emission efficiency and a long luminance half lifetime. In addition, the luminance half lifetimes of the organic light-emitting devices of Examples 23 to 30 at a current value of 100 mA/cm² were about 200 hours to 350 hours, and hence the devices were found to be long-lifetime and high-performance light-emitting devices.

As described above by way of the embodiments and Examples, the organic compound layer (especially the emission layer) of the organic light-emitting device of the present invention contains an iridium complex having an arylnaphtho[2,1-f]isoquinoline ligand having high efficiency as a guest and a metal complex compound having high stability as a host. Accordingly, according to one embodiment of the present invention, there can be provided an organic light-emitting device having a good device lifetime characteristic.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-021048, filed on Feb. 6, 2013, which is hereby incorporated by reference herein in its entirety.

The invention claimed is:

1. An organic light-emitting device, comprising:
a pair of electrodes; and
an organic compound layer placed between the pair of electrodes,
wherein the organic compound layer comprises an iridium complex represented by the following general formula [1] and a metal complex represented by the following general formula [5]:

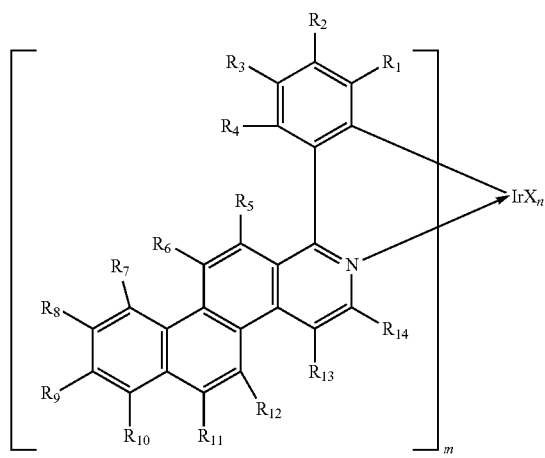

[1]

in the formula [1]:
m represents an integer of 1 to 3, and n represents an integer of 0 to 2, provided that a relationship of m+n=3 is satisfied;
$R_1$ to $R_{14}$ each represent a hydrogen atom, a halogen atom, an alkyl group, an alkoxy group, a substituted amino group, a substituted or unsubstituted aryl group, or a substituted or unsubstituted heterocyclic group, and may be identical to or different from one another, provided that when m represents 3 or when X is free of an alkyl group, at least one of substituents represented by $R_1$ to $R_{14}$ comprises an alkyl group;
X represents a bidentate ligand; and
a partial structure $IrX_n$ represents any one of partial structures represented by the following general formulae [2] to [4]:

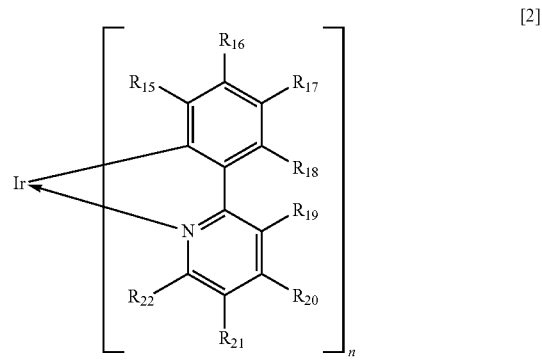

[2]

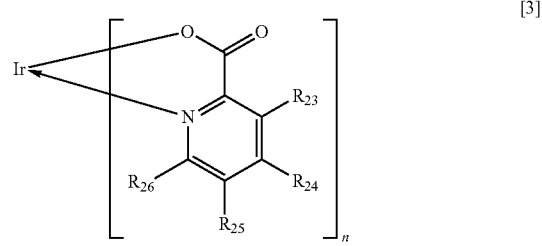

[3]

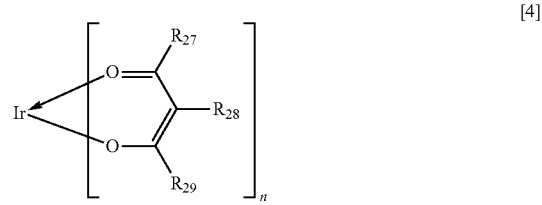

[4]

in the formulae [2] to [4], $R_{15}$ to $R_{29}$ each represent a hydrogen atom, a halogen atom, an alkyl group, an alkoxy group, a substituted amino group, a substituted or unsubstituted aryl group, or a substituted or unsubstituted heterocyclic group, and may be identical to or different from one another, provided that when none of $R_1$ to $R_{14}$ represents an alkyl group, at least one of substituents represented by $R_{15}$ to $R_{29}$ comprises an alkyl group, and when n represents 2, multiple substituents represented by any one of $R_{15}$ to $R_{29}$ may be identical to or different from each other;

$$ML_2 \quad [5]$$

in the formula [5]:
M represents a divalent metal atom selected from beryllium, magnesium, and zinc;
L represents a bidentate ligand;
when M represents beryllium or magnesium, a partial structure ML comprises any one of structures represented by the following general formulae [6] to [11]; and
when M represents zinc, the partial structure ML comprises any one of structures represented by the following general formulae [7] to [11]:

[6] 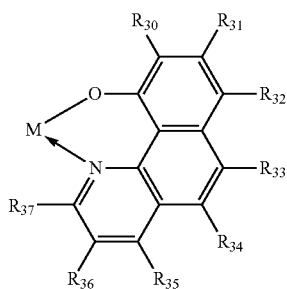

[7] 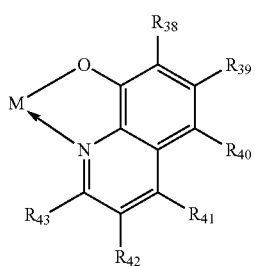

[8] 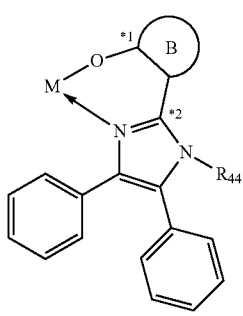

[9] 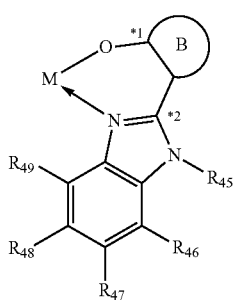

[10] 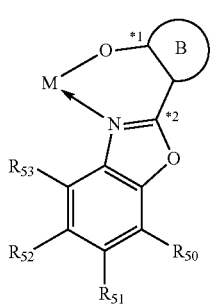

[11] 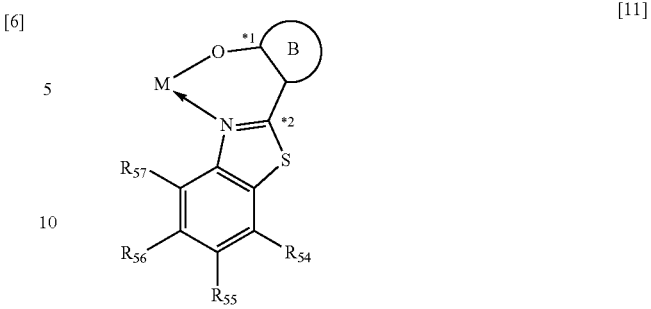

in the formulae [6] to [11], $R_{30}$ to $R_{57}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group, and in the formulae [8] to [11], a ring B comprises any one of cyclic structures represented by the following general formulae [12] to [14], *1 represents a bonding position with an oxygen atom, and *2 represents a bonding position with a carbon atom in a five-membered heterocyclic skeleton:

[12] 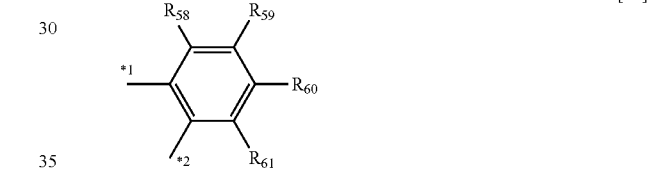

[13] 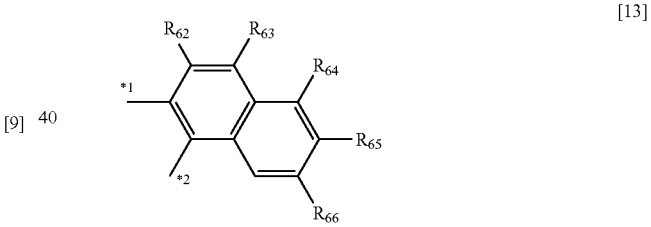

[14] 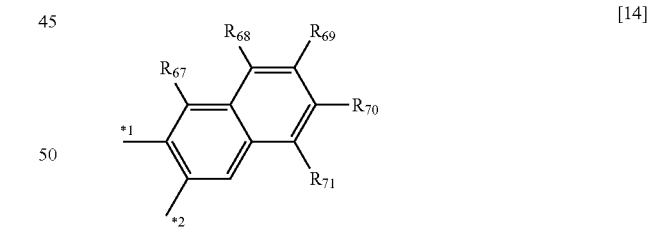

in the formulae [12] to [14], $R_{58}$ to $R_{71}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

2. The organic light-emitting device according to claim 1, wherein the m represents 2 and the n represents 1.

3. The organic light-emitting device according to claim 1, wherein the iridium complex represented by the general formula [1] comprises a compound represented by the following general formula [15]:

[15]

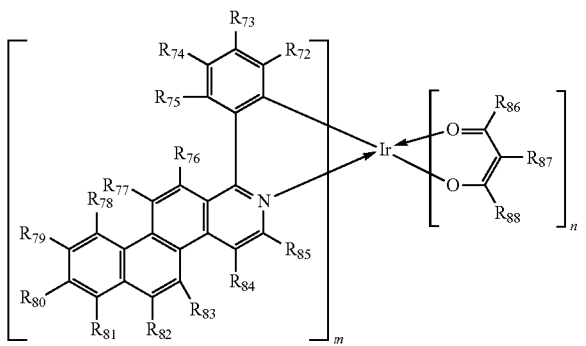

in the formula [15]:

$R_{72}$ to $R_{88}$ each represent a hydrogen atom, a halogen atom, an alkyl group, an alkoxy group, a substituted amino group, a substituted or unsubstituted aryl group, or a substituted or unsubstituted heterocyclic group, provided that at least one of $R_{72}$ to $R_{88}$ represents an alkyl group; and m represents an integer of 1 to 3, and n represents an integer of 0 to 2, provided that a relationship of m+n=3 is satisfied.

4. The organic light-emitting device according to claim 1, wherein the iridium complex represented by the general formula [1] comprises a compound represented by the following general formula [16]:

[16]

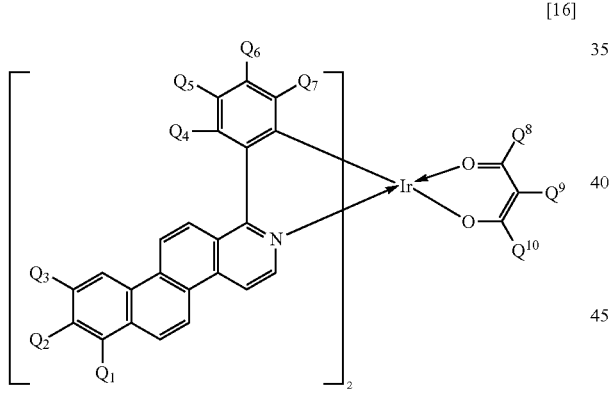

in the formula [16], $Q_1$ to $Q_{10}$ each represent a hydrogen atom, an alkyl group, an alkoxy group, a substituted amino group, or a substituted or unsubstituted phenyl group, provided that at least one of $Q_1$ to $Q_{10}$ represents an alkyl group.

5. The organic light-emitting device according to claim 1, wherein the organic compound layer comprises an emission layer including a host and a guest;

the guest comprises the iridium complex represented by the general formula [1]; and the host comprises the metal complex compound represented by the general formula [5].

6. The organic light-emitting device according to claim 5, wherein the organic compound layer further includes an assist material different from the host and the guest.

7. The organic light-emitting device according to claim 6, wherein the assist material comprises an iridium complex.

8. The organic light-emitting device according to claim 1, wherein the device emits red light.

9. A display apparatus, comprising multiple pixels, wherein the pixels each include the organic light-emitting device according to claim 1 and an active device connected to the organic light-emitting device.

10. A lighting apparatus comprising:

the organic light-emitting device according to claim 1; and an AC/DC converter circuit connected to the organic light-emitting device.

11. An image-forming apparatus comprising:

a photosensitive member;

charging unit for charging a surface of the photosensitive member;

exposing unit for exposing the photosensitive member to form an electrostatic latent image; and developing unit for developing the electrostatic latent image formed on the surface of the photosensitive member, wherein the exposing unit includes the organic light-emitting device according to claim 1.

12. An exposing apparatus for exposing a photosensitive member, comprising a plurality of the organic light-emitting devices according to claim 1, wherein the organic light-emitting devices are arranged to form a line along a predetermined direction.

* * * * *